United States Patent [19]

Schaub et al.

[11] 4,178,461

[45] Dec. 11, 1979

[54] 16,16-SPIROCYCLOALKYL PROSTAGLANDIN DERIVATIVES

[75] Inventors: Robert E. Schaub, Upper Saddle River; Martin J. Weiss, Oradell, both of N.J.

[73] Assignee: American Cyanamid Company, Stamford, Conn.

[21] Appl. No.: 778,302

[22] Filed: Mar. 16, 1977

Related U.S. Application Data

[62] Division of Ser. No. 592,494, Jul. 2, 1975, Pat. No. 4,028,396.

[51] Int. Cl.$^2$ ............................................ C07C 177/00
[52] U.S. Cl. ...................................... 562/463; 560/53; 562/468
[58] Field of Search ............................ 560/53, 57, 60; 260/520, 515; 562/463, 468

[56] References Cited

U.S. PATENT DOCUMENTS

| | | | |
|---|---|---|---|
| 3,931,289 | 1/1976 | Bundy | 260/473 |
| 4,045,468 | 8/1977 | Kurono et al. | 260/468 |

*Primary Examiner*—Robert Gerstl

[57] ABSTRACT

This disclosure describes novel 15-hydroxy-16,16-spirocycloalkyl prostanoic acids and derivatives and congeners thereof which are useful as bronchodilators and gastric acid secretion inhibitors.

9 Claims, No Drawings

16,16-SPIROCYCLOALKYL PROSTAGLANDIN DERIVATIVES

This is a division, of application Ser. No. 592,494, filed July 2, 1975 now U.S. Pat. No. 4,028,396.

BRIEF SUMMARY OF THE INVENTION

This invention relates to novel 15-hydroxy-16,16-spirocycloalkylprostanoic acids and derivatives and congeners thereof as well as to intermediates and methods for their preparation. The novel compounds of this invention embrace all the optical antipodes, racemic mixtures, and diasteromeric mixtures corresponding to the following general formula, the absolute configuration of which is that of the natural mammallian prostaglandins. More particularly, the compounds of this invention may be represented by the following formula or a racemic compound of the formula and the mirror image thereof.

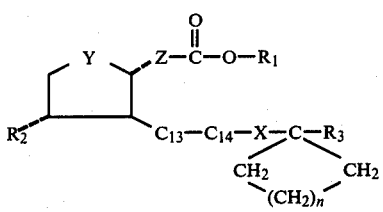

wherein $R_1$ is selected from the group consisting of hydrogen, tetrahydropyranyl, tri-lower alkyl (1–4 carbon atoms, inclusive)silyl, straight or branched-chain alkyl of from 1 to 12 carbon atoms, inclusive; n is the integer 1 or 2; $R_2$ is selected from the group consisting of hydrogen, hydroxy, tetrahydropyranyloxy, tri-lower alkyl (1 to 4 carbon atoms, inclusive)silyloxy, and alkanoyloxy of from 2 to 5 carbon atoms, inclusive; $R_3$ is selected from the group consisting of straight or branched chain alkyl groups of from 3 to 7 carbon atoms, inclusive, straight or branched chain alkenyl or alkynyl groups of from 3 to 7 carbon atoms, inclusive, benzyl or phenethyl groups; the moiety $C_{13}$–$C_{14}$ is ethylene, or trans-vinylene; X is a divalent radical selected from the group consisting of:

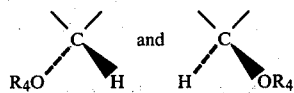

wherein $R_4$ is hydrogen, tri-loweralkylsilyl, or an alkanoyl group of from 2 to 5 carbon atoms, inclusive; Y is a divalent radical of the group consisting of

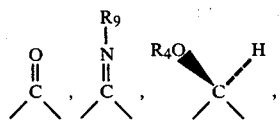

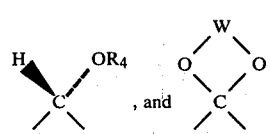

wherein $R_4$ is as hereinabove defined; $R_9$ is selected from the group consisting of hydroxy, lower alkoxy of from 1 to 3 carbon atoms inclusive, ureido, thioureido, and anilino optionally substituted with one or two radicals selected from the group consisting of carboxy, carboxamido, halogen, lower alkyl of 1 to 3 carbon atoms, inclusive, lower alkoxy of 1 to 3 carbon atoms, inclusive, trifluoromethyl, mono- or di-lower alkylamino of 1 to 3 carbon atoms, inclusive; and W is ethylene or 1,3-trimethylene each of which is optionally substituted with one or two lower alkyl groups of from 1 to 3 carbon atoms, inclusive, or a halomethyl group; Z is a divalent radical selected from the group consisting of:

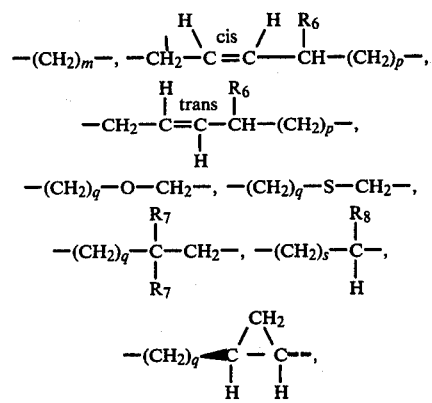

wherein m is an integer from 4 to 8, inclusive; p is an integer from 1 to 4, inclusive; q is an integer from 2 to 6, inclusive; s is an integer from 3 to 7, inclusive; $R_6$ is hydrogen or a lower alkyl group of from 1 to 3 carbon atoms, inclusive; $R_7$ is a lower alkyl group of from 1 to 3 carbon atoms, inclusive; and $R_8$ is phenyl or a lower alkyl group of from 1 to 3 carbon atoms; and the divalent moiety

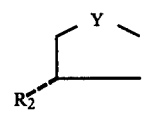

may be the divalent moiety

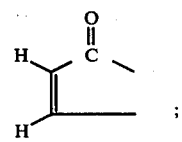

and the moiety

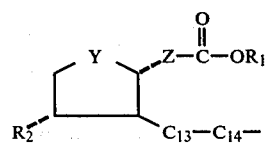

may be

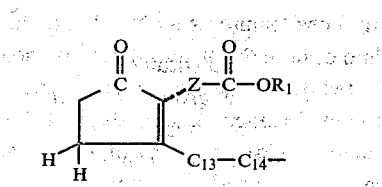

and when $R_1$ is hydrogen the pharmaceutically acceptable salts thereof.

DETAILED DESCRIPTION OF THE INVENTION

Useful pharmacologically acceptable salts of the above formula wherein $R_1$ is hydrogen are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic solutions are preferred. For that purpose, it is preferred because of increased water solubility that $R_1$ be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom et al., *J. Biol. Chem.*, 238, 3555 (1963) and Horton, *Experientia*, 21, 113 (1965) and references cited therein. All of the so called natural prostaglandins are derivatives of prostanoic acid:

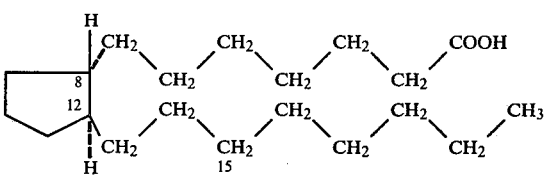

The hydrogen atoms attached to C-8 and C-12 are in trans-configuration. The natural prostaglandins represent only one of the possible optical isomers. The compounds of this invention include all possible optical isomers.

The $C_{15}$ position is a particularly important one and when it is substituted by a hydroxy or an alkanoyloxy group, and a hydrogen atom, it is asymmetric, with the possibility of two configurations, deemed S or R. In partial formula (A) below is shown the "natural" configuration of $C_8$, $C_{12}$, and $C_{15}$ as it is found in all known mammallian prostaglandins. The configuration at $C_8$ and $C_{12}$ is referred to as l and at $C_{15}$ as S; thus formula (A) is the l 15(S) or nat form. The enantiomer of (A) is represented by partial formula (B), the d 15(R) or ent form, and a substance deemed a dl-racemate without designation with regard to the situation at $C_{15}$ consists of enantiomers (A) and (B). Partial formula (C) represents a structure wherein the configuration at $C_8$ and $C_{12}$ is as in (A), the l form, but the configuration at $C_{15}$ is inverted to the R form. A structure embracing the configuration at $C_8$, $C_{12}$, and $C_{15}$ as shown in (C) is referred to as an l 15-epi derivative, the enantiomeric structure is represented by partial formula (D), the d 15-epi derivative, and (C) and (D) constitutes a dl-15-epi racemate.

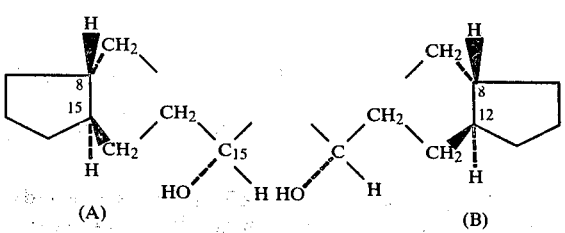

-continued

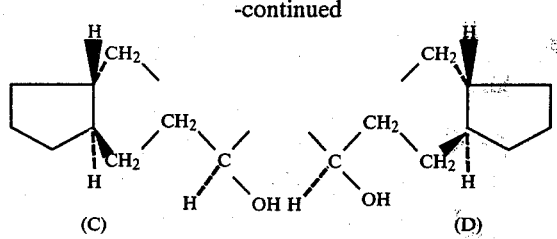

The compounds of this invention include all possible antipodes and particularly both possible configurations for $C_{15}$.

The novel compounds of this invention can be prepared by the reaction sequences illustrated in Flowsheet A below, wherein n, $R_3$, and Z are as defined hereinabove and $R'_1$ has all the values of $R_1$ except for hydrogen, preferably it is lower alkyl, tetrahydropyranyl or tri lower alkylsilyl, $R''_1$ has all the values of $R_1$ except tetrahydropyranyl, or tri-lower alkylsilyl; $R'_2$ is hydrogen, or tetrahydropyranyloxy, or tri-lower alkylsilyloxy and $R''_2$ is hydrogen or hydroxy, and X is iodide, bromide, methanesulfonyloxy, or p-toluenesulfonyloxy or the like.

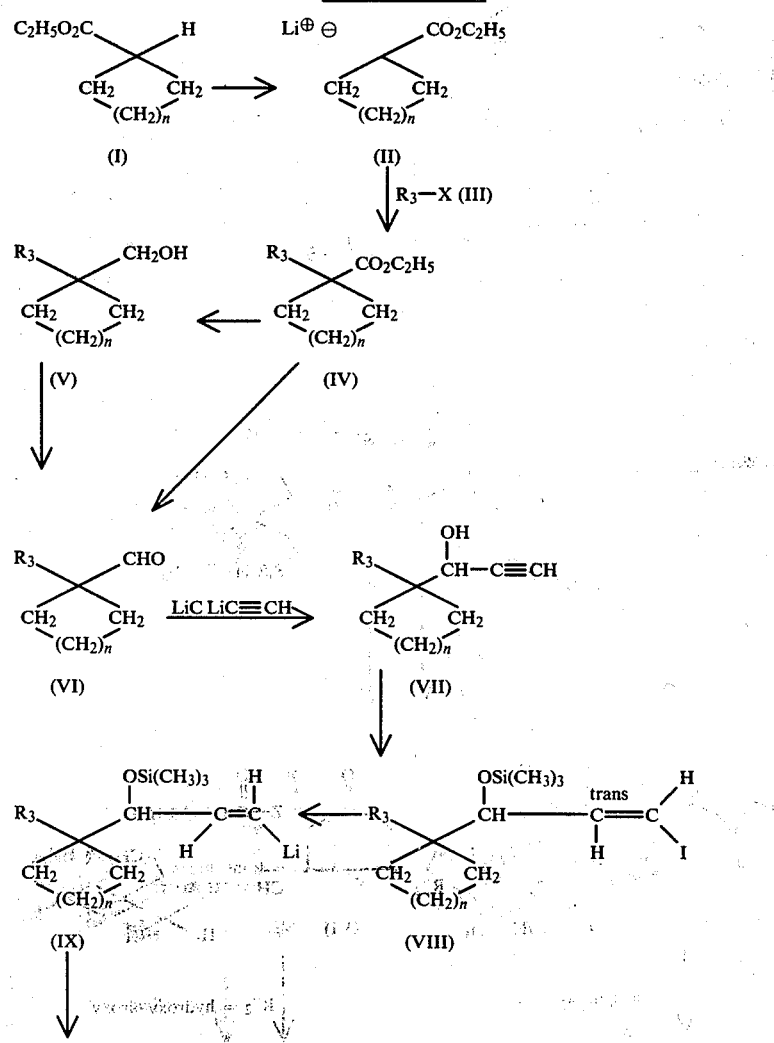

FLOWSHEET A
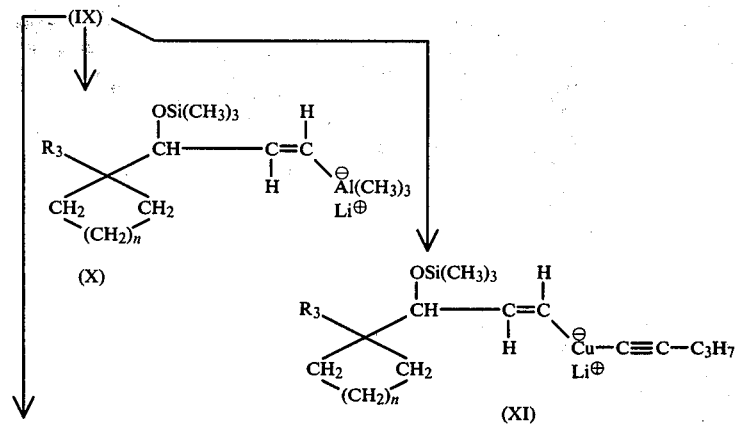
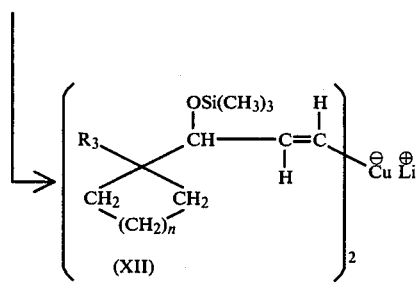
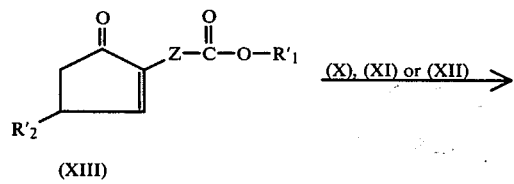
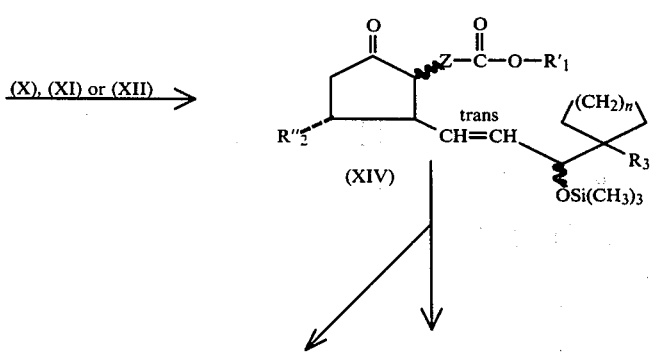
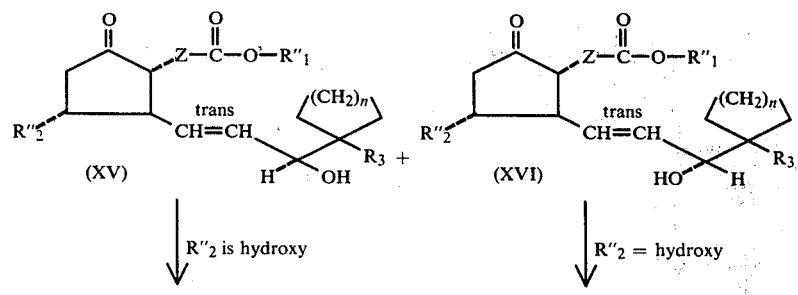

FLOWSHEET A
-continued

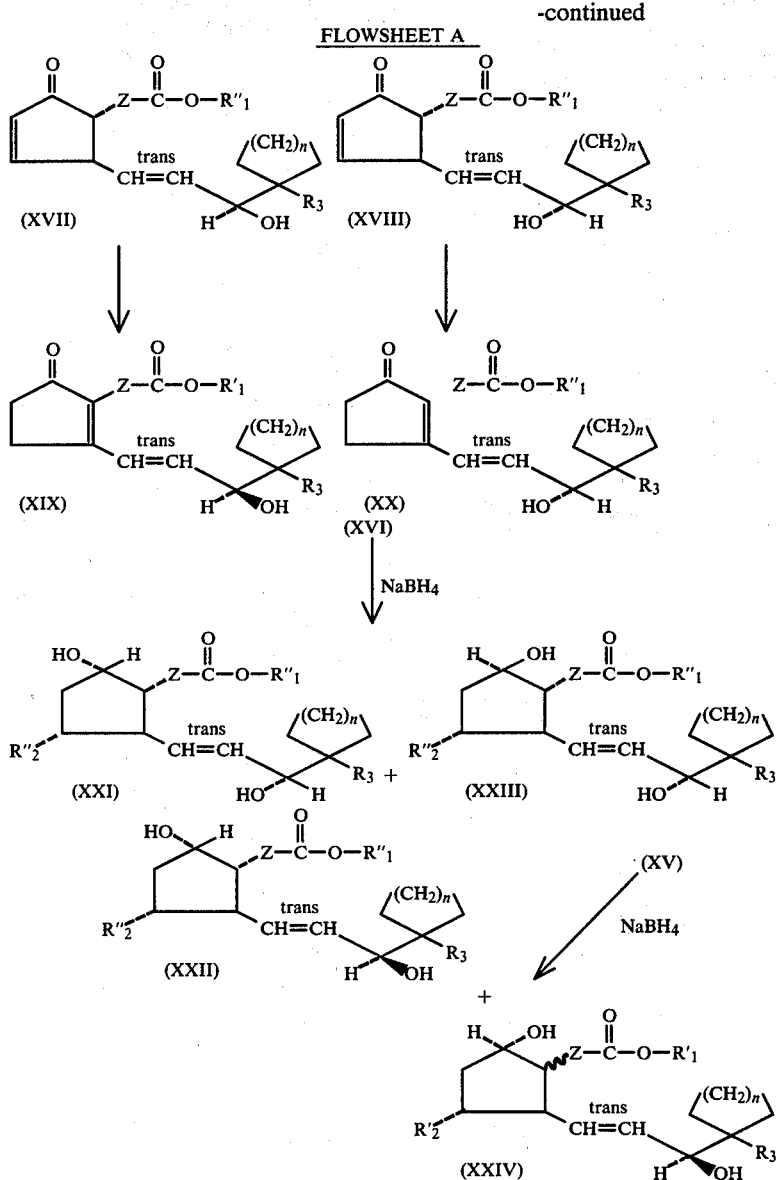

In accordance with the scheme as outlined hereinabove in Flowsheet A, carbethoxycyclobutane or carbethoxycyclopentane is converted to its enolate anion (II) by treatment with a strong base such as lithium cyclohexylisopropylamide, prepared from the corresponding amine and n-butyl lithium (hexane solution) in a solvent, such as anhydrous tetrahydrofuran, at very low temperatures, such as −78° C. The resulting enolate anion (II) is then alkylated with $R_3$-X (III) to provide (IV), the ester group of which is reduced to alcohol (V) by reaction with 2 equivalents of diisobutyl aluminum hydride, lithium aluminum hydride or the like. Oxidation of alcohol (V) with dipyridine chromium (VI) oxide complex ["Reagents for Organic Synthesis", L. F. Fieser and M. Fieser, John Wiley and Sons, Inc., New York, Vol. 4, page 215 (1974)], prepared in situ in methylene chloride solution, provides the corresponding aldehyde (VI), which can also be obtained directly from ester (IV) by partial reduction with one equivalent of diisobutyl aluminum hydride at −78° C., but the former two-step procedure is preferable. Reaction of aldehyde (VI) with lithium acetylide ethylene diamine complex provides the 3-hydroxy-1-alkyne (VII), which is converted to its trimethylsilyl ether in the usual manner. The silylated derivative is then treated with disiamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-trans-1-alkene (VIII).

The vinyl iodide (VIII) is converted to the transvinyl lithium derivative (IX) with clean retention of configuration by treatment at about −78° C. in hexane (isomeric mixture) solution with either one equivalent of n-butyl lithium or two equivalents of t-butyl lithium. It is preferable for this treatment to proceed for about one hour at −78° C., then for about one hour at −40° C. and finally for about one hour at about 0° C. For the subsequent preparation of lithio alanate reagents (X) it is preferable to use n-butyl lithium, and for the lithio cuprate reagents (XI) or (XII) t-butyl lithium is the agent of choice.

For the preparation of the alanate reagent (X) or the like, a molar equivalent of a tri-lower alkyl (1–5 carbon atoms) aluminum (e.g., trimethyl aluminum), dissolved in a solvent such as hexane, is added to the vinyl lithium derivative (IX) at about 0° C. After about 15–45 minutes at this temperature the requisite blocked cyclopentenone (XIII) is added and the reaction mixture is stirred for about 18 hours at ambient temperatures. The mixture is quenched with aqueous hydrochloric acid in the cold and the product is obtained by extraction. In the 11-deoxy series the blocking trialkylsilyl group is removed on treatment with acetic acid:tetrahydrofuran:water (4:2:1) at room temperatures for about twenty minutes. The ester group can then be saponified in the usual manner. In the 11-oxy series, the silyl and/or tetrahydropyranyl groups are removed by treatment with acetic acid:water:tetrahydrofuran (20:10:3) at about 40° C. for about 4 hours. Alkyl esters of the 11-oxy series are not disturbed by this treatment and cannot be saponified by chemical means in view of the instability of the 11-hydroxy-9-ketone to base treatment. However, the ester can be cleaved by treatment with Baker's Yeast, a procedure well-known in the art.

For the preparation of the asymmetrical lithio cuprate (XI) or the like, a solution of one molar equivalent of copper (I)-1-alkyne, preferably copper (I)-1-pentyne in anhydrous hexamethylphosphorous triamide, preferably three to five molar equivalents, and anhydrous ether is added to one molar equivalent of the aforementioned vinyl lithium (IX) solution cooled to about −78° C. After about one hour at this temperature, a molar equivalent of the requisite cyclopentenone (XIII) is added. After several hours at −15° C. to 0° C. the reaction mixture is quenched with aqueous ammonium chloride solution and the blocked product (XIV) is isolated in the usual manner. The deblocking of this product is then carried out in the manner as described hereinabove.

The products are finally purified by chromatographic procedures in the usual manner. The 15-normal (see XVI) and 15-epi (see XV) racemates or diasteromers are separable on chromatography. In the 11-deoxy series, this separation can be effected at either the alkyl ester or prostenoic acid stage.

For the preparation of the symmetrical lithio cuprate (XII) one molar equivalent of copper (I) iodide tributylphosphine complex, dissolved in anhydrous ether, is added at about −78° C. to two molar equivalents of the aforementioned vinyl iodide (IX) solution in hexanes, cooled to −78° C. After about one hour at this temperature, the lithio cuprate (XII) is treated with the requisite cyclopentenone (XIII) as described hereinabove for the conjugate addition with the 1-alkynyl lithio cuprate (XI).

In order to ensure a trans-relationship in (XIV), (XV) or (XVI), these products can be submitted to conditions known in the literature to equilibrate cis 8-iso-PGE$_1$ to a mixture containing about 90% of the trans-product [see E. G. Daniels et al., Journ. Amer. Chem. Soc., 90, 5894 (1968)]. These conditions involve treatment with potassium acetate in aqueous methanol for about 96 hours at room temperature. The cis and trans products are separable by chromatographic procedures.

Most of the cyclopentenones required for the purposes of this invention have been described in the literature or can be prepared by procedures quite analogous to those already described. Appropriate references are provided in the examples which follow. The synthesis of certain non-reference requisite cyclopentenones is also described therein.

Treatment of the 11-hydroxy derivatives represented by formulae (XV) or (XVI) in which $R''_2$ is hydroxy with dilute acid results in dehydration of the β-ketol system and the formation of the corresponding $\Delta^{10}$ derivatives (XVII) or (XVIII) (prostaglandins of the A type). A preferred procedure involves treatment in tetrahydrofuran:water (2:1) solvent 0.5 N in hydrochloric acid for about twenty hours at ambient temperatures. Under these conditions tetrahydropyranyl or trialkylsilyl esters undergo hydrolysis if this procedure is applied to the initial conjugate addition product (XIV). More prolonged treatment with acid or preferably treatment with dilute base, e.g., sodium carbonate in aqueous methanol or an amine such as piperidine, effects the conversion of (XVII) or (XVIII) to the $\Delta^{8(12)}$ derivatives (XIX) or (XX) (prostaglandins of the B type).

The 9-keto derivatives (XV) or (XVI) of this invention can be converted to the corresponding 9-hydroxy derivatives. If this conversion is effected with sodium borohydride, the product is a mixture of 9α- and 9β-hydroxy derivatives (prostaglandins of the Fα and Fβ series, respectively): (XXI) and (XXIII), respectively, from (XVI) and (XXII) and (XXIV), respectively, from (XV). The 9α and 9β derivatives are separable from each other by chromatographic procedures well-known in the art.

When the reduction is carried out with lithium perhydro-9b-boraphenalyl hydride [H. C. Brown and W. C. Dickason, Journ. Amer. Chem. Soc., 92, 709 (1970)] or with lithium tri(sec-butyl)borohydride [H. C. Brown and S. Krishnamurthy ibid. 94, 7159 (1972)], the product is at least predominantly the 9α-hydroxy derivative (XXI) or (XXII), wherein the 9-hydroxy group is cis to the side-chain attached to $C_8$ and to the 11-oxy function, if present. In accordance with accepted convention, an α-substituent at the 8-, 9-, 11- or 12-positions is behind the plane of the paper whereas a β-substituent at these positions is in front of the plane of the paper. This is usually represented by a --- bond for an α substituent, a ―bond for a β-substituent, and a ∿bond where both possibilities are indicated.

The 13-dihydro derivatives ($C_{13}$–$C_{14}$ is ethylene) of this invention can be prepared by reduction of the $\Delta^{13}$ function in the corresponding 13-prostenoic acids or esters. This reduction can be accomplished by catalytic reduction, preferably at low pressure with a noble metal catalyst in an inert solvent at ambient temperatures.

The 13-dihydro derivatives can also be prepared by treating cycloalkenones of formula (XIII) with Grignard reagent (XXV), wherein B is an appropriate blocking group such as trimethylsilyl or t-butyl, in the usual manner in the presence of a catalyst such as the tributylphosphine cuprous iodide complex. The trimethylsilyl and other blocking groups are then removed in the usual manner as described hereinabove. The 15-O-t-butyl blocking group in the conjugate addition product can be efficiently removed by treatment with neat trifluoroacetic acid in the cold for about twenty minutes followed by brief treatment with aqueous ammonia because of potential 15-O-trifluoroacetylation. [For an appropriate reference see R. E. Schaub and M. J. Weiss, Tetrahedron Letters, 129 (1973)]. The use of (XXV) rather than catalytic reduction provides a cleaner procedure for the preparation of 13-dihydro derivatives embracing a double bond elsewhere in the molecule.

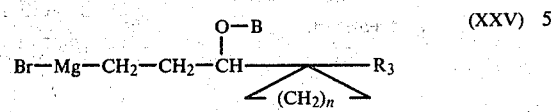  (XXV)

The novel 5,6-trans-ene derivatives of this invention can be prepared according to the procedures of Flowsheet A wherein Z is

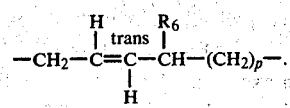

They are also available from the corresponding 5,6-cis-ene derivatives on irradation at about 25° C. of an oxygen-free benzene-methanol solution of the 5,6-cis-ene with 3500-A light for about 24 hours in the presence of diphenylsulfide. For a pertinent literature analogy, see G. L. Bundy et al., *Journ. Amer. Chem. Soc.*, 94, 2124 (1972) and U.S. Pat. No. 3,821,291 (June 28, 1974).

For the preparation of those compounds of this invention wherein Y in the generic formula above is

(see E and F below), the 9-oxo derivative (XV) or (XVI) are treated in usual manner, well-known in the art, with the appropriate reagent of the formula $R_9$-$NH_2$, wherein $R_9$ is as defined hereinabove. In structures (E) and (F) below, $R_1$, $R''_2$, $R_3$, $R_5$, $R_9$, Z, n and $C_{13}$-$C_{14}$ are as hereinabove defined.

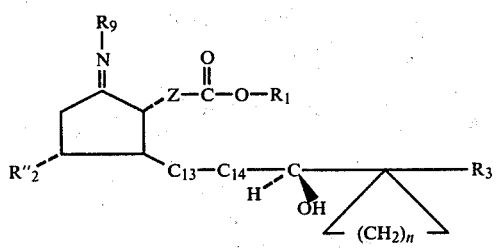  (E)

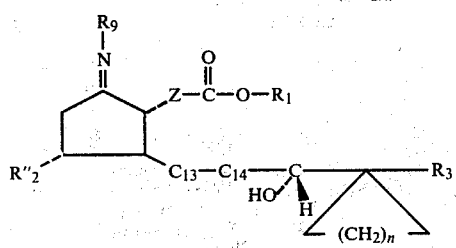  (F)

The preparation of the novel 9,9-alkylenedioxy derivatives (Y =

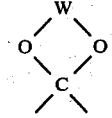

in generic formula shown hereinabove) of this invention is carried out in the 11-deoxy series in the usual manner, well-established in the art by treating the corresponding 9-oxo derivatives with a glycol of the formula

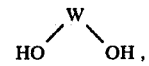

wherein W is as hereinabove defined, in the presence of an acid catalyst such as p-toluenesulfonic acid. It is preferable to carry out this reaction in a solvent such as benzene and to remove the by-product water as it is formed.

The preparation of certain 9,9-alkylenedioxy derivatives in the 11-oxy series can be accomplished from (XXXIII) (XXXIV). For the synthesis of (XXXIII) see D. Taub et al., *Tetrahedron*, 29, 1447 (1973), and for (XXXIV) see H. L. Slates et al., *J.C.S. Chem. Comm.*, 304 (1972). Intermediate (XXXIV) has also been obtained in the resolved state and use of its resolved enantiomers provides the 9,9-alkenedioxy derivatives of this invention in optically active form.

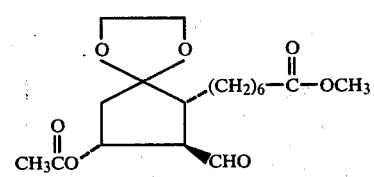  (XXXIII)

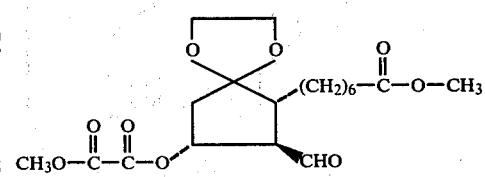  (XXXIV)

Treatment of (XXXIII), or (XXXIV), at ambient temperature for from 3 to 6 hours under nitrogen atmosphere with the ylid reagent obtained on treating the dimethyl 2-oxoheptylphosphonate (XXXVI) (1 molar equivalent) with sodium hydride, preferably in a solvent such as anhydrous tetrahydrofuran at a temperature of about 0° C. for from 15 to 60 minutes under a nitrogen atmosphere, provides the 15-oxo-9-ketal (XXXVII) (from (XXXIII). (See Flowsheet B, below). Reduction of (XXXVII) with excess sodium borohydride in methanol at a temperature of about −5° C. to 15° C. under a nitrogen atmosphere for from 30 minutes to two hours, followed by saponification provides the 11-hydroxy-9-ketals (XXXVIII) as a mixture of 15-epimers, separable by chromatography. For pertinent literature examples of this sequence see the aforementioned references, and also U.S. Pat. No. 3,833,612 (May 29, 1973). Substitution of appropriate glycols for ethylene glycol (except when W is substituted with haloalkyl) in the syntheses described in the aforementioned references for the preparation of (XXXIII) or (XXXIV) provides the 9-ketals of this invention.

The required dimethyl 2-oxoheptylphosphonate (XXXVI) can be prepared from the ester IV (see Flowsheet A) by reaction with dimethyl methylphosphonate lithium salt (XXXV), by the method described by E. J. Corey and G. T. Kwintowski, *Journ. Amer. Chem. Soc.,* 88, 5654 (1966).

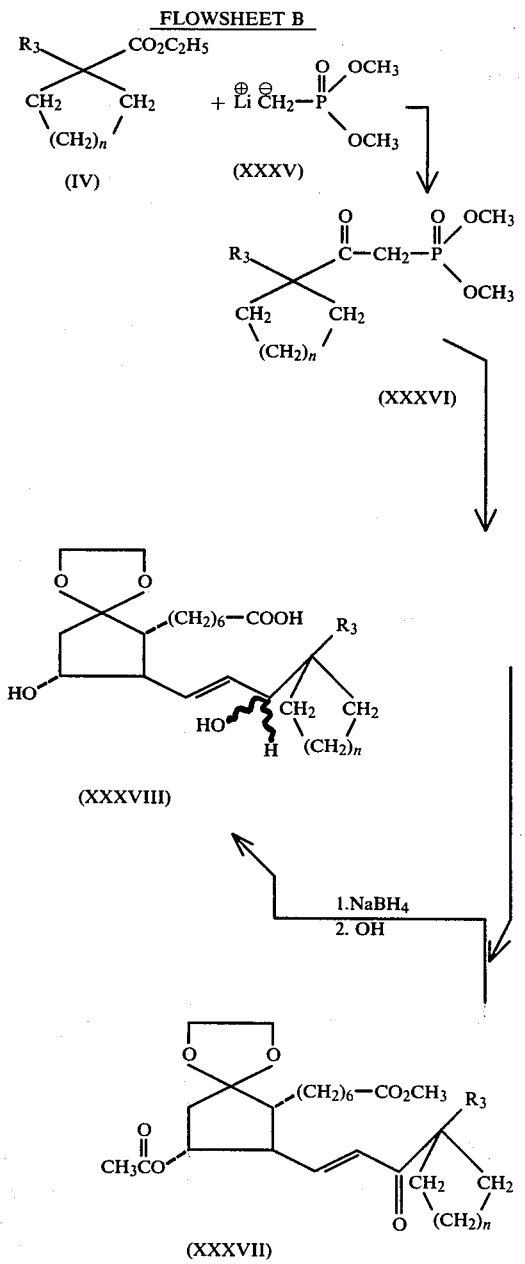

(XXXVIII)

(XXXVII)

The prostanoic and prostenoic carboxylic acids of this invention are convertible to the corresponding alkyl esters by treatment with the appropriate diazoalkane in the usual manner. The preparation of diazoalkanes by various procedures are well-described in the art, see for example C. D. Gutsche, *Organic Reactions,* VII, 389 (1954). Certain of the esters of this invention can also be obtained directly by use of the appropriate cyclopentenone ester (see XIII). The various esters can also be prepared by any of several procedures well-known in the art via an acid chloride (prior blocking of free alchohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydride is then treated with the appropriate alcohol to give the derivatized product. (For a pertinent literature analogy see *Prostaglandins,* 4, 738 (1973).)

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy see U.S. Pat. No. 3,821,279, June 28, 1974). A third procedure involves use of dicyclohexylcarbodiimide in the usual manner; for a pertinent literature analogy see German Offen. 2,365,205 (July 11, 1974); Chem. Abst., 81, 120098 g. (1974).

The esterified alcohol derivatives ($R_2$ is alkanoyloxy and/or $R_4$ is alkanoyl) are also prepared in the usual manner by procedures well-known in the art from the appropriate alkanoic acid anhydride or acid chloride.

Also embraced within the scope of this invention are the various intermediates, the use of which is described herein. These are represented by the following generic formulae: (G), (H), (K), (M), and (N), and wherein n and $R_3$ are as hereinabove defined and $R_{14}$ is a straight or branched chain alkyl group of from 1 to 7 carbon atoms, inclusive.

wherein M is a radical selected from the group consisting of

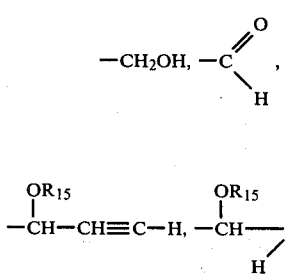

and wherein $R_{15}$ is hydrogen, tri-lower alkylsilyl (1 to 3 carbon atoms, inclusive), tetrahydropyranyl or α-lower alkoxy-lower alkyl.

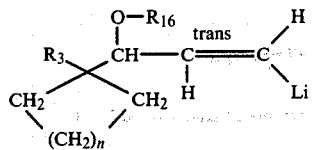

wherein R₃ and n are as hereinabove defined, and R₁₆ is tri-lower alkylsily, tetrahydropyanyl, or α-lower alkoxy-lower alkyl

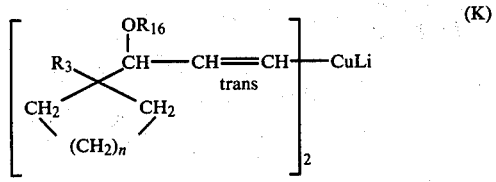

wherein R₃, R₁₆, and n are as hereinabove defined and its complexes with trialkyl (3 to 7 carbon atoms, inclusive) phosphines and the like.

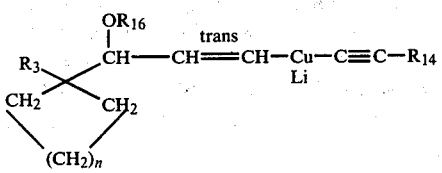

wherein R₃, R₁₄, R₁₆ and n are as hereinabove defined and its complexes with trialkyl (3 to 7 carbon atoms, inclusive)-phosphine or hexalower alkyl phosphonamides and the like.

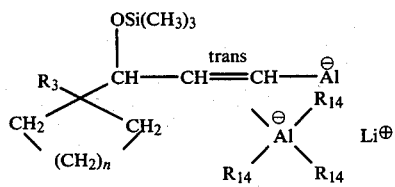

wherein R₃, R₁₄, and n are as hereinabove defined and each use of R₁₄ is not necessarily the same.

When the compounds of this invention are prepared from racemic starting compounds two racemates are obtained In appropriate instances these racemates can be separated from each other by careful application of the usual chromatographic procedures. In the more difficult instances it may be necessary to apply high pressure liquid chromatography including recycling techniques. [See G. Fallick, *American Laboratory*, 19–27 (August, 1973) as well as references cited therein. Additional information concerning high speed liquid chromatography and the instruments necessary for its application is available from Waters Associate, Inc., Maple St., Milford, Mass.].

It is also possible to prepare the individual enantiomers in the 11-oxy series via the conjugate addition procedure discussed above by starting with a resolved 4-oxycyclopentenone (see XIII, R'₂ is tetrahydropyranyloxy or tri-loweralkylsilyloxy) and a resolved β-chain precursor (see VII or VIII).

The 4-hydroxycyclopentenone racemates may be resolved into their component enantiomers (LIV) and (LV) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give (LVI), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (LIV) and (LV). A useful procedure for the resolution of a 4-hydroxycyclopentenone racemate via an oxime such as (LVI) is described in the art [R. Pappo, P. Collins and C. Jung, *Tetrahedron Letters*, 943 (1973)].

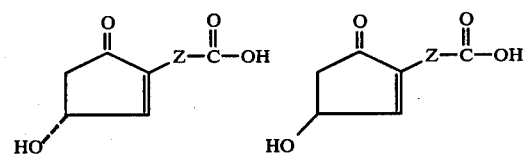

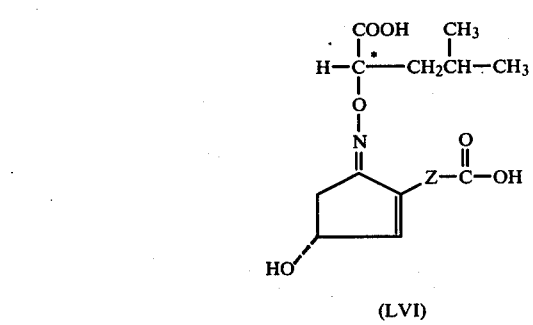

An alternative procedure for the preparation of the 4(R)-hydroxycyclopentenone enantiomers such as (LIV) involves as a key step the selective microbiological or chemical reduction of trione (LVII) to the 4(R)-hydroxycyclopentanedione (LVIII). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine)rhodium (I) tetrafluoroborate in the presence of one equivalent of organic base, such as triethylamine.

Conversion of hydroxycyclopentanedione (LVIII) to an enol ether or enol ester, (LIX, E=alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (LIX) with excess sodium bis(2-methoxyethoxy)aluminum hydride in a solvent such as tetrahydrofuran or toluene at low temperatures, such as −60° C. to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)hydroxycyclopentenone ester (LX). The ester (LX), after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih et al., *Journ. Amer. Chem. Soc.*, 95, 1676 (1973); J. B. Heather et al., *Tetrahedron Letters*, 2213 (1973); R. Pappo and P. W. Collins, *Tetrahedron Letters*, 2627 (1972) and R. Pappo, P. Collins, and C. Jung, *Ann. N.Y. Acad. Sci.*, 180, 64 (1971). For a descriptive of the baker's yeast procedure see C. J. Sih et al., *Journ. Amer. Chem. Soc.*, 94, 3643 (1972).

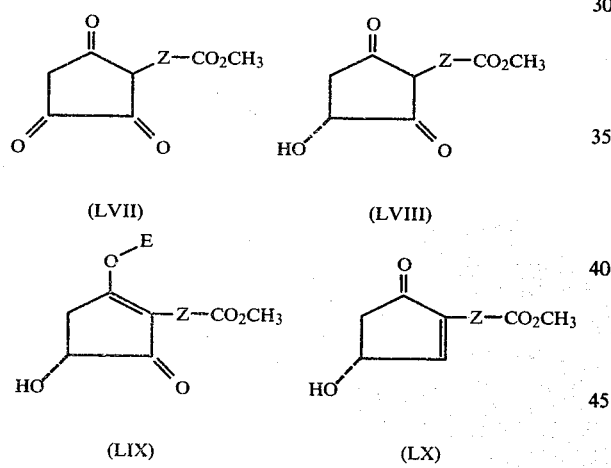

Procedures for the preparation of the requisite cyclopentanetriones (LVII) are well-established in the art and generally involve the treatment of an ω-1 oxo long chain ester (LXI) with methyl or ethyl oxalate and a base such as sodium methoxide in methanol, followed by treatment with dilute hydrochloric acid in aqueous methanol to effect the dealkoxalylation of the intermediate (LXII). See J. Kutsube and M. Matsui, *Agr. Biol. Chem.*, 33 1078 (1969); P. Collins, C. J. Jung and R. Pappo, *Israel Journal of Chemistry*, 6, 839 (1968); R. Pappo, P. Collins and C. Jung, *Ann. N.Y. Acad. Sci.* 180, 64 (1971); C. J. Sih et al., *Journ. Amer. Chem. Soc.*, 95, 1676 (1973) (see reference 7); and J. B. Heather et al., *Tetrahedron Letters*, 2313 (1973) for pertinent background literature.

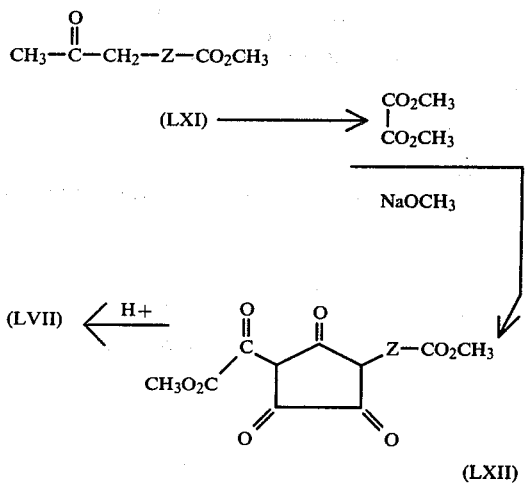

The intermediate keto esters (LXI) may be prepared by a variety of methods known to the art. One useful procedure is outlined below and involves alkylation of ethyl acetoacetate sodium salt (LXIII) in the usual manner with the appropriate side-chain precursor (LXIV, X=Cl, Br, I preferably Br or I) followed by decarbethoxylation and reesterification, all in the usual manner.

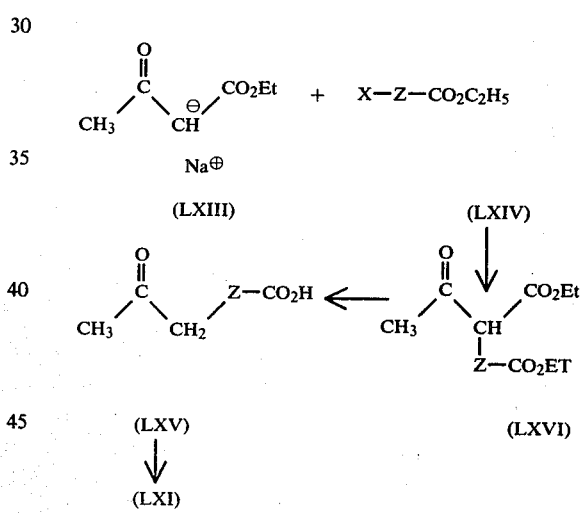

The side-chain precursors (LXIV) are commercially available where Z is —$(CH_2)_m$—, and can be prepared as described in Belgian Pat. No. 786,215 (granted and opened to inspection Jan. 15, 1973) where Z is

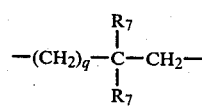

where Z is

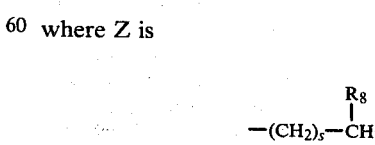

precursor (LXIV) can be prepared as indicated below by mono-tetrahydropyranylation of the diol (LXVII) to (LXVIII), followed by mesylation, treatment of the resulting mesylate (LXX) with the appropriately substituted sodio malonate to give (LXIX), decarbethoxylation and reesterification to (LXXI), mesylation of the second hydroxy function to (LXXIII) and displacement with lithium bromide (or iodide) to (LXXV). Alternatively, the ω-bromo alcohol (LXXIV) after blocking as the tetrahydropyranyl derivative (LXXII), on treatment with the substituted sodio malonate provides (LXIX).

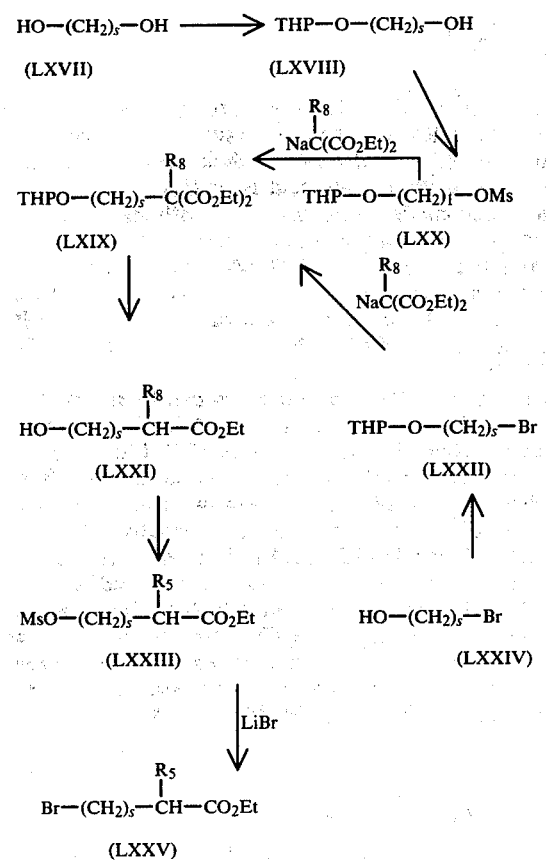

Those precursors wherein Z is —(CH$_2$)$_q$—O—CH$_2$— can be prepared by the transformation shown directly below starting with the mono-tetrahydropyranyl derivative (LXXVI). Thus, (LXXVI) is converted to the lithium alcoholate by treatment with butyl lithium, the alcoholate is then O-alkylated with ethyl bromoacetate to provide (LXXVII), which on de-O-tetrahydropyranylation, mesylation and reaction with lithium bromide gives the required (LXXX). (These and all the above-described transformations can be effected in the usual manner, well-established in the art; pertinent examples for most of the reactions can be found in the above-cited Belgian Pat. No. 786,215.)

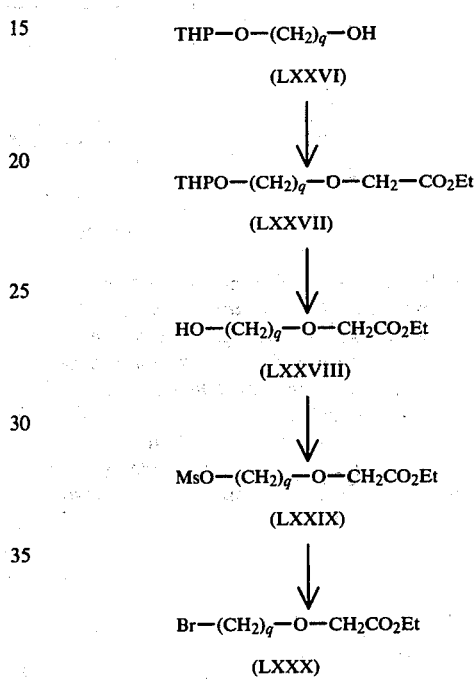

It is also possible to resolve the 4-hydroxycyclopentenone racemate (LXXXI) by microbiological means. Thus, treatment of the 4-O-alkanoyl or aroyl derivatives (LXXXII, R$_{18}$=aryl or alkyl) of racemate (LXXXI) (preferably the 4-O-acetyl and 4-O-propionyl derivatives) with an appropriate microorganism, preferably a Saccharomyces species e.g., 1375-143, affords preferential de-O-acylation of the 4(R)-enantiomer to give (LXXXIII), which is then separated from the unreacted 4(S)-O-acyl enantiomer (LXXXIV) by chromatographic procedures. After separation, mild hydrolysis of the 4(S) derivative (LXXXIV) provides the 4(S)-hydroxycyclopentenone (LXXXV). [See. N. J. Marscheck and M. Miyano, *Biochima et Biophysica Acta*, 316, 363 (1973) for related examples.]

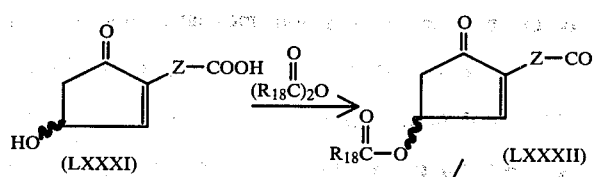

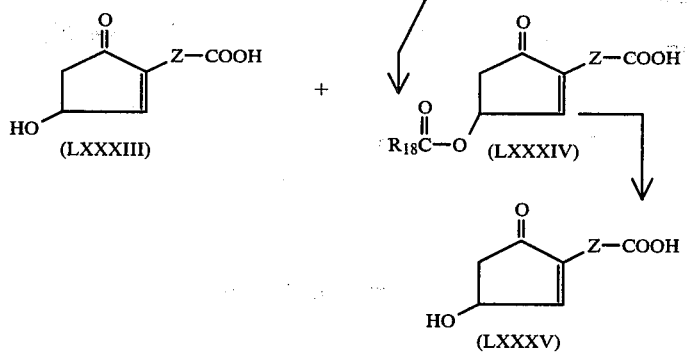

It is also possible to prepare the individual 4-hydroxycyclopentanenones (LXXXIII) and (LXXXV) directly by selective microbial hydroxylations of the corresponding 4-unsubstituted cycloptentenone (LXXXVI). For example, with *Aspergillus niger* ATCC 9142; a selective 4(R)-hydroxylation of (LXXXVI, Z=(CH$_2$)$_6$) has been reported; see S. Kurozumi, T. Tora and S. Ishimoto, *Tetrahedron Letters*, 4959 (1973). Other microorganisms can also accomplish this hydroxylation.

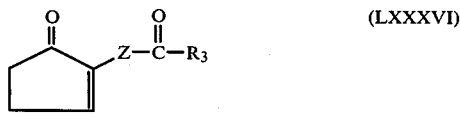

An alternative resolution procedure involves derivatization of the alcohol function of the racemic hydroxycyclopentenone to give ester-acid derivatives such as (LXXXVII) wherein R″$_1$ is hydrogen or an alkoxy group, n′ is zero or two and Z is as hereinabove defined.

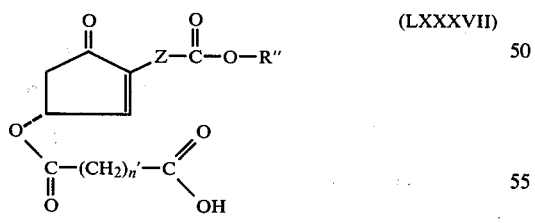

Such derivatives may be obtained from the corresponding free hydroxycyclopentenone by treatment in the usual manner with oxalyl chloride, succinyl chloride, succinic anhydride and the like. Treatment of the resulting acid or diacid (R″$_1$=hydrogen) with optically active amines e.g., 1-(−)-α-methylbenzylamine, d-(+)-α-methylbenzylamine, brucine, dehydroabietylamine, strychnine, quinine, cinchonine, qunidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(R)- and 4(S)-hydroxycyclopentenone enantiomers (LIV) and (LV) or their respective esters. Cleavage of the oxalate acid ester (LXXXVII, n=0) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); for an example of the use of a succinate acid-ester see B. Goffinet, Ger. Offen. 2,263,880; *Chem. Abstracts,* 79, 7815$_z$ (1973).

The racemic β-chain precursors can be resolved at either the acetylenic alcohol stage (VII, Flowsheet A) or the trans-vinyl iodide stage (see VIII, Flowsheet A) by a variety of methods well-known in the art. These methods will be illustrated below with the acetylenic alcohol (LXXXVIII), but they apply equally well to the trans-vinyl iodide (LXXXIX). Furthermore, the resolved acetylenic alcohols corresponding to (LXXXVIII) can be converted to the trans-vinyl iodides corresponding to (LXXXIX) or its derivatives as described hereinabove without racemization [see for an example, A. F. Kluge, K. G. Untch and J. H. Fried, *Journ. Amer. Chem. Soc.*, 94, 7827 (1972)].

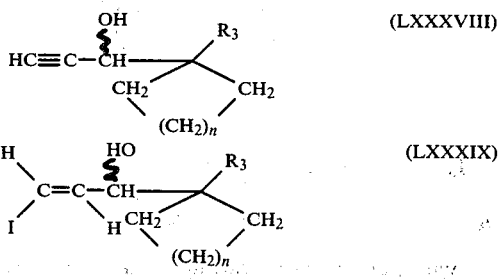

Racemates (LXXXVIII) or (LXXXIX) can be resolved by reverse phase and absorption chromatography on an optically active support system or by selective transformation of one isomer by microbiological or enzymatic procedures.

A more generally applicable procedure involves conversion of the racemic alcohol to a mixture of diastereomers by derivatization of the hydroxy function with an optically active reagent, followed by separation of the diastereomers by fractional crystallization or chromatographic procedures, as discussed hereinabove. Regeneration of the alcohol function from the individual diastereomer then provides the individual enantiomeric alcohols (XL) and (XLI).

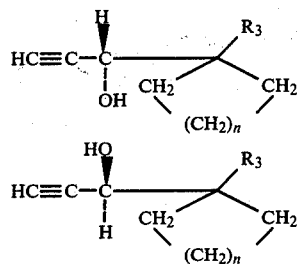

Useful derivatives for resolution purposes include the salts of the phthalate half acid ester (XLII) with an optically active amine (e.g., 1-(−)-α-methylbenzylamine, d-(+)-α-methylbenzylamine, brucine, dehydroabietylamine, strychnine, guinine, cinchonine, cinchonidine, quinidine, ephedrine, deoxyephedrine, amphetamine, (+)-2-amino-1-butanol, (−)-2-amino-1-butanol and the like).

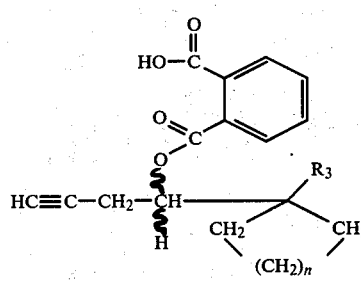

For the resolution in the art of the related 3-hydroxy-1-octyne by this procedure see J. Fried et al., *Annals of the N.Y. Acad. of Sci.*, 180, 38 (1971), and of the related 1-iodo-trans-1-octen-3-ol see A. F. Kluge, K. G. Untch and J. H. Fried, *Jour. Amer. Chem. Soc.*, 94, 7827 (1972).

Other useful derivatives are the diastereomeric carbamates (XLIII) obtained by treatment of racemate (LXXXVIII) with an optically active isocyanate (e.g., (+)-1-phenylethylisocyanate and (−)-1-phenylethylisocyanate).

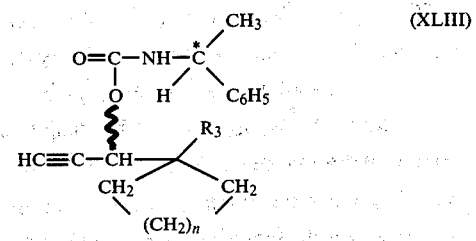

Various esters of racemate (LXXXVIII) with optically active acids are also useful for resolution purposes. Among the optically active acids which can be used in this connection are ω-camphoric acid, menthoxyacetic acid, 3α-acetoxy-Δ⁵-etianic acid, 3α-acetoxy-5,16-etiadienoic acid. (−)-α-methoxy-α-trifluoromethylphenylacetic acid [see (XLIV)] (+)-α-methoxy-α-trifluoromethylphenylacetic acid, and the like.

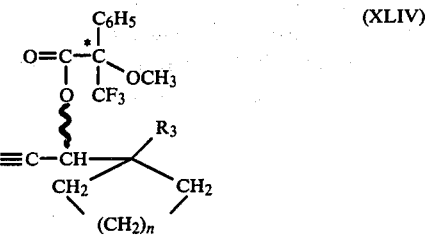

The resolution of the related 1-octyne-3-ol with 3β-acetoxy-Δ⁵-etianic acid and 3β-acetoxy-5,16-etiadienoic acid has been described in the art [see R. Pappo, P. Collins, and C. Jung, *Annals of the N.Y. Acad. of Sci.*, 180, 64 (1971)].

The preparation of the enantiomeric acetylenic alcohols or 3-hydroxy-trans-vinyl iodides can also be accomplished by microbial techniques, involving a selective de-esterification of 3-O-alkanoyl or aroyl derivatives (LXVI) followed by chromatographic separation of the free hydroxy enantiomer from the esterified enantiomer and hydrolysis of the non de-esterified ester. Useful microorganisms for this purpose are *Rhizopus arrhizus* and *Rhizopus nigricans* (ATCC 6227b).

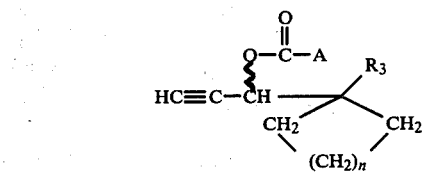

(XLV, A=alkyl, aryl)

Alternatively, it is possible to effect selective microbiological reduction of the corresponding 3-keto derivatives (XLVI) and (XLVII) to a single enantiomer, useful microorganisms for this purpose are *Penicillium decumbens* and *Aspergillus ustus*. Ketones (XLVI) and (XLVII) are readily obtainable by oxidation under mild conditions of the corresponding alcohols. For pertinent literature examples see J. B. Heather et al., *Tetrahedron Letters*, 2313 (1973). It is also possible to effect optically selective reduction of ketones

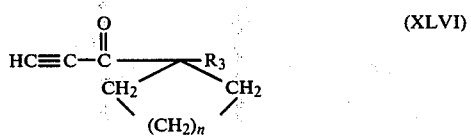

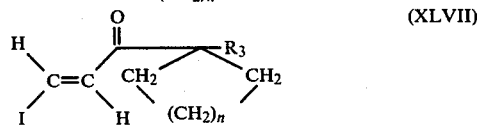

(XLVI) or (XLVII) by the use of an optically active reducing agent such as tri(+S-2-methylbutyl)aluminum etherate, lithium aluminum hydride-3-O-benzyl-1,2-O-cyclohexylidene-α-D-glucofuranose complex, and lithium hydrodipinan-3α-ylborate. For pertinent references to this procedure see R. A. Kretchmer *Journ. Org. Chem.* 37, 801 (1972); S. A. Landor et al., *Journ. Chem. Soc.* (C) 1822, 2280 (1966), ibid. 197 (1967); M. F. Grundon et al., ibid., 2557 (1971); and J. D. Morrison and H.

S. Mosher, "Assymetric Organic Reactions", pp. 160–218, Prentice-Hall, Englewood Cliffs, N.J. (1971).

Utilization of only a resolved β-chain or only a resolved hydroxycyclopentenone gives a mixture of diastereomers, which can then be separated by the usual procedures of crystallization and/or chromatography. If necessary, high speed liquid chromatography, including recycling techniques, can be applied.

The conjugate addition racemic products such as (XV), (XVI), (XXI), and (XXII) can also be resolved into their respective enantiomers by procedures well-known in the art, certan of which are illustrated below.

Resolution of a 9α-hydroxy racemate (the component enantiomers are illustrated by XLVIII) and IC below) may be accomplished by conversion of the racemate, wherein the $C_{11}$ and $C_{15}$ hydroxy functions have been preferentially blocked by tetrahydropyranyl or trialkylsilyl groups, (for example, by first derivatizing the two hydroxy functions in the corresponding 9-oxo derivative and then reducing the 9-carbonyl as described hereinabove), to the corresponding phthalate half acid-ester, deblocking the $C_{11}$ and $C_{15}$ hydroxy functions and conversion of the diacid (e.g., C) to a mixture of diastereomeric bis salts (e.g., CI) with an optically active amine (e.g., 1-(−)-α-methylbenzylamine, D-(+)-α-methylbenzylamine, brucine, dehydroabietylamine, strychnine, quinine, cinchonine, cinchonidine, quinidine, ephedrine, deoxyepedrine, amphetamine, (+)-2-amino-1-butanol, (−)-2-amino-1-butanol and the like). The resulting diastereomers are then separated by fractional crystallization and the individual components are then converted by acidification and saponification to the individual optically active parent 9α-hydroxy enantiomers (XLVIII) and (IC), oxidation of which, after preferential blocking of the $C_{11}$ and $C_{15}$ hydroxy functions with tetrahydropyranyl or trialkylsilyl groups, provides, after deblocking, the corresponding individual 9-oxo-enantiomers (CII) and (CIII). If necessary, the 11- and 15-hydroxy groups can be converted to tetrahydropyranyloxy groups prior to saponification of the phthalate ester. (For an appropriate literature procedure see E. W. Yankee, C. H. Lin and J. Fried. *Journ. Chem. Soc.*, 1972, 1120).

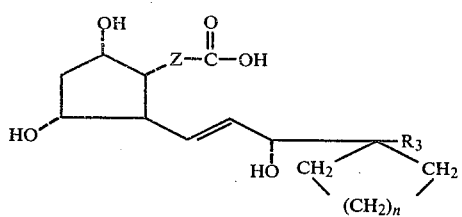
(XLVIII)

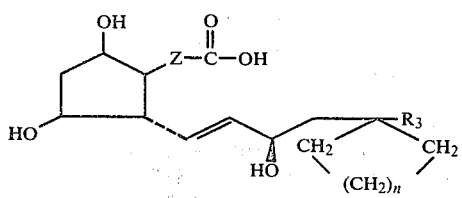
(IC)

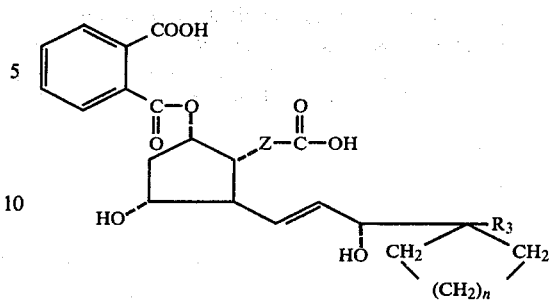
(C)

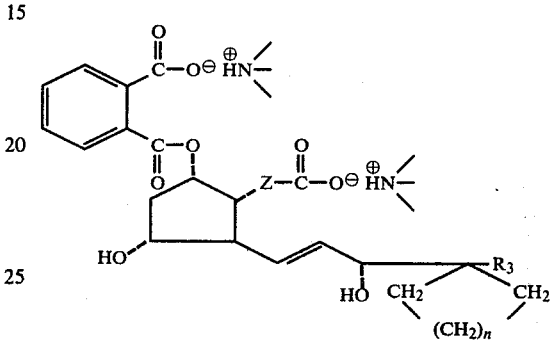
(CI)

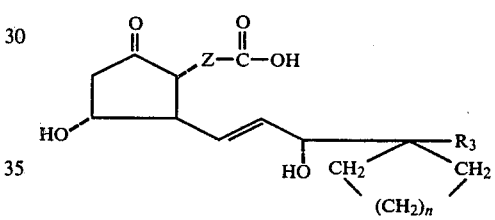
(CII)

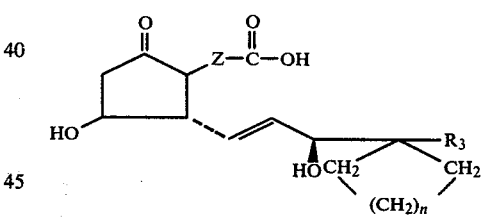
(CIII)

Another procedure involves conversion of the 9α-hydroxy racemate (as the prostenoic acid ester and with the $C_{11}$ and $C_{15}$ alcohol functions preferentially blocked as tetrahydropyranyl or trialkylsilyl ethers) to the diastereomeric carbamates with an optically active isocyanate, e.g., (+)-1-phenylethylisocyanate or (−)-1-phenylethylisocyanate, followed by deblocking. Separation of the resulting diastereomers, for example (CIV) and (CV), can be accomplished by fractional crystallization or by the usual chromatographic procedures, or if necessary by high speed liquid chromatography involving, if necessary, recycling techniques. Base-treatment of the individual diastereomeric carbamates affords the individual diastereomeric alcohols, for example (XLVIII) and (IC).

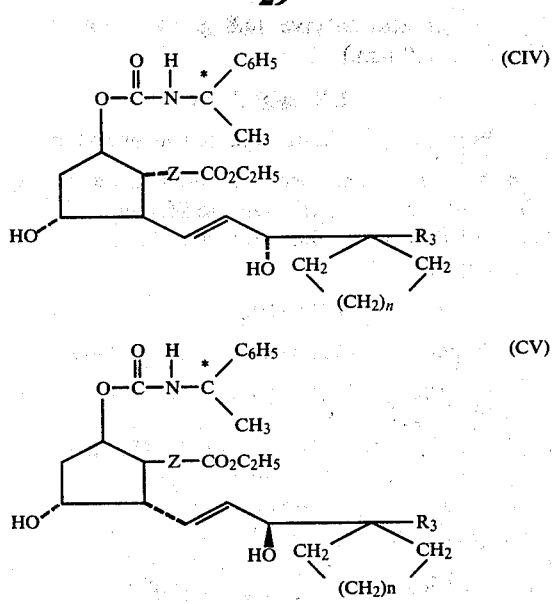

It is also possible to effect resolution of the 9α-hydroxy racemate, preferably as the prostenoate ester, by esterification of the 9α-hydroxy function (prior preferential blocking as discussed hereinabove of $C_{11}$ and $C_{15}$-hydroxy functions as tetrahydropyranyl or trialkylsilyl ethers) with an optically active acid, via its acid chloride followed by deblocking the $C_{11}$ and $C_{15}$ alcohol groups. Suitable optically active acids include ω-camphoric acid, menthoxyacetic acid, 3α-acetoxy-Δ$^5$-etianic acid, (−)-α-methoxy-α-trifluoromethylphenylacetic acid and (+)-α-methoxy-α-trifluoromethylphenylacetic acid, and the like. The resulting diastereomeric esters, for example, (CVI) and (CVII), are then separated by fractional crystallization or by chromatographic techniques including, if necessary, the use of high speed liquid chromatography. Saponification of the individual diastereomers then provides the individual 9α-hydroxyprostenoic acid enantiomers (XLVIII) and (IC).

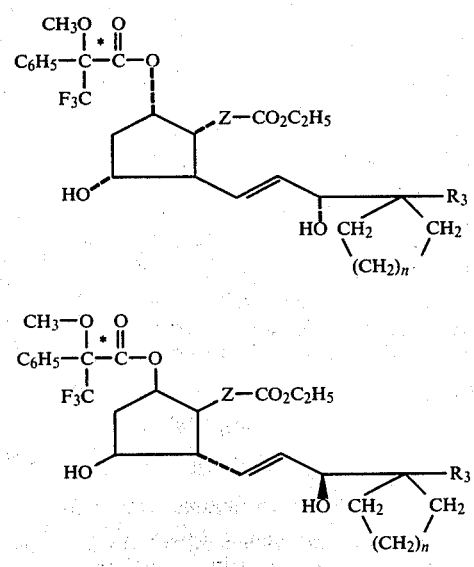

Although the above-described procedures are illustrated with examples having the 11α-hydroxy group, they apply as well to the members of the 11-deoxy series.

Another resolution procedure, less useful than the methods described above which are based on the 9α-hydroxy derivative, but which is particularly applicable to the 11-deoxy compounds of this invention, involves derivatization of the keto function of the 9-oxoprostenoic acid or ester racemate with the usual type of ketone derivatizing agents bearing an optically active center. The resulting mixture of diastereomeric derivatives can then be separated by fractional crystallization or by chromatography or, if necessary, by high speed liquid chromatography. The individual diastereomeric keto derivatives, for example (CVIII) and (CIX), are then convertible to the individual 9-oxo enantiomers, for example (CX) and (CXI), by any of the usual cleavage techniques, provided that they are sufficiently mild so as not to disturb the sensitive 11-hydroxy-9-keto system if it is present. (This latter point is not a problem with 11-unsubstituted derivatives.) Ketone reduction of the 9-oxo-enantiomer as described hereinabove then provides the corresponding 9α-hydroxy or 9α-hydroxy enantiomer. Among the optically active reagents useful for ketone derivatization are 1-α-aminoxy-γ-methylpentanoic acid hydrochloride [E. Testa et al., Helv. Chimica Acta, 47 (3), 766 (1973)], menthylhydrazine, and 4-α-methylbenzylsemicarbazide. A useful procedure for the cleavage of oximes such as (CVIII) and (CIX) involves treatment of the oxime at about 60° C. for about 4 hours in 1:2 aqueous-tetrahydrofuran buffered with ammonium acetate and containing titanium trichloride.

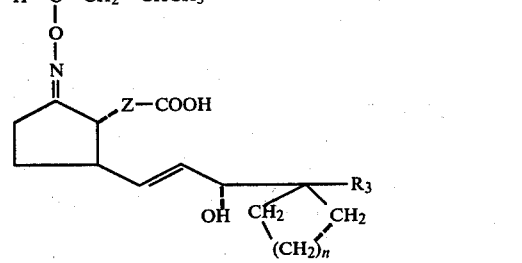

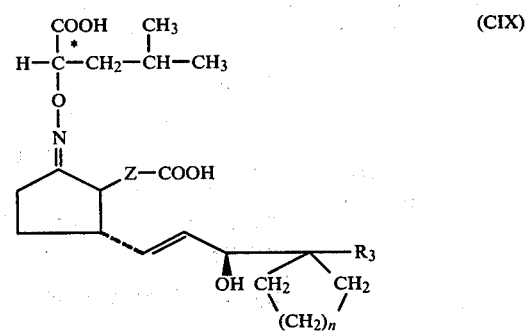

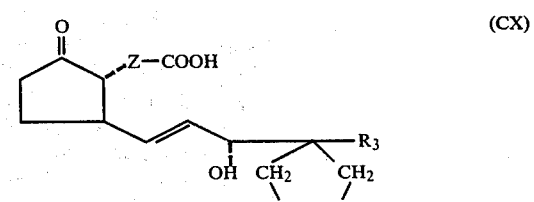

-continued

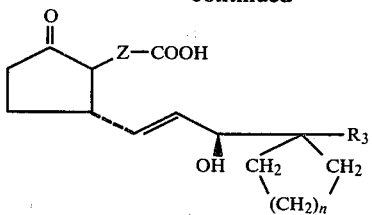

(CXI)

Other useful ketone derivatizing agents are optically active 1,2,-glycols, e.g., D(—)-2,3-butanediol, or 1,2-dithiols, e.g., L(+)-2,3-butanedithiol. These are used to convert the 9-oxo racemate to 9,9-alkylenedioxa or 9,9-alkylenedithia diastereomers. Separation of diastereomers by chromatographic procedures, followed by regeneration of the individual 9-oxo enantiomer by ketal cleavage can be accomplished by procedures well-known in the art. Both ketalization and deketalization would have to be accomplished by procedures which would not disrup the 11-oxo-9-keto system, which of course, is not a problem in the 11-unsubstituted series.

The invention will be described in greater detail in conjunction with the following specific examples.

EXAMPLE 1

Preparation of ethyl 2,2-trimethylenehexanoate

To a stirred solution of 27.6 g. of freshly distilled N-isopropylcyclohexylamine in 200 ml. of dry tetrahydrofurane cooled to −78° C. is added at a fast rate 96 ml. of 2.04 molar n-butyllithium in hexane. To the resulting solution is added dropwise 25 g. of ethyl cyclobutanecarboxylate. After 30 minutes the resulting solution is allowed to warm to ambient temperature and is transferred to a dropping funnel under nitrogen and is added dropwise over a period of 1¼ hours to a solution of 54 g. of n-butyl iodide in 100 ml. of dry dimethylsulfoxide maintaining the temperature at 16°-20° C. Stirring is continued for an additional 30 minutes. The separated salts are removed by filtration and the mother liquor is taken to a small volume and the resulting oil is diluted with hexanes. This solution is washed with 2% hydrochloric acid, saturated sodium chloride solution, and dried with anhydrous magnesium sulfate. The solvent is removed and the residual oil is distilled to give 14.6 g. (41%) of product, b.p. 84°-87° C. (10 mm.).

EXAMPLE 1a

Preparation of ethyl 2,2-tetramethylenehexanoate

In the manner described in Example 1, treatment of the lithium salt of ethyl cyclopentanecarboxylate with n-butyl iodide furnishes the subject product.

EXAMPLE 2

Preparation of 2,2-trimethylenehexan-1-ol

To a stirred solution of 20 g. of ethyl 2,2-trimethylenehexanoate (Example 1) in 100 ml. of dry toluene in an argon atmosphere and cooled in an ice bath is added dropwise 250 ml. (2 molar equivalents) of 0.89 molar diisobutylaluminum hydride in toluene. The resulting solution is stirred at ambient temperature for 2 hours and then poured into excess iced 5% hydrochloric acid. The organic phase is separated and washed with 5% hydrochloric acid, saturated sodium chloride solution, dried with anhydrous magnesium sulfate and taken to dryness to give 14.8 g. (98%) of oil; b.p. 92°-93° C. (10 mm.).

EXAMPLE 2a

Preparation of 2,2-tetramethylenehexan-1-ol

In the manner described in Example 2, treatment of ethyl 2,2-tetramethylenehexanoate (Example 1a) with 0.89 molar diisobutylaluminum hydride furnishes the subject product.

EXAMPLE 3

Preparation of 2,2-trimethylenehexaldehyde

Chromium trioxide (61.5 g.), dried in a vacuum desiccator over phosphorous pentoxide, is added to an ice cold solution of 97 g. of dry pyridine in one liter of dry methylene chloride. The deep red suspension is stirred for 15 minutes at 0° C. and then for 45 minutes at ambient temperature. A solution of 14.5 g. of 2,2-trimethylenehexanol-1 (Example 2) in 55 ml. of methylene chloride is added all at once to the suspension. A black tarry deposit is formed immediately. After stirring at ambient temperature for 15 minutes the solution is decanted from the tarry deposit which is then triturated four times with small portions of methylene chloride. The combined extracts are washed twice with ice cold 5% sodium hydroxide, ice cold 5% hydrochloric acid and finally with saturated sodium chloride solution, dried with magnesium sulfate and taken to dryness. Distillation gives 12.9 g. of product; b.p. 69° C. (11 mm.).

EXAMPLE 3a

Preparation of 2,2-tetramethylenehexaldehyde

Oxidation of 2,2-tetramethylenehexan-1-ol (Example 2a) with chromium trioxide-pyridine complex in the manner described in Example 3 furnishes the subject product.

EXAMPLE 4

Preparation of 4,4-trimethylene-1-octyn-3-ol

To a solution of lithium acetylide-ethylenediamine complex (9.4 g.) in 90 ml. of dry dimethylsulfoxide cooled in an ice bath is added 12.94 g. of 2,2-trimethylenehexaldehyde (Example 3) in 10 ml. of dimethylsulfoxide dropwise at such a rate that the temperature is maintained 20°-25° C. The solution is stirred at ambient temperature for 12 hours and then poured into a mixture of ice cold 2% hydrochloric acid and ether. The ether layer is separated and the aqueous phase is extracted with ether. The combined ether extracts are washed with saturated sodium chloride solution, dried with anhydrous magnesium sulfate and taken to dryness. Distillation provides 13.53 g. of product, b.p. 108°-109° C. (13 mm.).

EXAMPLE 4a

Preparation of 4,4-tetramethylene-1-octyn-3-ol

Treatment of 2,2-tetramethylenehexaldehyde (Example 3a) with lithium acetylide-ethylenediamine complex in dimethylsulfoxide in the manner described in Example 4 is productive of the subject compound.

EXAMPLE 5

Preparation of 4,4-trimethylene-3-trimethylsilyloxy-1-octyne

To a stirred solution of 5.3 g. of 4,4-trimethylene-1-octyn-3-ol (Example 4) and 5.42 g. of imidazole in 32 ml. of dry dimethylformamide, cooled in an ice bath under argon atmosphere is added 4.35 g. of chlorotrimethylsilane. After stirring at 0° C. for 15 minutes, the solution is stirred at ambient temperature for 18 hours and then poured into 200 ml. of hexanes. The solution is washed twice with ice cold water, saturated sodium chloride solution, dried with anhydrous magnesium sulfate and taken to dryness. Distillation furnishes 6.02 g. (80%) of colorless oil, b.p. 110°–112° C. (14 mm.).

EXAMPLE 5a

Preparation of 4,4-tetramethylene-3-trimethylsilyloxy-1-octyne

Treatment of 4,4-tetramethylene-1-octyn-3-ol (Example 4a) with chlorotrimethylsilane in dimethylformamide containing imidazole as described in Example 5 furnishes the subject product.

EXAMPLE 5b

Preparation of 1-iodo-4,4-trimethylene-3-trimethylsilyloxy-1-octyne

To a solution of 25 g. of 4,4-trimethylene-3-trimethylsilyloxy-1-octyne (Example 5), stirred under argon atmosphere at −78° C. is added dropwise 93 ml. of 2.3 M n-butyllithium in hexane at a rate to maintain the temperature below −40° C. After stirring for 40 minutes, a solution of iodine in ether is added until a purple color persists. The solution is allowed to warm to ambient temperature and 10% aqueous sodium thiosulfate solution is added until purple color is removed. The organic phase is washed with dilute aqueous sodium thiosulfate solution, saturated sodium chloride solution, dried with anhydrous sodium sulfate and taken to dryness to afford the subject product as an oil.

EXAMPLE 5c

Preparation of 1-iodo-4,4-trimethylene-3-trimethylsilyloxy-1-cis-octene

To a solution of 30 g. of 1-iodo-4,4-trimethylene-3-trimethylsilyloxy-1-octyne (Example 5a) in 100 ml. of methanol, under argon atmosphere is added 54 g. of potassium azodicarboxylate [J. Thiele, Annalen der Chemie, 271 127 (1892)]. To this solution is added dropwise 45 ml. of acetic acid over a period of about 2 hours. The solids are removed by filtration and the mother liquor is reduced to a small volume, diluted with water and extracted with ether. The ether is evaporated and the residual oil is stirred with 250 ml. of 1 M sodium bicarbonate solution. The solution is extracted several times with ether and the combined extracts are washed with saturated sodium chloride solution, dried with anhydrous sodium sulfate and taken to dryness to furnish the subject product as an oil.

EXAMPLE 6

Preparation of 1-iodo-4,4-trimethylene-3-trimethylsilyloxy-1-trans-octene

To a mixture of 4.76 g. of sodiumborohydride and 23.6 g. of 2-methyl-2-butene in 220 ml. of dry tetrahydrofuran at −5° C. is added dropwise 23.8 g. of freshly distilled borontrifluoride etherate. The resulting mixture is stirred at −5° C. to −0° C. for 2 hours and to it is added dropwise a solution of 20 g. of 4,4-trimethylene-3-trimethylsilyloxy-1-octyne (Example 5) in 20 ml. of dry tetrahydrofuran. The resulting mixture is stirred at ambient temperature for 2½ hours. The mixture is then cooled to −5° C. and there is added 44 g. of trimethylene oxide portionwise over a period of 20 minutes, maintaining the temperature at 15°–20° C. The mixture is stirred at ambient temperature for 2 hours and then poured simultaneously, with a solution of 119 g. of iodine in 290 ml. of tetrahydrofuran, into 1490 ml. of 15% aqueous sodium hydroxide solution. After stirring for 30 minutes the organic phase is separated and the aqueous phase is extracted with ether. The combined organic phase is washed with 5% aqueous sodium thiosulfate solution, saturated sodium chloride solution, dried with anhydrous magnesium sulfate and taken to dryness to give 27 g. of oily material. Chromatography on 135 g. of florisil and eluting with 500 ml. of hexanes furnishes 24 g. of oily product which is shown to be contaminated with starting material and iodoform by infrared and thin layer chromatography. The material is purified by removing the trimethylsilyl group in the following manner. The crude product is dissolved in 350 ml. of acetic acid-tetrahydrofuran-water (4:2:1) by stirring at ambient temperature for 5 minutes. The solvent is removed under reduced pressure and the residual oil containing mainly 1-iodo-3-hydroxy-4,4-trimethylene-1-trans-octene is applied to a 2″ (flat) dry column containing 1200 g. of Woelm silica gel. The column is developed with benzene, cut into 1 inch segments and each segment is eluted with chloroform. Combination of the appropriate fractions affords 300 mg. of iodomethane, 2.8 g. of 4,4-trimethylene-1-octyne-3-ol, and 11.6 g. of 1-iodo-3-hydroxy-4,4-trimethylene-1-trans-octene. Silylation of this material in the manner described above followed by distillation of the residual oil furnishes 13 g. of pure product, b.p. 83°–84° C. (0.2 mm.).

EXAMPLE 6a

Preparation of 1-iodo-4,4-tetramethylene-3-trimethylsilyloxy-1-trans-octene

Treatment of 4,4-tetramethylene-3-trimethylsilyloxy-1-octyne (Example 5a) in the manner described in Example 6 furnishes the subject product.

EXAMPLE 7

Preparation of ethyl 15-hydroxy-9-oxo-16,16-trimethylene-13-trans-prostenoate and ethyl 15-epi-hydroxy-9-oxo-16,16-trimethylene-13-trans-prostenoate To a solution of 5 g. of 1-iodo-4,4-trimethylene-3-trimethylsilyloxy-1-trans-octene (Example 6) in 5 ml. of hexanes, cooled to −78° C. in an argon atmosphere is added 40 ml. of 0.75 N tertiary butyllithium in pentane. After stirring for 35 minutes, the solution is allowed to warm to −5° C. and stirred for an additional 1 hour. The solution containing 4,4-trimethylene-3-trimethylsilyloxy-1-trans-octenyl lithium is cooled to −78° C. and there is added a solution of 1.79 g. of copper pentyne in 5.5 ml. of hexamethylphosphorous triamide and 50 ml. of dry ether. The solution is stirred at −78° C. for 1 hour. To this solution containing lithio pentynyl-(4,4-trimethylene-3-trimethylsilyloxy-1-trans-octenyl) cuprate is added 3.26 g. of 2-(6-carbethoxyhexyl)cyclopent-2-en-1-one [Bernady, K. F., Pletto, J. P. and Weiss, M. J., U.S. Pat. No. 3,836,581 (1974)] in 30 ml. of ether. The solution is stirred at −15° C. for 1 hour then at 0° C. for 1 hour, then poured into 600 ml. of saturated ammonium chloride solution and 200 ml. of ether and stirred for 20 minutes. The ether layer is separated and the aqueous layer is extracted twice with ether. The combined ether extracts are washed with water, dried with anhydrous magnesium sulfate and taken to dryness. The residual oil is dissolved in a small amount of ice cold hexanes, filtered from solids and taken to dryness to furnish 8 g. of ethyl 9-oxo-16,16-trimethylene-15-trimethylsilyloxy-13-trans-prostenoate as an oil. The trimethylsilyl group is removed by treating the oil with 125 ml. of acetic acid-tetrahydrofuran-water (4:2:1) at ambient temperature for 10 minutes and then removing the solvents to afford 5.63 g. of ethyl 15-hydroxy-9-oxo-16,16-trimethylene-13-trans-prostenoate. The oil is applied to a dry column (2" flat) using 950 g. of silica gel and developed with ethyl acetate-benzene (1:4) to furnish 2.16 g. of ethyl 15-hydroxy-9-oxo-16,16-trimethylene-13-transprostenoate and 1.37 g. of ethyl 15-epi-hydroxy-9-oxo-16,16-trimethylene-13-trans-prostenoate.

EXAMPLE 7a

Preparation of ethyl 15-hydroxy-9-oxo-16,16-trimethylene-13-trans-prostenoate and ethyl 15-epi-hydroxy-9-oxo-16,16-trimethyl-13-trans-prostenoate To a solution containing 4,4-trimethylene-3-trimethylsilyloxy-1-trans-octenyl lithium, prepared from 2.86 g. of 1-iodo-4,4-trimethylene-3-trimethylsilyloxy-1-trans-octene (Example 6) in the manner described in Example 7 above, is added 4.07 ml. of 1.92 M trimethylaluminum in hexane at −5° C., and the resulting solution is stirred for 15 minutes.

To the above solution containing lithio trimethyl-(4,4-trimethylene-3-trimethylsilyloxy-1-trans-octenyl alanate is added a solution of 1.86 g. of 2-(6-carbethoxyhexyl)cyclopent-2-en-1-one in 7 ml. of ether at −5° C. The mixture is stirred at 0° C. for 1 hour and 25° C. for 20 hours diluted with ether and poured into a stirred mixture of 140 g. of ice and 5.2 ml. of 37% hydrochloric acid. The aqueous phase is separated and extracted with ether. The combined ether phases are washed with water, saturated sodium chloride solution, dried with anhydrous magnesium and taken to dryness to give ethyl 9-oxo-16,16-trimethylene-15-trimethylsilyloxy-13-trans-prostenoate as an oil. Hydrolytic removal of the trimethylsilyl group followed by dry column chromatography in the manner described in Example 7 furnishes the subject products.

EXAMPLE 7b

Preparation of ethyl 15-hydroxy-9-oxo-16,16-trimethylene-13-trans-prostenoate and ethyl 15-epi-hydroxy-9-oxo-16,16-trimethylene-13-trans-prostenoate To a solution containing 4,4-trimethylene-3-trimethylsilyloxy-1-trans-octenyl lithium prepared from 413 mg. of 1-iodo-4,4-trimethylene-3-trimethylsilyloxy-1-trans-octene (Example 6) in the manner described in Example 7 above is added a solution of 165 mg. of tri-n-butylphosphine-cuprous iodide complex in 1.3 ml. of dry ether at 78° C. and the resulting solution is stirred at −78° C. for 1 hour.

To the above solution containing lithio-bis-[4,4-trimethylene-3-(trimethylsilyloxy)-1-trans-octenyl]cuprate is added a solution of 165 mg. of 2-(6-carbethoxyhexyl)cyclopent-2-en-1-one in 2 ml. of ether. The resulting solution is stirred at −78° C. for 30 minutes and −5° C. for 1 hour and poured into water. The solution is extracted with ether and the extract is washed with saturated ammonium sulfate solution, brine, dried with magnesium and taken to dryness to furnish an oil. Removal of the trimethylsilyl group followed by dry column chromatography in the manner described in Example 7 furnishes the subject products.

EXAMPLE 8

Preparation of 9-oxo-15-hydroxy-16,16-trimethylene-13-transprostenoic acid

A solution of 500 mg. of d,1-ethyl 9-oxo-15-hydroxy-16,16-trimethylene-13-trans-prostenoate (Example 7) in 20 ml. of methanol-water (1:1) containing 336 mg. of potassium hydroxide is stirred at the reflux temperature under argon atmosphere for 2 hours. The cooled solution is extracted with ether and the aqueous phase is acidified in the cold with diluted hydrochloride acid. The solution is extracted with ether and the extract is washed with saturated sodium chloride solution, dried with anhydrous magnesium and taken to dryness to furnish 421 mg. of product as an oil.

EXAMPLE 9

Preparation of 9-oxo-15-epi-hydroxy-16,16-trimethylene-13-transprostenoic acid

According to the procedure described in Example 8, treatment of 500 mg. of d,1-ethyl 9-oxo-15-epi-hydroxy-16,16-trimethylene-13-trans-prostenoate with 20 ml. of methanol-water (1:1) containing 336 mg. of potassium hydroxide furnished 422 mg. of product as an oil.

EXAMPLE 10-15

Alkylation of the lithium salt of ethyl cyclobutanecarboxylate with the alkyl halides listed in the table below by the procedure described in Example 1 furnishes the 2,2-trimethylene esters of the table.

TABLE I

| Example | Alkyl halides | Product 2,2-trimethylene esters |
|---|---|---|
| 10 | propyl iodide | ethyl 2,2-trimethylenepentanoate |
| 11 | amyl iodide | ethyl 2,2-trimethyleneheptanoate |
| 12 | hexyl iodide | ethyl 2,2-trimethyleneoctanoate |
| 13 | benzyl iodide | ethyl 2,2-trimethylene-3-phenylpropionate |

TABLE I-continued

| Example | Alkyl halides | Product 2,2-trimethylene esters |
|---|---|---|
| 14 | 2-cyclopentyl-1-ethyl bromide | ethyl 2,2-trimethylene-4-cyclopentylbutyrate |
| 15 | 1-chloro-2-butyne | ethyl 2,2-trimethylene-4-hexnoate |

EXAMPLES 16–21

Reduction of the various esters listed in Table II below with diisobutylaluminum hydride all in the manner described in Example 2 above is productive of the alcohols of the table.

TABLE II

| Example | Starting esters of Example | Product Alcohols |
|---|---|---|
| 16 | 10 | 2,2-trimethylenepentan-1-ol |
| 17 | 11 | 2,2-trimethyleneheptan-1-ol |
| 18 | 12 | 2,2-trimethyleneoctan-1-ol |
| 19 | 13 | 2,2-trimethylene-3-phenylpropan-1-ol |
| 20 | 14 | 2,2-trimethylene-4-cyclopentylbutan-1-ol |
| 21 | 15 | 2,2-trimethylene-4-hexyn-1-ol |

EXAMPLES 22–27

Oxidation of the alcohols listed in the table below with chromium trioxide-pyridine complex by the procedure described in Example 3 above furnishes the corresponding aldehydes of the table.

TABLE III

| Ex. | Starting alcohols of Example | Product 2,2-trimethylenealdehydes |
|---|---|---|
| 22 | 16 | 2,2-trimethylenevaleraldehyde |
| 23 | 17 | 2,2-trimethyleneheptaldehyde |
| 24 | 18 | 2,2-trimethyleneoctaldehyde |
| 25 | 19 | 2,2-trimethylene-3-phenylpropionylaldehyde |
| 26 | 20 | 2,2-trimethylene-4-cyclopentylbutyraldehyde |
| 27 | 21 | 2,2-trimethylenehex-4-yn-1-al |

EXAMPLES 28–33

Treatment of the various aldehydes listed below in Table IV with lithium acetylide-ethylenediamine complex in the manner described in Example 4 furnishes the hydroxyacetylenes of the table.

TABLE IV

| Ex. | Starting aldehydes of Example | Product hydroxyacetylenes |
|---|---|---|
| 28 | 22 | 4,4-trimethylene-1-heptyn-3-ol |
| 29 | 23 | 4,4-trimethylene-1-nonyn-3-ol |
| 30 | 24 | 4,4-trimethylene-1-decyn-3-ol |
| 31 | 25 | 4,4-trimethylene-5-phenyl-1-pentyn-3-ol |
| 32 | 26 | 4,4-trimethylene-6-cyclopentyl-1-hexyn-3-ol |
| 33 | 27 | 4,4-trimethylene-1,6-octadiyn-3-ol |

EXAMPLES 34–39

Treatment of the various alcohols listed below in Table V with chlorotrimethylsilane in the manner described in Example 5 furnishes the corresponding trimethylsilyloxy acetylenes of the table.

TABLE V

| Example | Starting alcohols of Example | Product trimethylsilyloxyacetylenes |
|---|---|---|
| 34 | 28 | 4,4-trimethylene-3-trimethylsilyloxy-1-heptyne |
| 35 | 29 | 4,4-trimethylene-3-trimethylsilyloxy-1-nonyne |
| 36 | 30 | 4,4-trimethylene-3-trimethylsilyloxy-1-decyne |
| 37 | 31 | 4,4-trimethylene-3-trimethylsilyloxy-5-phenyl-1-pentyne |
| 38 | 32 | 4,4-trimethylene-3-trimethylsilyloxy-6-cyclopentyl-1-hexyne |
| 39 | 33 | 4,4-trimethylene-3-trimethylsilyloxy-1,6-octadiyne |

EXAMPLES 40–45

In the manner described in Example 6, treatment of the various acetylenes of Table VI below with disiamylborane, made in situ from sodium borohydride and 2-methyl-2-butene, followed by oxidation of the so formed organoborane with trimethylamine oxide followed by treatment of this product with iodine and sodium hydroxide furnishes the trimethylsilyliodovinylcarbinols of the table.

TABLE VI

| Example | Starting acetylenes of Example | Product trimethylsilylvinylcarbinols |
|---|---|---|
| 40 | 34 | 1-iodo-4,4-trimethylene-3-trimethylsilyloxy-1-trans-heptene |
| 41 | 35 | 1-iodo-4,4-trimethylene-3-trimethylsilyloxy-1-trans-nonene |
| 42 | 36 | 1-iodo-4,4-trimethylene-3-trimethylsilyloxy-1-trans-decene |
| 43 | 37 | 1-iodo-4,4-trimethylene-3-trimethylsilyloxy-5-phenyl-1-trans-pentene |
| 44 | 38 | 1-iodo-4,4-trimethylene-3-trimethylsilyloxy-6-cyclopentyl-1-trans-hexene |
| 45 | 39 | 1-iodo-4,4-trimethylene-3-trimethylsilyloxy-1-trans-octen-6-yne |

EXAMPLE 46

Preparation of ethyl 2,2-trimethylene-4-cis-hexenoate

A solution of 5 g. of ethyl 2,2-trimethylene-4-hexynoate (Example 15) in 40 ml. of dry pyridine is hydrogenated in a Parr apparatus using 600 mg. of 5% palladium on barium sulfate. After 1 hour when hydrogen uptake in complete, the solution is filtered thru celite and the mother liquor is taken to dryness to furnish 4 g. of product as an oil.

EXAMPLE 47–124

The product ethyl 15-hydroxy-9-oxo-16,16-trimethylene-13-trans-prostenoates of Table VII below are obtained by the procedure described in Example 7. In accordance with the process described therein, the starting trimethylsilyloxy substituted 1-iodo-1-trans-alkenes listed in Table 7 are treated with t-butyllithium providing the corresponding trimethylsilyl substituted trans-1-alkenyl lithium derivatives which on treatment with cuprous pentyne furnish the corresponding lithio pentynyl (trimethylsilyl substituted trans-1-alkenyl)cuprates, which in turn are treated with the cyclopent-2-en-1-ones listed in the table below. The resulting trimethylsilyl substituted 9-oxo-13-trans-prostenoic acid ethyl esters are hydrolyzed with acetic acid:tetrahydrofuran:water, and the resulting epimeric mixtures are separated, by dry column chromatography as described in Example 7 above, into their respective $C_{15}$ epimers listed in the table below.

TABLE VII

| Example | Starting cyclopentenone | Starting 1-iodo-1-trans-alkene of Example | Product Alkyl 9-oxo-13-trans-prostenoate and the corresponding 15-epimer |
|---|---|---|---|
| 47 | 2-(5-carbethoxypentyl)-cyclopent-2-en-1-one[a] | 6 | ethyl 15-hydroxy-9-oxo-16,16-trimethylene-7-nor-13-trans-prostenoate |
| 48 | 2-(7-carbethoxyheptyl)-cyclopent-2-en-1-one[a] | 6 | ethyl 15-hydroxy-9-oxo-16,16-trimethylene-7a-homo-13-trans-prostenoate |
| 49 | 2-(8-carbethoxyoctyl)-cyclopent-2-en-1-one[a] | 6 | ethyl 15-hydroxy-9-oxo-16,16-trimethylene-7a,7b-bishomo-13-trans-prostenoate |
| 50 | 2-(6-carbethoxy-6-methylhexyl)cyclopent-2-en-1-one[a] | 6 | ethyl 15-hydroxy-2-methyl-9-oxo-16,16-trimethylene-13-trans-prostenoate |
| 51 | 2-(6-carbethoxy-6-ethylhexyl)cyclopent-2-en-1-one[a] | 6 | ethyl 2-ethyl-15-hydroxy-9-oxo-16,16-trimethylene-13-trans-prostenoate |
| 52 | 2-(6-carbethoxy-5,6-trans-methanohexyl)-cyclopent-2-en-1-one (Example 745) | 6 | ethyl 15-hydroxy-2,3-trans-methano-9-oxo-16,16-trimethylene-13-trans-prostenoate |
| 53 | 2-(6-carbethoxy-5,5-dimethylhexyl)cyclopent-2-en-1-one[a] | 6 | ethyl 15-hydroxy-3,3-dimethyl-9-oxo-16,16-trimethylene-13-trans-prostenoate |
| 54 | 2-(6-carbethoxy-5-oxahexyl)cyclopent-2-en-1-one[a] | 6 | ethyl 15-hydroxy-3-oxa-9-oxo-16,16-trimethylene-13-trans-prostenoate |
| 55 | 2-(6-carbethoxy-5-thiahexyl)cyclopent-2-en-1-one[a] | 6 | ethyl 15-hydroxy-9-oxo-3-thia-16,16-trimethylene-13-trans-prostenoate |
| 56 | 2-(6-carbethoxy-6-phenylhexyl)cyclopent-2-en-1-one[a] | 6 | ethyl 15-hydroxy-9-oxo-2-phenyl-16,16-trimethylene-13-trans-prostenoate |
| 57 | 2-(7-carbethoxy-6-thiaheptyl)cyclopent-2-en-1-one (Ex. 749) | 6 | ethyl 15-hydroxy-9-oxo-3-thia-16,16-trimethylene-7a-homo-13-trans-prostenoate |
| 58 | 2-(6-carbethoxy-2-cis-hexenyl)cyclopent-2-en-1-one[b,c] | 6 | ethyl 15-hydroxy-9-oxo-16,16-trimethylene-5-cis-13-trans-prostadienoate |
| 59 | 2-(5-carbethoxy-2-cis-pentenyl)cyclopent-2-en-1-one[b] | 6 | ethyl 15-hydroxy-9-oxo-16,16-trimethylene-7-nor-5-cis-13-trans-prostadienoate |
| 60 | 2-(7-carbethoxy-2-cis-heptenyl)cyclopent-2-en-1-one[b] | 6 | ethyl 15-hydroxy-9-oxo-16,16-trimethylene-7a-homo-5-cis-13-trans-prostadienoate |
| 61 | 2-(6-carbethoxy-4-methyl-2-cis-hexenyl)cyclopent-2-en-1-one[b] | 6 | ethyl 15-hydroxy-4-methyl-9-oxo-16,16-trimethylene-5-cis-13-trans-prostadienoate |
| 62 | 2-(6-carbethoxy-4-ethyl-2-cis-hexenyl)cyclopen-2-en-1-one[b] | 6 | ethyl 4-ethyl-15-hydroxy-9-oxo-16,16-trimethylene-5-cis-13-trans-prostadienoate |
| 63 | 2-(6-carbethoxy-4-propyl-2-cis-hexenyl)cyclopent-2-en-1-one[b] | 6 | ethyl 15-hydroxy-9-oxo-4-propyl-16,16-trimethylene-5-cis-13-trans-prostadienoate |
| 64 | 2-(6-carbethoxy-4(R)-methyl-2-cis-hexenyl)-cyclopent-2-en-1-one[b] | 6 | ethyl 15-hydroxy-4(R)-methyl-9-oxo-16,16-trimethylene-5-cis-13-trans-prostadienoate |
| 64a | 2-(6-carbethoxyhexyl)-cyclopent-2-en-1-one | 40 | ethyl 15-hydroxy-9-oxo-16,16-trimethylene-19-nor-13-trans-prostenoate |
| 65 | 2-(5-carbethoxypentyl)-cyclopent-2-en-1-one | 40 | ethyl 15-hydroxy-9-oxo-16,16-trimethylene-7,19-dinor-13-trans-prostenoate |
| 66 | 2-(6-carbethoxy-6-methylhexyl)cyclopent-2-en-1-one | 40 | ethyl 15-hydroxy-9-oxo-2-methyl-16,16-trimethylene-19-nor-13-trans-prostenoate |
| 67 | 2-(6-carbethoxy-5,6-trans-methanohexyl)cyclopent-2-en-1-one | 41 | ethyl 15-hydroxy-2,3-trans-methano-20-methyl-9-oxo-16,16-trimethylene-13-trans-prostenoate |
| 67a | 2-(6-carbethoxyhexyl)-cyclopent-2-en-1-one | 41 | ethyl 15-hydroxy-20-methyl-9-oxo-16,16-trimethylene-13-trans-prostenoate |
| 68 | 2-(6-carbethoxy-5,5-dimethylhexyl)cyclopent- | 41 | ethyl 15-hydroxy-2,2,20-trimethyl-9-oxo-16,16-trimethylene-13-trans-prostenoate |

TABLE VII-continued

| Example | Starting cyclopentenone | Starting 1-iodo-1-trans-alkene of Example | Product Alkyl 9-oxo-13-trans-prostenoate and the corresponding 15-epimer |
|---|---|---|---|
| 69 | 2-(6-carbethoxy-5-oxa-hexyl)cyclopent-2-en-1-one | 41 | ethyl 15-hydroxy-20-methyl-3-oxa-9-oxo-16,16-trimethylene-13-trans-prostenoate |
| 70 | 2-(6-carbethoxy-6-phenyl-hexyl)cyclopent-2-en-1-one | 42 | ethyl 20-ethyl-15-hydroxy-9-oxo-2-phenyl-16,16-trimethylene-13-trans-prostenoate |
| 70a | 2-(6-carbethoxyhexyl)-cyclopent-2-en-1-one | 42 | ethyl 20-ethyl-15-hydroxy-9-oxo-16,16-trimethylene-13-trans-prostenoate |
| 71 | 2-(6-carbethoxy-2-cis-hexenyl)cyclopent-2-en-1-one | 42 | ethyl 20-ethyl-15-hydroxy-9-oxo-16,16-trimethylene-5-cis-13-trans-prostadienoate |
| 72 | 2-(6-carbethoxy-4-methyl-2-cis-hexenyl)cyclopent-2-en-1-one | 42 | ethyl 20-ethyl-15-hydroxy-4-methyl-9-oxo-16,16-trimethylene-5-cis-13-trans-prostadienoate |
| 73 | 2-(6-carbethoxyhexyl)-cyclopent-2-en-1-one | 6a | ethyl 15-hydroxy-9-oxo-16,16-tetramethylene-13-trans-prostenoate |
| 74 | 2-(8-carbethoxyctyl)-cyclopent-2-en-1-one | 6a | ethyl 15-hydroxy-9-oxo-16,16-tetramethylene-7a,7b-bishomo-13-trans-prostenoate |
| 75 | 2-(6-carbethoxy-6-methyl-hexyl)cyclopent-2-en-1-one | 6a | ethyl 15-hydroxy-2-methyl-9-oxo-16,16-tetramethylene-13-trans-prostenoate |
| 76 | 2-(6-carbethoxy-5,6-trans-methanohexyl)-cyclopent-2-en-1-one | 6a | ethyl 15-hydroxy-2,3-trans-methano-9-oxo-16,16-tetramethylene-13-trans-prostenoate |
| 77 | 2-(6-carbethoxy-5,5-dimethylhexyl)cyclo-pent-2-en-1-one | 6a | ethyl 15-hydroxy-3,3-dimethyl-9-oxo-16,16-tetramethylene-13-trans-prostenoate |
| 78 | 2-(6-carbethoxy-6-phenyl-hexyl)cyclopent-2-en-1-one | 6a | ethyl 15-hydroxy-9-oxo-2-phenyl-16,16-tetramethylene-13-trans-prostenoate |
| 79 | 2-(6-carbethoxy-5-oxa-hexyl)cyclopent-2-en-1-one | 6a | ethyl 15-hydroxy-3-oxa-9-oxo-16,16-tetramethylene-13-trans-prostenoate |
| 80 | 2-(6-carbethoxy-5-thia-hexyl)cyclopent-2-en-1-one | 6a | ehtyl 15-hydroxy-9-oxo-16,16-tetramethylene-3-thia-13-trans-prostenoate |
| 81 | 2-(6-carbethoxy-2-cis-hexenyl)cyclopent-2-en-1-one | 6a | ethyl 15-hyddroxy-9-oxo-16,16-tetramethylene-5-cis-13-trans-prostadienoate |
| 82 | 2-(6-carbethoxy-4-ethyl-2-cis-hexenyl)cyclo-pent-2-en-1-one | 6a | ethyl 15-hydroxy-4-ethyl-9-oxo-16,16-tetramethylene-5-cis-13-trans-prostadienoate |
| 83 | 2-(6-carbethoxyhexyl)-cyclopent-2-en-1-one | 45 | ethyl 15-hydroxy-9-oxo-16,16-trimethylene-13-trans-prosten-18-ynoate |
| 84 | 2-(5-carbethoxyhexyl)-cyclopent-2-en-1-one | 45 | ethyl 15-hydroxy-9-oxo-16,16-trimethylene-7-nor-13-trans-prosten-18-ynoate |
| 85 | 2-(6-carbethoxy-6-methyl-hexyl)cyclopent-2-en-1-one | 45 | ethyl 15-hydroxy-2-methyl-9-oxo-16,16-trimethylene-13-trans-prosten-18-ynoate |
| 86 | 2-(6-carbethoxy-5,5-di-methylhexyl)cyclopent-2-en-1-one | 45 | ethyl 15-hydroxy-3,3-dimethyl-9-oxo-16,16-trimethylene-13-trans-prosten-18-ynoate |
| 87 | 2-(6-carbethoxy-5-oxa-hexyl)cyclopent-2-en-1-one | 45 | ethyl 15-hydroxy-3-oxa-9-oxo-16,16-trimethylene-13-trans-prosten-18-ynoate |
| 88 | 2-(6-carbethoxy-5-thia-hexyl)cyclopent-2-en-1-one | 45 | ethyl 15-hydroxy-9-oxo-3-thia-16,16-trimethylene-13-trans-prosten-18-ynoate |
| 89 | 2-(6-carbethoxy-6-phenyl-hexyl)cyclopent-2-en-1-one | 45 | ethyl 15-hydroxy-9-oxo-2-phenyl-16,16-trimethylene-13-trans-prosten-8-ynoate |
| 90 | 2-(6-carbethoxy-2-cis-hex-enyl)cyclopent-2-en-1-one | 45 | ethyl 15-hydroxy-9-oxo-16,16-trimethylene-5-cis-13-trans-prostadien-18-ynoate |
| 91 | 2-(6-carbethoxy-4-methyl-2-cis-hexenyl)cyclopent-2-en-1-one | 45 | ethyl 15-hydroxy-4-methyl-9-oxo-16,16-trimethylene-5-cis-13-trans-prostadien-18-ynoate |
| 92 | 2-(6-carbethoxyhexyl)-cyclopent-2-en-1-one | 753 | ethyl 15-hydroxy-9-oxo-16,16-trimethylene-13-trans-18-cis-prostadienoate |
| 93 | 2-(7-carbethoxyheptyl)-cyclopent-2-en-1-one | 753 | ethyl 15-hydroxy-9-oxo-16,16-trimethylene-7a-homo-13-trans-18-cis-prostadienoate |
| 94 | 2-(6-carbethoxy-6-ehtyl-hexyl)cyclopent-2-en-1-one | 753 | ethyl 2-ethyl-15-hydroxy-9-oxo-16,16-trimethylene-13-trans-18-cis-prostadienoate |
| 95 | 2-(6-carbethoxy-5,6-trans-methanohexyl)cyclopent-2-en-1-one | 753 | ethyl 15-hydroxy-2,3-trans-methano-9-oxo-16,16-trimethylene-13-trans-18-cis-prestadienoate |
| 96 | 2-(6-carbethoxy-5-oxa-hexyl)cyclopent-2-en-1-one | 753 | ethyl 15-hydroxy-5-oxa-9-oxo-16,16-trimethylene-13-trans-18-cis-prostadienoate |
| 97 | 2-(6-carbethoxy-6-phenylhexyl)cyclopent-2-en-1-one | 753 | ethyl 15-hydroxy-9-oxo-2-phenyl-16,16-trimethylene-13-trans-18-cis-prostadienoate |
| 98 | 2-(7-carbethoxy-6-thia-heptyl)cyclopent-2-1-one | 753 | ethyl 15-hydroxy-9-oxo-3-thia-16,16-trimethylene-7a-homo-13-trans-18-cis-prostadienoate |
| 99 | 2-(6-carbethoxy-2-cis hexenyl)cyclopent-2-en-1-one | 753 | ethyl 15-hydroxy-9-oxo-16,16-trimethylene-5-cis-13-trans-18-cis-prostatrienoate |

TABLE VII-continued

| Example | Starting cyclopentenone | Starting 1-iodo-1-trans-alkene of Example | Product Alkyl 9-oxo-13-trans-prostenoate and the corresponding 15-epimer |
|---|---|---|---|
| 100 | 2-(6-carbethoxy-4(R)-methyl-2-cis-hexenyl)-cyclopent-2-en-1-one | 75\$ | ethyl 15-hydroxy-4-methyl-9-oxo-16,15-trimethylene-5-cis-13-trans-18-cis-prostatrienoate |
| 101 | 2-(6-carbethoxyhexyl)-cyclopent-2-en-1-one | 43 | ethyl 15-hydroxy-9-oxo-17-phenyl-16,16-trimethylene-18,19,20-trinor-13-trans-prostenoate |
| 102 | 2-(6-carbethoxy-6-ethyl-hexyl)cyclopent-2-en-1-one | 43 | ethyl 2-ethyl-15-hydroxy-9-oxo-17-phenyl-16,16-trimethylene-18,19,20-trinor-13-trans-prostenoate |
| 103 | 2-(6-carbethoxy-6-phenyl-hexyl)cyclopent-2-en-1-one | 43 | ethyl 15-hydroxy-9-oxo-2,17-dephenyl-16,16-trimethylene-18,19,20-trinor-13-trans-prostenoate |
| 104 | 2-(6-carbethoxy-2-cis-hexenyl)cyclopent-2-en-1-one | 43 | ethyl 15-hydroxy-9-oxo-17-phenyl-16,16-trimethylene-18,19,20-trinor-5-cis-13-trans-prostadienoate |
| 105 | 2-(6-carbethoxy-4-methyl-2-cis-hexenyl)-cyclopent-2-en-1-one | 43 | ethyl 15-hydroxy-4-methyl-9-oxo-17-phenyl-16,16-trimethylene-18,19,20-trinor-5-cis-13-trans-prostadienoate |
| 106 | 2-(6-carbethoxy-5-thia-hexyl)cyclopent-2-en-1-one | 43 | ethyl 15-hydroxy-9-oxo-17-phenyl-3-thia-16,16-trimethylene-18,19,20-trinor-13-trans-prostenoate |
| 107 | 2-(6-carbethoxy-5,6-trans-methanohexyl)cyclopent-2-en-1-one | 43 | ethyl 15-hydroxy-2,3-trans-methano-9-oxo-17-phenyl-16,16-trimethylene-18,19,20-trinor-13-trans-prostenoate |
| 108 | 2-(6-carbethoxyhexyl)-cyclopent-2-en-1-one | 44 | ethyl 18-cyclopentyl-15-hydroxy-9-oxo-16,16-trimethylene-19,20-dinor-13-trans-prostenoate |
| 109 | 2-(6-carbethoxy-5,5-dimethylhexyl)cyclopent-2-en-1-one | 44 | ethyl 18-cyclopentyl-15-hydroxy-9-oxo-16,16-trimethylene-19,20-dinor-13-trans-prostenoate |
| 110 | 2-(6-carbethoxy-6-phenyl-hexyl)cyclopent-2-en-1-one | 44 | ethyl 18-cyclopentyl-15-hydroxy-9-oxo-2-phenyl-16,16-trimethylene-19,20-dinor-13-trans-prostenoate |
| 111 | 2-(6-carbethoxy-2-cis-hexenyl)cyclopent-2-en-1-one | 44 | ethyl 18-cyclopentyl-15-hydroxy-9-oxo-16,16-trimethylene-19,20-dinor-5-cis-13-trans-prostadienoate |
| 112 | 2-(6-carbethoxy-4-propyl-2-cis-hexenyl)cyclopent-2-en-1-one | 44 | ethyl 18-cyclopentyl-15-hydroxy-9-oxo-4-propyl-16,16-trimethylene-19,20-dinor-5-cis-13-trans-prosytadienoate |
| 113 | 2-(6-carbethoxy-5-oxa-hexyl)cyclopent-2-en-1-one | 44 | ethyl 18-cyclopentyl-15-hydroxy-3-oxa-9-oxo-16,16-trimethylene-19,20-dinor-13-trans-postenoate |
| 114 | 2-(6-carbethoxy-5-thia-hexyl)cyclopent-2-en-1-one | 44 | ethyl 18-cyclopentyl-15-hydroxy-9-oxo-3-thia-16,16-trimethylene-19,20-dinor-13-trans-prostenoate |
| 115 | 2-(6-carbethoxy-5,6-trans-methanohexyl)-cyclopent-2-en-1-one | 44 | ethyl 18-cyclopentyl-15-hydroxy-2,3-trans-methano-9-oxo-16,16-trimethylene-19,20-dinor-13-trans-prostenoate |
| 116 | 2-(6-carbethoxyhexyl)-cyclopent-2-en-1-one | 5c | ethyl 15-hydroxy-9-oxo-16,16-trimethylene-13-cis-prostenoate |
| 117 | 2-(8-carbethoxyoctyl)-cyclopent-2-en-1-one | 5c | ethyl 15-hydroxy-9-oxo-16,16-trimethylene-7a,7b-bishomo-13-cis-prostenoate |
| 118 | 2-(6-carbethoxy-6-methyl-hexyl)cyclopent-2-en-1-one | 5c | ethyl 15-hydroxy-2-methyl-9-oxo-16,16-trimethylene-13-cis-prostenoate |
| 119 | 2-(6-carbethoxy-5,5-dimethylhexyl)cyclopent-2-en-1-one | 5c | ethyl 15-hydroxy-3,3-dimethyl-9-oxo-16,16-trimethylene-13-cis-prostenoate |
| 120 | 2-(6-carbethoxy-6-phenyl-hexyl)cyclopent-2-en-1-one | 5c | ethyl 15-hydroxy-9-oxo-2-phenyl-16,16-trimethylene-13-cis-prostenoate |
| 121 | 2-(6-carbethoxy-2-cis-hexenyl)cyclopent-2-en-1-one | 5c | ethyl 15-hydroxy-9-oxo-16,16-trimethylene-5-cis-13-cis-prostadienoate |
| 122 | 2-(6-carbethoxy-4-methyl-2-cis-hexenyl)cyclo-pent-2-en-1-one | 5c | ethyl 15-hydroxy-4-methyl-9-oxo-16,16-trimethylene-5-cis-13-cis-prostadienoate |
| 123 | 2-(6-carbethoxy-5-oxa-hexyl)cyclopent-2-en-1-one | 5c | ethyl 15-hydroxy-3-oxa-9-oxo-16,16-tremethylene-5-cis-13-cis-prostadienoate |
| 124 | 2-(6-carbethoxy-5,6-trans-methanohexyl)-cy-clopent-2-en-1-one | 5c | ethyl 15-hydroxy-2,3-trans-methano-9-oxo-16,16-trimethylene-5-cis-13-cis-prostadienoate |

References:
[a(1)] Belgian Patent 815,979 (Dec. 6, 1974); Derwent Central Patents Index, Farmdoc B - 88668V/52;
[(2)] K.F. Bernady, J.F. Poletto and M.J. Weiss, U.S. Patent 3,836,581 (Sept. 17, 1974).
[b] Netherlands Patent Spec. 7310-276) Derwent Central Patents Index, Farmdoc B-10735 V/06.
[c] P.A. Grieco and J.J. Reap, J. Org. Chem., 19, 3413 (1973).

EXAMPLES 125–200

In the manner described in Example 8, the carboxylic acids of TABLE VIII (below) are prepared by saponification of the corresponding esters of the Table.

TABLE VIII

| Example | Starting ester of Example | Product |
|---|---|---|
| 125 | 47 | 15-hydroxy-9-oxo-16,16-trimethylene-7-nor-13-trans-prostenoic acid |
| 125a | 48 | 15-hydroxy-9-oxo-16,16-trimethylene-7a-homo-13-trans-prostenoic acid |
| 125b | 49 | 15-hydroxy-9-oxo-16,16-trimethylene-7a,7b-bishomo-13-trans-prostenoic acid |
| 126 | 50 | 15-hydroxy-2-methyl-9-oxo-16,16-trimethylene-13-trans-prostenoic acid |
| 127 | 51 | 2-ethyl-15-hydroxy-9-oxo-16,16-trimethylene-13-trans-prostenoic acid |
| 128 | 52 | 15-hydroxy-2,3-trans-methano-9-oxo-16,16-trimethylene-13-trans-prostenoic acid |
| 129 | 53 | 15-hydroxy-3,3-dimethyl-9-oxo-16,16-trimethylene-13-trans-prostenoic acid |
| 130 | 54 | 15-hydroxy-3-oxa-9-oxo-16,16-trimethylene-13-trans-prostenoic acid |
| 131 | 55 | 15-hydroxy-9-oxo-3-thia-16,16-trimethylene-13-trans-prostenoic acid |
| 132 | 56 | 15-hydroxy-9-oxo-2-phenyl-16,16-trimethylene-13-trans-prostenoic acid |
| 133 | 57 | 15-hydroxy-9-oxo-3-thia-16,16-trimethylene-7a-homo-13-trans-prostenoic acid |
| 134 | 58 | 15-hydroxy-9-oxo-16,16-trimethylene-5-cis,13-trans-prostadienoic acid |
| 135 | 59 | 15-hydroxy-9-oxo-16,16-trimethylene-7-nor-5-cis-13-trans-prostadienoic acid |
| 136 | 60 | 15-hydroxy-9-oxo-16,16-trimethylene-7a-homo-5-cis-13-trans-prostedienoic acid |
| 137 | 61 | 15-hydroxy-4-methyl-9-oxo-16,16-trimethylene-5-cis-13-trans-prostadienoic acid |
| 138 | 62 | 4-ethyl-15-hydroxy-9-oxo-16,16-trimethylene-5-cis-13-trans-prostadienoic acid |
| 139 | 63 | 15-hydroxy-9-oxo-4-propyl-16,16-trimethylene-5-cis-13-trans-prostadienoic acid |
| 140 | 64 | 15-hydroxy-4(R)-methyl-9-oxo-16,16-trimethylene-5-cis-13-trans-prostadenoic acid |
| 140a | 64a | 15-hydroxy-9-oxo-16,16-trimethylene-19-nor-13-trans-prostenoic acid |
| 141 | 65 | 15-hydroxy-9-oxo-16,16-trimethylene-7,19-dinor-13-trans-prostenoic acid |
| 142 | 66 | 15-hydroxy-9-oxo-2-methyl-16,16-trimethylene-19-nor-13-trans-prostenoic acid |
| 143 | 67 | 15-hydroxy-2,3-trans-methano-20-methyl-9-oxo-16,16-trimethylene-13-trans-prostenoic acid |
| 143a | 67a | 15-hydroxy-20-methyl-9-oxo-16,16-trimethylene-13-trans-prostenoic acid |
| 144 | 68 | 15-hydroxy-2,2,20-trimethyl-9-oxo-16,16-trimethylene-13-trans-prostenoic acid |
| 145 | 69 | 15-hydroxy-20-methyl-3-oxa-9-oxo-16,16-trimethylene-13-trans-prostenoic acid |
| 146 | 70 | 20-ethyl-15-hydroxy-9-oxo-2-phenyl-16,16-trimethylene-13-trans-prostenoic acid |
| 146a | 70a | 20-ethyl-15-hydroxy-9-oxo-16,16-trimethylene-13-trans-prostenoic acid |
| 147 | 71 | 20-ethyl-15-hydroxy-9-oxo-16,16-trimehtylene-5-cis-13-trans-prostadienoic acid |
| 148 | 72 | 20-ethyl-15-hydroxy-4-methyl-9-oxo-16,16-trimethylene-5-cis-13-trans-prostadienoic acid |
| 149 | 73 | 15-hydroxy-9-oxo-16,16-tetramethylene-13-trans-prostenoic acid |
| 150 | 74 | 15-hydroxy-9-oxo-16,16-tetramethylene-7a,7b-bishomo-13-trans-prostenoic acid |
| 151 | 75 | 15-hydroxy-2-methyl-9-oxo-16,16-tetramethylene-13-trans-prostenoic acid |
| 152 | 76 | 15-hydroxy-2,3-trans-methano-9-oxo-16,16-tetramethylene-13-trans-prostenoic acid |
| 153 | 77 | 15-hydroxy-3,3-dimethyl-9-oxo-16,16-tetramethylene-13-trans-prostenoic acid |
| 154 | 78 | 15-hydroxy-9-oxo-2-phenyl-16,16-tetramethylene-13-trans-prostenoic acid |
| 155 | 79 | 15-hydroxy-3-oxa-9-oxo-16,16-tetramethylene-13-trans-prostenoic acid |
| 156 | 80 | 15-hydroxy-9-oxo-16,16-tetramethylene-3-thia-13-trans-prostenoic acid |
| 157 | 81 | 15-hydroxy-9-oxo-16,16-tetramethylene-5-cis-13-trans-prostadienoic acid |
| 158 | 82 | 15-hydroxy-4-ethyl-9-oxo-16,16-tetramethylene-5-cis-13-trans-prostadienoic acid |
| 159 | 83 | 15-hydroxy-9-oxo-16,16-trimethylene-13-trans-prosten-18-ynoic acid |
| 160 | 84 | 15-hydroxy-9-oxo-16,16-trimethylene-7-nor-13-trans- |

TABLE VIII-continued

| Example | Starting ester of Example | Product |
|---|---|---|
| | | prosten-18-ynoic acid |
| 161 | 85 | 15-hydroxy-2-methyl-9-oxo-16,16-trimethylene-13-trans-prosten-18-ynoic acid |
| 162 | 86 | 15-hydroxy-3,3-dimethyl-9-oxo-16,16-trimethylene-13-trans-prosten-18-ynoic acid |
| 163 | 87 | 15-hydroxy-3-oxa-9-oxo-16,16-trimethylene-13-trans-prosten-18-ynoic acid |
| 164 | 88 | 15-hydroxy-9-oxo-3-thia-16,16-trimethylene-13-trans-prosten-18-ynoic acid |
| 165 | 89 | 15-hydroxy-9-oxo-2-phenyl-16,16-trimethylene-13-trans-prosten-18-ynoic acid |
| 166 | 90 | 15-hydroxy-9-oxo-16,16-trimethylene-5-cis-13-trans-prostadien-18-ynoic acid |
| 167 | 91 | 15-hydroxy-4-methyl-9-oxo-16,16-trimethylene-5-cis-13-trans-prostadien-18-ynoic acid |
| 168 | 92 | 15-hydroxy-9-oxo-16,16-trimehylene-13-trans-18-cis-prostadienoic acid |
| 169 | 93 | 15-hydroxy-9-oxo-16,16-trimethylene-7a-homo-13-trans-18-cis-prostadienoic acid |
| 170 | 94 | 2-ethyl-15-hydroxy-9-oxo-16,16-trimethylene-13-trans 18-cis-prostadienoic acid |
| 171 | 95 | 15-hydroxy-2,3-trans-methano-9-oxo-16,16-trimethylene-13-trans-18-cis-prostadienoic acid |
| 172 | 96 | 15-hydroxy-3-oxa-9-oxo-16,16-trimethylene-13-trans-18-cis-prostadienoic acid |
| 173 | 97 | 15-hydroxy-9-oxo-2-phenyl-116,16-trimethylene-13-trans-18-cis-prostadienoic acid |
| 174 | 98 | 15-hydroxy-9-oxo-3-thia-16,16-trimethylene-7a-homo-13-trans-18-cis-prostadienoic acid |
| 175 | 99 | 15-hydroxy-9-oxo-16,16-trimethylene-5-cis-13-trans-18-cis-prostatrienoic acid |
| 176 | 100 | 15-hydroxy-4-methyl-9-oxo-16,16-trimethylene-5-cis-13-trans-18-cis-prostatrienoic acid |
| 177 | 101 | 15-hydroxy-9-oxo-17-phenyl-16,16-trimethylene-18,19,20-trinor-13-trans-prostenoic acid |
| 178 | 102 | 2-ethyl-15-hydroxy-9-oxo-17-phenyl-16,16-trimethylene-18,19,20-trinor-13-trans-prostenoic acid |
| 179 | 103 | 15-hydroxy-9-oxo-2,17-diphenyl-16,16-trimethylene-18,19,20-trinor-13-trans-prostenoic acid |
| 180 | 104 | 15-hydroxy-9-oxo-17-phenyl-16,16-trimethylene-18,19,20-trinor-5-cis-13-trans-prostadienoic acid |
| 181 | 105 | 15-hydroxy-4-methyl-9-oxo-17-phenyl-16,16-trimethylene-18,19,20-trinor-5-cis-13-trans-prostadienoic acid |
| 182 | 106 | 15-hydroxy-9-oxo-17-phenyl-3-thia-16,16-trimethylene-18,19,20-trinor-13-trans-prostenoic acid |
| 183 | 107 | 15-hydroxy-2,3-trans-methano-9-oxo-17-phenyl-16,16-trimethylene-18,19,20-trinor-13-trans-prostenoic acid |
| 184 | 108 | 18-cyclopentyl-15-hydroxy-9-oxo-16,16-trimethylene-19,20-dinor-13-trans-prostenoic acid |
| 185 | 109 | 18-cyclopentyl-15-hydroxy-3,3-dimethyl-9-oxo-16,16-trimethylene-19,20-dinor-13-trans-prostenoic acid |
| 186 | 110 | 18-cyclopentyl-15-hydroxy-9-oxo-2-phenyl-16,16-trimethylene-19,20-dinor-13-trans-prostenoic acid |
| 187 | 111 | 18-cyclopentyl-15-hydroxy-9-oxo-16,16-trimethylene-19,20-dinor-5-cis-13-trans-prostadienoic acid |
| 188 | 112 | 18-cyclopentyl-15-hydroxy-9-oxo-4-propyl-16,16-trimethylene-19,20-dinor-5-cis-13-trans-prostadienoic acid |
| 189 | 113 | 18-cyclopentyl-15-hydroxy-3-oxa-9-oxo-16,16-trimethylene-19,20-dinor-13-trans-prostenoic acid |
| 190 | 114 | 18-cyclopentyl-15-hydroxy-9-oxo-3-thia-16,16-trimethylene-19,20-dinor-13-trans-prostenoic acid |
| 191 | 115 | 18-cyclopentyl-15-hydroxy-2,3-trans-methano-9-oxo-16,16-trimethylene-19,20-dinor-13-trans-prostenoic acid |
| 192 | 116 | 15-hydroxy-9-oxo-16,16-trimethylene-13-cis-prostenoic acid |
| 193 | 117 | 15-hydroxy-9-oxo-16,16-trimethylene-7a,7b-bishomo-13-cis-prostenoic acid |
| 194 | 118 | 15-hydroxy-2-methyl-9-oxo-16,16-trimethylene-13-cis-prostenoic acid |
| 195 | 119 | 15-hydroxy-3,3-dimethyl-9-oxo-16,16-trimethylene-13-cis-prostenoic acid |
| 196 | 120 | 15-hydroxy-9-oxo-2-phenyl-16,16-trimethylene-13-cis-prostenoic acid |
| 197 | 121 | 15-hydroxy-9-oxo-16,16-trimethylene-5-cis-13-cis-prostadienoic acid |
| 198 | 122 | 15-hydroxy-4-methyl-9-oxo-16,16-trimethylene-5-cis-13-cis-prostadienoic acid |
| 199 | 123 | 15-hydroxy-3-oxa-9-oxo-16,16-trimethylene-5-cis-13-cis-prostadienoic acid |
| 200 | 124 | 15-hydroxy-2,3-trans-methano-9-oxo-16,16-trimethylene- |

TABLE VIII-continued

| Example | Starting ester of Example | Product |
|---------|---------------------------|---------|
|         |                           | 5-cis-13-cis-prostadienoic acid |

EXAMPLE 201

Preparation of
11α,15-dihydroxy-9-oxo-16,16-trimethylene-5-cis,13-trans-prostadienoic acid and
11α,15-epi-dihydroxy-9-oxo-16,16-trimethylene-5-cis,13-trans-prostadienoic acid To a solution of 12.9 g. of 1-iodo-4,4-trimethylene-3-trimethylsilyloxy-1-trans-octene (Example 6) in 16 ml. of hexanes, cooled to −78° C. in an atmosphere of argon, is added 60 ml. of 0.8 N-tertiary butyllithium in pentane. After stirring for 45 minutes, the solution is allowed to warm to −5° C. and stirred for an additional 1 hour. The solution containing 4,4-trimethylene-3-trimethylsilyloxy-1-trans-octenyl lithium is cooled to −78° C. and there is added a solution of 2.83 g. of copper pentyne in 8.7 ml. of hexamethylphosphorous triamide and 50 ml. of ether. The solution is stirred at −78° C. for 1 hour. To this solution containing lithio pentynyl (4,4-trimethylene-3-trimethylsilyloxy-1-trans-octenyl)-cuprate is added a solution of 8.45 g. of 4-tetrahydropyranyloxy-2-(6-carbotetrahydropyranyloxy-2-cis-hexenyl)cyclopent-2-en-1-one in 50 ml. of ether. The solution is stirred at −15° C. for 1 hour then at 0° C. for 1 hour then poured into 1 l. of saturated ammonium chloride solution and 300 ml. of ether and stirred for 20 minutes. The ether phase is separated and the aqueous phase is extracted twice with ether. The combined ether extracts are treated with 5% sodium thiosulfate solution, saturated sodium chloride solution, dried with anhydrous magnesium sulfate and taken to dryness to furnish 16 g. of an oil.

The crude product is dissolved in 400 ml. of acetic acid-tetrahydrofuran-water (20:10:3) and the mixture is heated at 40° C. for 4 hours with stirring. The solids are removed by filtration and the mother liquor is taken to dryness to furnish an oil. The crude product is applied to a dry column (2″ flat) using 1500 g. of silica gel (Woelm) and developed with cyclohexane-ethyl acetate-acetic acid (60:40:2) to furnish 824 mg. of 11α,15-dihydroxy-9-oxo-5-cis,13-trans-prostadienoic acid and 1.12 g. of 11α,15-epi-dihydroxy-9-oxo-5-cis,13-trans-prostadienoic acid.

EXAMPLES 202–265

The product 11α,15-dihydroxy-9-oxo-16,16-trimethylene-13-trans-prostenoic acids of Table IX below are obtained by the procedure described in Example 201. In accordance with the process described therein; the starting trimethylsilyloxy substituted 1-alkenes listed in Table IX are treated with t-butyllithium providing the corresponding trimethylsilyl substituted trans-1-alkenyl lithium derivatives which on treatment with cuprous pentyne furnish the corresponding lithio pentynyl (trimethylsilyl substituted trans-1-alkenyl)cuprate, which in turn are treated with the 4-oxycyclopent-2-en-1-ones listed in the table. The resulting trimethylsilyl substituted-11α-tetrahydropyranyloxy-13-trans-prostenoic acid tetrahydropyranyl esters are hydrolyzed to the listed products by treatment with acetic acid-tetrahydrofuran-water.

TABLE IX

| Example | Starting 4-oxy-cyclopent-2-en-1-one | Starting 1-iodo-1-trans-alkene of Example | 9-oxo-11α-hydroxy-13-trans-prostenoic acid and the corresponding 15-epimer |
|---------|-------------------------------------|-------------------------------------------|----------------------------------------------------------------------------|
| 202 | 4-tetrahydropyranyloxy-2-(6-carbotetrahydropyranyloxyhexyl)cyclopent-2-en-1-one[a] | 6 | 11α,15-dihydroxy-9-oxo-16,16-trimethylene-13-trans-prostenoic acid |
| 203 | 4-tetrahydropyranyloxy-2-(5-carbotetrahydropyranyloxypentyl)-cyclopent-2-en-1-one[a] | 6 | 11α,15-dihydroxy-9-oxo-16,16-trimethylene-7-nor-13-trans-prostenoic acid |
| 204 | 4-tetrahydropyranyloxy-2-(7-carbotetrahydropyranyloxyheptyl)-cyclopent-2-en-1-one[a] | 6 | 11α,15-dihydroxy-9-oxo-16,16-trimethylene-7-homo-13-trans-prostenoic acid |
| 205 | 4-tetrahydropyranyloxy-2-(8-carbotetrahydropyranyloxyoctyl)-cyclopent-2-en-1-one[a] | 6 | 11α,15-dihydroxy-9-oxo-16,16-trimethylene-7a,7b-bishomo-13-trans-prostenoic acid |
| 206 | 4-tetrahydropyranyloxy-2-(6-carbotetrahydropyranyloxy-6-methylhexyl)cyclopent-2-en-1-one[a] | 6 | 11α,15-dihydroxy-2-methyl-9-oxo-16,16-trimethylene-13-trans-prostenoic acid |
| 207 | 4-tetrahydropyranyloxy-2-(6-carbotetrahydropyranyloxy-6-ethylhexyl)cyclopent-2-en-1-one[a] | 6 | 2-ethyl-11α,15-dihydroxy-9-oxo-16,16-trimethylene-13-trans-prostenoic acid |
| 208 | 4-tetrahydropyranyloxy-2-(6-carbotetrahydropyranyloxy-5,5-dimethylhexyl)cyclopent-2-en-1-one[a] | 6 | 11α,15-dihydroxy-3,3-dimethyl-9-oxo-16,16-tetramethylene-13-trans-prostenoic acid |
| 209 | 4-tetrahydropyranyloxy-2-(5-carbotetrahydropyranyloxy-2-cis-pentenyl)cyclopent-2-en-1-one[a] | 6 | 11α,15-dihydroxy-9-oxo-16,16-trimethylene-7-nor-5-cis,13-trans-prostadienoic acid |
| 210 | 4-tetrahydropyranyloxy-2-(7-carbotetrahydropyranyloxy-2-cis-heptenyl)cyclopent-2-en-1-one[a] | 6 | 11α,15-dihydroxy-16,16-trimethylene-9-oxo-7a-homo-5-cis,13-trans-prostadienoic acid |
| 211 | 4-tetrahydropyranyloxy-2-(6-carbotetrahydropyranyloxy-4-methyl-2-cis-hexenyl)cyclopent-2-en-1-one[a] | 6 | 11α,15-dihydroxy-4-methyl-9-oxo-16,16-trimethylene-5-cis,13-trans-prostadienoic acid |
| 212 | 4-tetrahydropyranyloxy-2- | 6 | 11α,15-dihydroxy-4(R)-methyl-16,16-tri- |

TABLE IX-continued

| Example | Starting 4-oxy-cyclopent-2-en-1-one | Starting 1-iodo-1-trans-alkene of Example | 9-oxo-11α-hydroxy-13-trans-prostenoic acid and the corresponding 15-epimer |
|---|---|---|---|
| | (6-carbotetrahydropyranyloxy-4(R)-methyl-2-cis-hexenyl)-cyclopent-2-en-1-one[a] | | methylene-9-oxo-5-cis,13-trans-prostadienoic acid |
| 213 | 4-tetrahydropyranyloxy-2-(6-carbotetrahydropyranyloxy-4-ethyl-2-cis-hexenyl)cyclopent-2-en-1-one[a] | 6 | 4-ethyl-11α,15-dihydroxy-16,16-trimethylene-9-oxo-5-cis,13-trans-prostadienoic acid |
| 214 | 4-tetrahydropyranyloxy-2-(6-carbotetrahydropyranyloxy-4-propyl-2-cis-hexenyl)cyclopent-2-en-1-one[a] | 6 | 11α,15-dihydroxy-4-propyl-16,16-trimethylene-9-oxo-5-cis,13-trans-prostadienoic acid |
| 215 | 4-tetrahydropyranyloxy-2-(6-carbotetrahydropyranyloxy-hexyl)cyclopent-2-en-1-one | 40 | 11α,15-dihydroxy-9-oxo-16,16-trimethylene-19-nor-13-trans-prostenoic acid |
| 216 | 4-tetrahydropyranyloxy-2-(8-carbotetrahydropyranyloxyoctyl)cyclopent-2-en-1-one | 40 | 11α,15-dihydroxy-9-oxo-16,16-trimethylene-7a,7b-bishomo-19-nor-13-trans-prostenoic acid |
| 216a | 4-tetrahydropyranyloxy-2-(6-carbotetrahydropyranyloxy-2-cis-hexenyl)cyclopent-2-en-1-one | 40 | 11α,15-dihydroxy-9-oxo-16,16-trimethylene-5-cis,13-trans-19-nor-prostadienoic acid |
| 217 | 4-tetrahydropyranyloxy-2-(6-carbotetrahydropyranyloxyhexyl)cyclopent-2-en-1-one | 41 | 11α,15-dihydroxy-20-methyl-9-oxo-16,16-trimethylene-13-trans-prostenoic acid |
| 218 | 4-tetrahydropyranyloxy-2-(6-carbotetrahydropyranyloxy-6-methylhexyl)cyclopent-2-en-1-one | 41 | 11α,15-dihydroxy-2,20-dimethyl-9-oxo-16,16-trimethylene-13-trans-prostenoic acid |
| 219 | 4-tetrahydropyranyloxy-2-(6-carbotetrahydropyranyloxy-2-cis-hexenyl)cyclopent-2-en-1-one | 41 | 11α,15-dihydroxy-20-methyl-9-oxo-16,16-trimethylene-5-cis,13-trans-prostadienoic acid |
| 220 | 4-tetrahydropyranyloxy-2-(7-carbotetrahydropyranyloxy-2-cis-heptenyl)cyclopent-2-en-1-one | 41 | 11α,15-dihydroxy-20-methyl-9-oxo-16,16-trimethylene-7a-homo-5-cis,13-trans-prostadienoic acid |
| 221 | 4-tetrahydropyranyloxy-2-(6-carbotetrahydropyranyloxyhexyl)cyclopent-2-en-1-one | 42 | 20-ethyl-11α,15-dihydroxy-9-oxo-16,16-trimethylene-13-trans-prostenoic acid |
| 222 | 4-tetrahydropyranyloxy-2-(6-carbotetrahydropyranyloxy-2-cis-hexenyl)cyclopent-2-en-1-one | 42 | 20-ethyl-11α,15-dihydroxy-9-oxo-16,16-trimethylene-5-cis,13-trans-prostadienoic acid |
| 222a | 4-tetrahydropyranyloxy-2-(6-carbotetrahydropyranyloxy-4-methyl-2-cis-hexenyl)cyclopent-2-en-1-one | 42 | 20-ethyl-11α,15-dihydroxy-4-methyl-9-oxo-16,16-trimethylene-5-cis,13-trans-prostadienoic acid |
| 223 | 4-tetrahydropyranyloxy-2-(6-carbotetrahydropyranyloxyhexyl)cyclopent-2-en-1-one | 6a | 11α,15-dihydroxy-9-oxo-16,16-tetramethylene-13-trans-prostenoic acid |
| 224 | 4-tetrahydropyranyloxy-2-(6-carbotetrahydropyranyloxy-2-cis-hexenyl)cyclopent-2-en-1-one | 6a | 11α,15-dihydroxy-9-oxo-16,16-tetramethylene-5-cis,13-trans-prostadienoic acid |
| 225 | 4-tetrahydropyranyloxy-2-(5-carbotetrahydropyranyloxypentyl)cyclopent-2-en-1-one | 6a | 11α,15-dihydroxy-9-oxo-16,16-tetramethylene-7-nor-13-trans-prostenoic acid |
| 226 | 4-tetrahydropyranyloxy-2-(6-carbotetrahydropyranyloxy-6-ethylhexyl)cyclopent-2-en-1-one | 6a | 2-ethyl-11α,15-dihydroxy-9-oxo-16,16-tetramethylene-13-trans-prostenoic acid |
| 227 | 4-tetrahydropyranyloxy-2-(6-carbotetrahydropyranyloxy-5,5-dimethylhexyl)cyclopent-2-en-1-one | 6a | 11α,15-dihydroxy-3,3-dimethyl-9-oxo-16,16-tetramethylene-13-trans-prostenoic acid |
| 228 | 4-tetrahydropyranyloxy-2-(6-carbotetrahydropyranyloxy-4(R)-methyl-2-cis-hexenyl)cyclopent-2-en-1-one | 6a | 11α,15-dihydroxy-4-methyl-9-oxo-16,16-tetramethylene-5-cis,13-trans-prostadienoic acid |
| 229 | 4-tetrahydropyranyloxy-2-(6-carbotetrahydropyrany- | 6a | 11α,15-dihydroxy-3-oxa-9-oxo-16,16-tetramethylene-13-trans-prostenoic acid |

TABLE IX-continued

| Example | Starting 4-oxy-cyclopent-2-en-1-one | Starting 1-iodo-1-trans-alkene of Example | 9-oxo-11α-hydroxy-13-trans-prostenoic acid and the corresponding 15-epimer |
|---|---|---|---|
| | loxy-5-oxahexyl)cyclopent-2-en-1-one | | |
| 230 | 4-tetrahydropyranyloxy-2-(6-carbotetrahydropyranyloxy-5,6-trans-methanohexyl)cyclopent-2-en-1-one | 6a | 11α,15-dihydroxy-2,3-trans-methano-9-oxo-16,16-tetramethylene-13-trans-prostenoic acid |
| 231 | 4-tetrahydropyranyloxy-2-(6-carbotetrahydropyranyloxyhexyl)-cyclopent-2-en-1-one | 45 | 11α,15-dihydroxy-9-oxo-16,16-trimethylene-13-trans-prosten-18-ynoic acid |
| 232 | 4-tetrahydropyranyloxy-2-(6-carbotetrahydropyranyloxy-2-cis-hexenyl)cyclopent-2-en-1-one | 45 | 11α,15-dihydroxy-9-oxo-16,16-trimethylene-5-cis-13-trans-prostadien-18-ynoic acid |
| 233 | 4-tetrahydropyranyloxy-2-(8-carbotetrahydropyranyloxyoctyl)-cyclopent-2-en-1-one | 45 | 11α,15-dihydroxy-9-oxo-16,16-trimethylene-7a,7b-bishomo-13-trans-prosten-18-ynoic acid |
| 234 | 4-tetrahydropyranyloxy-2-(6-carbotetrahydropyranyloxy-6-methylhexyl)cyclopent-2-en-1-one | 45 | 11α,15-dihydroxy-2-methyl-9-oxo-16,16-trimethylene-13-trans-prosten-18-ynoic acid |
| 235 | 4-tetrahydropyranyloxy-2-(7-carbotetrahydropyranyloxy-2-cis-heptenyl)cyclopent-2-en-1-one | 45 | 11α,15-dihydroxy-9-oxo-16,16-trimethylene-7a-homo-5-cis-13-trans-prostadien-18-ynoic acid |
| 236 | 4-tetrahydropyranyloxy-2-(6-carbotetrahydropyranyloxy-4-methyl-2-cis-hexenyl)cyclopent-2-en-1-one | 45 | 11α,15-dihydroxy-4-methyl-9-oxo-16,16-trimethylene-5-cis-13-trans-prostadien-18-ynoic acid |
| 237 | 4-tetrahydropyranyloxy-2-(6-carbotetrahydropyranyloxy-3-oxahexyl)cyclopent-2-en-1-one | 45 | 11α,15-dihydroxy-3-oxa-9-oxo-16,16-trimethylene-13-trans-prosten-18-ynoic acid |
| 238 | 4-tetrahydropyranyloxy-2-(6-carbotetrahydropyranyloxy-5,6-trans-methanohexyl)cyclopent-2-en-1-one | 45 | 11α,15-dihydroxy-2,3-trans-methano-9-oxo-16,16-trimethylene-13-trans-prosten-18-ynoic acid |
| 239 | 4-tetrahydropyranyloxy-2-(6-carbotetrahydropyranyloxyhexyl)cyclopent-2-en-1-one | 753 | 11α,15-dihydroxy-9-oxo-16,16-trimethylene-13-trans,18-cis-prostadienoic acid |
| 240 | 4-tetrahydropyranyloxy-2-(6-carbotetrahydropyranyloxy-2-cis-hexenyl)cyclopent-2-en-1-one | 753 | 11α,15-dihydroxy-9-oxo-16,16-trimethylene-5-cis,13-trans,18-cis-prostatrienoic acid |
| 241 | 4-tetrahydropyranyloxy-2-(6-carbotetrahydropyranyloxyhexyl)cyclopent-2-en-1-one | 43 | 11α,15-dihydroxy-9-oxo-17-phenyl-16,16-trimethylene-18,19,20-trinor-13-trans-prostenoic acid |
| 242 | 4-tetrahydropyranyloxy-2-(6-carbotetrahydropyranyloxy-2-cis-hexenyl)cyclopent-2-en-1-one | 43 | 11α,15-dihydroxy-9-oxo-17-phenyl-16,16-trimethylene-18,19,20-trinor-5-cis,13-trans-prostadienoic acid |
| 243 | 4-tetrahydropyranyloxy-2-(7-carbotetrahydropyranyloxyheptyl)cyclopent-2-en-1-one | 43 | 11α,15-dihydroxy-9-oxo-17-phenyl-16,16-trimethylene-7a-homo-18,19,20-trinor-13-trans-prostenoic acid |
| 244 | 4-tetrahydropyranyloxy-2-(6-carbotetrahydropyranyloxy-6-ethylhexyl)cyclopent-2-en-1-one | 43 | 11α,15-dihydroxy-2-ethyl-9-oxo-17-phenyl-16,16-trimethylene-18,19,20-trinor-13-trans-prostenoic acid |
| 245 | 4-tetrahydropyrayloxy-2-(6-carbotetrahydropyranyloxy-4-propyl-2-cis-hexenyl)cyclopent-2-en-1-one | 43 | 11α,15-dihydroxy-9-oxo-17-phenyl-4-propyl-16,16-trimethylene-18,19,20-trinor-5-cis-13-trans-prostadienoic acid |
| 246 | 4-tetrahydropyrayloxy-2-(6-carbotetrahydropyranyloxy-5-oxa-hexyl)cyclopent-2-en-1-one | 43 | 11α,15-dihydroxy-3-oxa-9-oxo-17-phenyl-16,16-trimethylene-18,19,20-trinor-13-trans-prostenoic acid |
| 247 | 4-tetrahydropyranyloxy-2-(6-carbotetrahydropyranyloxy-5,6-cis-methanohexyl)cyclopent-2-en-1-one | 43 | 11α,15-dihydroxy-2,3-trans-methano-9-oxo-17-phenyl-16,16-trimethylene-18,19,20-trinor-13-trans-prostenoic acid |
| 248 | 4-tetrahydropyranyloxy-2-(6-carbotetrahydropyranyloxy-5,5-dimethylhexyl)cyclopent-2-en-1-one | 43 | 11α,15-dihydroxy-3,3-dimethyl-9-oxo-17-phenyl-16,16-trimethylene-18,19,20-trinor-13-trans-prostenoic acid |
| 249 | 4-tetrahydropyranyloxy-2- | 44 | 18-cyclopentyl-11α,15-dihydroxy-9-oxo- |

TABLE IX-continued

| Example | Starting 4-oxy-cyclopent-2-en-1-one | Starting 1-iodo-1-trans-alkene of Example | 9-oxo-11α-hydroxy-13-trans-prostenoic acid and the corresponding 15-epimer |
|---|---|---|---|
| | (6-carbotetrahydropyranyloxyhexyl)cyclopent-2-en-1-one | | 16,16-trimethylene-19,20-dinor-13-trans-prostenoic acid |
| 250 | 4-tetrahydropyranyloxy-2-(6-carbotetrahydropyranyloxy-2-cis-hexenyl)cyclopent-2-en-1-one | 44 | 18-cyclopentyl-11α,15-dihydroxy-9-oxo-16,16-trimethylene-19,20-dinor-5-cis,13-trans-prostadienoic acid |
| 251 | 4-tetrahydropyranyloxy-2-(5-carbotetrahydropyranyloxypentyl)cyclopent-2-en-1-one | 44 | 18-cyclopentyl-11α,15-dihydroxy-9-oxo-16,16-trimethylene-7,19,20-trinor-13-trans-prostenoic acid |
| 252 | 4-tetrahydropyranyloxy-2-(6-carbotetrahydropyranyloxy-6-ethylhexyl)cyclopent-2-en-1-one | 44 | 18-cyclopentyl-2-ethyl-11α,15-dihydroxy-9-oxo-16,16-trimethylene-19,20-dinor-13-trans-prostenoic acid |
| 253 | 4-tetrahydropyranyloxy-2-(6-carbotetrahydropyranyloxy-5,5-dimethylhexyl)cyclopent-2-en-1-one | 44 | 18-cyclopentyl-11α,15-dihydroxy-3,3-dimethyl-9-oxo-16,16-trimethylene-19,20-dinor-13-trans-prostenoic acid |
| 254 | 4-tetrahydropyranyloxy-2-(7-carbotetrahydropyranyloxy-2-cis-heptenyl)cyclopent-2-en-1-one | 44 | 18-cyclopentyl-11α,15-dihydroxy-9-oxo-16,16-trimethylene-7a-homo-19,20-dinor-5-cis,13-trans-prostadienoic acid |
| 255 | 4-tetrahydropyranyloxy-2-(6-carbotetrahydropyranyloxy-4(R)-methyl-2-cis-hexenyl)cyclopent-2-en-1-one | 44 | 18-cyclopentyl-11α,15-dihydroxy-4-methyl-9-oxo-16,16-trimethylene-19,20-dinor-5-cis,13-trans-prostadienoic acid |
| 256 | 4-tetrahydropyranyloxy-2-(6-carbotetrahydropyranyloxy-5-oxahexyl)cyclopent-2-en-1-one | 44 | 18-cyclopentyl-11α,15-dihydroxy-3-oxa-9-oxo-16,16-trimethylene-19,20-dinor-13-trans-prostenoic acid |
| 257 | 4-tetrahydropyranyloxy-2-(6-carbotetrahydropyranyloxy-5,6-trans-methanohexyl)cyclopent-2-en-1-one | 44 | 18-cyclopentyl-11α,15-dihydroxy-2,3-trans-methano-9-oxo-16,16-trimethylene-19,20-dinor-13-trans-prostenoic acid |
| 258 | 4-tetrahydropyranyloxy-2-(6-carbotetrahydropyranyloxyhexyl)cyclopent-2-en-1-one | 5c | 11α,15-dihydroxy-9-oxo-16,16-trimethylene-13-cis-prostenoic acid |
| 259 | 4-tetrahydropyranyloxy-2-(6-carbotetrahydropyranyloxy-2-cis-hexenyl)cyclopent-2-en-1-one | 5c | 11α,15-dihydroxy-9-oxo-16,16-trimethylene-5-cis,13-cis-prostadienoic acid |
| 260 | 4-tetrahydropyranyloxy-2-(8-carbotetrahydropyranyloxyoctyl)cyclopent-2-en-1-one | 5c | 11α,15-dihydroxy-9-oxo-16,16-trimethylene-7a,7b-bishomo-13-cis-prostenoic acid |
| 261 | 4-tetrahydropyranyloxy-2-(6-carbotetrahydropyranyloxy-6-methylhexyl)cyclopent-2-en-1-one | 5c | 11α,15-dihydroxy-2-methyl-9-oxo-16,16-trimethylene-13-cis-prostenoic acid |
| 262 | 4-tetrahydropyranyloxy-2-(6-carbotetrahydropyranyloxy-5,5-dimethylhexyl)cyclopent-2-en-1-one | 5c | 11α,15-dihydroxy-3,3-dimethyl-9-oxo-16,16-trimethylene-13-cis-prostenoic acid |
| 263 | 4-tetrahydropyranyloxy-2-(6-carbotetrahydropyranyloxy-4-methyl-2-cis-hexenyl)cyclopent-2-en-1-one | 5c | 11α,15-dihydroxy-4-methyl-9-oxo-16,16-trimethylene-5-cis-13-cis-prostadienoic acid |
| 264 | 4-tetrahydropyranyloxy-2-(6-carbotetrahydropyranyloxy-5-oxa-hexyl)cyclopent-2-en-1-one | 5c | 11α,15-dihydroxy-3-oxa-9-oxo-16,16-trimethylene-13-cis-prostenoic acid |
| 265 | 4-tetrahydropyranyloxy-2-(6-carbotetrahydropyranyloxy-5,6-trans-methanohexyl)cyclopent-2-en-1-one | 5c | 11α,15-dihydroxy-2,3-trans-methano-9-oxo-16,16-trimethylene-13-cis-prostenoic acid |

REFERENCES:
<sup>a</sup>Belgian Patent 815,979 (Dec. 6, 1974); Derwent Central Patents Index, FARMDOC B - 88668V/52

EXAMPLE 266

4(R)-Tetrahydropyranyloxy-2-(6-carbomethoxyhexyl)-cyclopent-2-en-1-one

A vigorously stirred, ice-cold solution of 10 g. of 2-(6-carbomethoxyhexyl)-4(R)-hydroxy-cyclopent-2-en-1-one [R. Pappo, et al., Tetrahedron Letters, 943(1973)] and 15 g. of dihydropyran in 215 ml. of methylene chloride is treated with 85 mg. of p-toluenesulfonic acid monohydrate. After stirring for 5 minutes at 0° C. and 60 minutes at 25° C., the solution is poured into a stirred mixture of 40 ml. of saturated sodium chloride solution, 40 ml. of saturated sodium bicarbonate solution and 80 ml. of water. The organic phase is washed with brine, dried over magnesium sulfate, and concentrated to give an oil, $\lambda_{max}$ (film) 1730 (ester carbonyl), 1710 (ketone carbonyl), and 1030 cm$^{-1}$(tetrahydropyranyloxy group).

EXAMPLE 267

4(S)-Tetrahydropyranyloxy-2-(6-carboxyhexyl)-cyclopent-2-en-1-one

In the manner described in Example 266, treatment of 2-(6-carbomethoxyhexyl)-4(S)-hydroxycyclopent-2-en-1-one [R. Pappo, et al., Tetrahedron Letters, 943(1973)] with dihydropyran furnishes the subject product.

EXAMPLES 268–297

The product 1-9-oxo-11α,15-dihydroxy-16,16-trimethylene-13-trans-prostenoic acid methyl esters and the corresponding 15-enantiomers of Table X below are obtained by the procedure described in Example 201. In accordance with the process described therein, the starting trimethylsilyloxy substituted 1-alkenes listed in Table IX are treated with t-butyl-lithium providing the corresponding trimethylsilyl substituted trans-1-alkenyl lithium derivatives which on treatment with cuprous pentyne furnish the corresponding lithio pentynyl (trimethylsilyl substituted trans-1-alkenyl) cuprates, which in turn are treated with the 4-oxycyclopent-2-en-1-ones listed in the table. The resulting trimethylsilyl substituted -11α-tetrahydropyranyloxy-13-trans-prostenoic acid tetrahydropyranyl esters are hydrolyzed to the listed products by treatment with acetic acid-tetrahydrofuran-water.

TABLE X

| Example | Starting 4-oxy-cyclopent-2-en-1-one | Starting 1-iodo-1-trans-alkene of Example | Product 9-oxo-11α-hydroxy-13-trans-prostenoic acid methyl ester and the corresponding 15-enantiomer |
|---|---|---|---|
| 268 | 4(R)-tetrahydropyranyloxy-2-(6-carbomethoxy-2-cis-hexenyl)-cyclopent-2-en-1-one | 6 | l-methyl 11α,15-dihydroxy-9-oxo-16,16-trimethylene-5-cis,13-trans-prostadienoate |
| 269 | 4(R)-tetrahydropyranyloxy-2-(6-carbomethoxy-2-cis-hexenyl)-cyclopent-2-en-1-one | 40 | l-methyl 11α,15-dihydroxy-9-oxo-16,16-trimethylene-19-nor-5-cis,13-trans-prostadienoate |
| 270 | 4(R)-tetrahydropyranyloxy-2-(6-carbomethoxy-2-cis-hexenyl)-cyclopent-2-en-1-one | 41 | l-methyl 11α,15-dihydroxy-20-methyl-9-oxo-16,16-trimethylene-5-cis-13-transprostadienoate |
| 271 | 4(R)-tetrahydropyranyloxy-2-(6-carbomethoxy-2-cis-nexenyl)-cyclopent-2-en-1-one | 42 | l-methyl 20-ethyl-11α,15-dihydroxy-9-oxo-16,16-trimethylene-5-cis,13-trans-prostadienoate |
| 272 | 4(R)-tetrahydropyranyloxy-2-(6-carbomethoxy-2-cis-hexenyl)-cyclopent-2-en-1-one | 6a | l-methyl 11α,15-dihydroxy-9-oxo-16,16-tetramethylene-5-cis,13-trans-prostadienoate |
| 273 | 4(R)-tetrahydropyranyloxy-2-(6-carbomethoxy-2-cis-hexenyl)-cyclopent-2-en-1-one | 45 | l-methyl 11α,15-dihydroxy-9-oxo-16,16-trimethylene-5-cis,13-trans-prostadien-18-ynoate |
| 274 | 4(R)-tetrahydropyranyloxy-2-(6-carbomethoxy-2-cis-hexenyl)-cyclopent-2-en-1- | 46 | l-methyl 11α,15-dihydroxy-9-oxo-16,16-trimethylene-5-cis,13-trans,18-cis-prostarienoate |
| 275 | 4(R)-tetrahydropyranyloxy-2-(6-carbomethoxy-2-cis-hexenyl)-cyclopent-2-en-1-one | 43 | l-methyl 11α,15-dihydroxy-9-oxo-17-phenyl-16,16-trimethylene-5-cis,13-trans-prostadienoate |
| 276 | 4(R)-tetrahydropyranyloxy-2-(6-carbomethoxy-2-cis-hexenyl)cyclopent-2-en-1-one | 44 | l-methyl 18-cyclopentyl-11α,15-dihydroxy-9-oxo-16,16-trimethylene-19,20-dinor-5-cis,13-trans-prostadienoate |
| 277 | 4(R)-tetrahydropyranyloxy-2-(6-carbomethoxy-2-cis-hexenyl)-cyclopent-2-en-1-one | 5c | l-methyl 11α,15-dihydroxy-9-oxo-16,16-trimethylene-5-cis,13-cis-prostadienoate |
| 278 | 4(R)-tetrahydropyranyloxy-2-(6-carbomethoxyhexyl)-cyclopent-2-en-1-one (Example 266) | 6 | l-methyl 11α,15-dihydroxy-9-oxo-16,16-trimethylene-13-trans-prostenoate |
| 279 | 4(R)-tetrahydropyranyloxy-2-(6-carbomethoxyhexyl)-cyclopent-2-en-1-one(Example 266) | 40 | l-methyl 11α,15-dihyroxy-9-oxo-16,16-trimethylene-19-nor-13-trans-prostenoate |
| 280 | 4(R)-tetrahydropyranyloxy-2-(6-carbomethoxyhexyl)-cyclopent-2-en-1-one (Example 266) | 41 | l-methyl 11α,15-dihydroxy-20-methyl-9-oxo-16,16-trimethylene-13-trans-prostenoate |
| 281 | 4(R)-tetrahydropyranyloxy-2-(6-carbomethoxyhexyl)-cyclopent-2-en-1-one (Example 266) | 42 | l-methyl 20-ethyl-11α,15-dihydroxy-9-oxo-16,16-trimethylene-13-trans-prostenoate |
| 282 | 4(R)-tetrahydropyranyloxy-2- | 6a | l-methyl 11α,15-dihydroxy-9-oxo-16,16- |

TABLE X-continued

| Example | Starting 4-oxy-cyclopent-2-en-1-one | Starting 1-iodo-1-trans-alkene of Example | Product 9-oxo-11α-hydroxy-13-trans-prostenoic acid methyl ester and the corresponding 15-enantiomer |
|---|---|---|---|
| | (6-carbomethoxyhexyl)-cyclopent-2-en-1-one (Example 266) | | tetramethylene-13-trans-prostenoate |
| 283 | 4(R)-tetrahydropyranyloxy-2-(6-carbomethoxyhexyl)-cyclopent-2-en-1-one (Example 266) | 45 | l-methyl 11α,15-dihydroxy-9-oxo-16,16-trimethylene-13-trans-prosten-18-ynoate |
| 284 | 4(R)-tetrahydropyranyloxy-2-(6-carbomethoxyhexyl)-cyclopent-2-en-1-one (Example 266) | 46 | l-methyl 11α,15-dihydroxy-9-oxo-16,16-trimethylene-13-trans,18-cis-prostenoate |
| 285 | 4(R)-tetrahydropyranyloxy-2-(6-carbomethoxyhexyl)-cyclopent-2-en-1-one (Example 266) | 43 | l-methyl 11α,15-dihydroxy-9-oxo-17-phenyl-16,16-trimethylene-13-trans-prostenoate |
| 286 | 4(R)-tetrahydropyranyloxy-2(6-carbomethoxyhexyl)-cyclopent-2-en-1-one (Example 266) | 44 | l-methyl 18-cyclopentyl-11α,15-dihydroxy-9-oxo-16,16-trimethylene-19,20-dinor-13-trans-prostenoate |
| 287 | 4(R)-tetrahydropyranyloxy-2-(6-carbomethoxyhexyl)-cyclopent-2-en-1-one (Example 266) | 5c | l-methyl 11α,15-dihydroxy-9-oxo-16,16-trimethylene-13-cis-prostenoate |
| 288 | 4(S)-tetrahydropyranyloxy-2-(6-carbomethoxyhexyl)-cyclopent-2-en-1-one Example 267) | 6 | d-methyl 11α,15-dihydroxy-9-oxo-16,16-trimethylene-13-trans-prostenoate |
| 289 | 4(S)-tetrahydropyranyloxy-2-(6-carbomethoxyhexyl)-cyclopent-2-en-1-one (Example 267) | 40 | d-methyl 11α,15-dihydroxy-9-oxo-16,16-trimethylene-19-nor-13-trans-prostenoate |
| 290 | 4(S)-tetrahydropyranyloxy-2-(6-carbomethoxyhexyl)-cyclopent-2-en-1-one (Example 267) | 41 | d-methyl 11α,15-dihydroxy-20-methyl-9-oxo-16,16-trimethylene-13-trans-prostenoate |
| 291 | 4(S)-tetrahydropyranyloxy-2-(6-carbomethoxyhexyl)-cyclopent-2-en-1-one (Example 267) | 42 | d-methyl 20-ethyl-11α,15-dihydroxy-9-oxo-16,16-trimethylene-13-trans-prostenoate |
| 292 | 4(S)-tetrahydropyranyloxy-2-(6-carbomethoxyhexyl)-cyclopent-2-en-1-one (Example 267) | 6a | d-methyl 11α,15-dihydroxy-9-oxo-16,16-tetramethylene-13-trans-prostenoate |
| 293 | 4(S)-tetrahdropyranyloxy-2-(6-carbomethoxyhexyl)-cyclopent-2-en-1-one (Example 267) | 45 | d-methyl 11α,15-dihydroxy-9-oxo-16,16-trimethylene-13-trans-prosten-18-ynoate |
| 294 | 4(S)-tetrahydropyranyloxy-2-(6-carbomethoxyhexyl)-cyclopent-2-en-1-one (Example 267) | 46 | d-methyl 11α,15-dihydroxy-9-oxo-16,16-trimethylene-13-trans,18-cis-prostadienoate |
| 295 | 4(S)-tetrahydropyranyloxy-2-(6-carbomethoxyhexyl)-cyclopent-2-en-1-one (Example 267) | 43 | d-methyl 11α,15-dihydroxy-9-oxo-17-phenyl-16,16-trimethylene-13-trans-prostenoate |
| 296 | 4(S)-tetrahydropyranyloxy-2-(6-carbomethoxyhexyl)-cyclopent-2-en-1-one (Example 267) | 44 | d-methyl 18-cyclopentyl-11α,15-dihydroxy-9-oxo-16,16-trimethylene-19,20-dinor-13-trans-prostenoate |
| 297 | 4(S)-tetrahydropyranyloxy-2-(6-cabomethoxyhexyl)-cyclopent-2-en-1-one (Example 267) | 5c | d-methyl 11α,15-dihydroxy-9-oxo-16,16-trimethylene-13-cis-prostenoate |

EXAMPLE 298

9α,11α,15-Trihydroxy-16,16-trimethylene-5-cis,13-trans-prostenoic acid

To a stirred solution of 1 g. of 11α,15-dihydroxy-9-oxo-16,16-trimethylene-5-cis,13-trans-prostadienoic acid (Example 201) in 8 ml. of tetrahydrofuran is added 10 ml. of 0.65 M solution of lithium perhydro-9b-boraphenalyl hydride in tetrahydrofuran at −78° C. under argon. The solution is stirred at −78° C. for 45 minutes and at ambient temperature for 15 minutes. The solution is diluted with 10 ml. of water and extracted with ether. The extract is back-extracted with N/4 sodium bicarbonate solution. The combined aqueous extracts are acidified with 4 N hydrochloric acid, saturated with sodium chloride and extracted with ether. The extract is washed with saturated sodium chloride solution, dried over magnesium sulfate, and taken to dryness. The residue is purified by column chromatography to give the product as a colorless oil.

EXAMPLES 299–476

Reduction of the 9-oxo derivatives listed in TABLE XI below with lithium perhydro-9b-boraphenalyl hydride by the method described in Example 298 is productive of the 9α-hydroxy derivatives described in the table.

| Example | Starting 9-oxo-derivative of Example | Product 9α-hydroxy derivative |
|---|---|---|
| 299 | 125 | 9α,15-dihydroxy-16,16-trimethylene-7-nor-13-trans-prostenic acid |
| 299a | 8 | 9α,15-dihydroxy-16,16-trimethylene-13-trans-prostenoic acid |
| 300 | 125a | 9α,15-dihydroxy-16,16-trimethylene-7a-homo-13-trans-prostenoic acid |
| 301 | 125b | 9α,15-dihydroxy-16,16-trimethylene-7a,7b-bishomo-13-trans-prostenoic acid |
| 302 | 126 | 9α,15-dihydroxy-2-methyl-16,16-trimethylene-13-trans-prostenoic acid |
| 303 | 127 | 2-ethyl-9α,15-dihydroxy-16,16-trimethylene-13-trans-prostenoic acid |
| 304 | 128 | 9α,15-dihydroxy-2,3-trans-methano-16,16-trimethylene-13-trans-prostenoic acid |
| 305 | 129 | 9α,15-dihydroxy-3,3-dimethyl-16,16-trimethylene-13-trans-prostenoic acid |
| 306 | 130 | 9α,15-dihydroxy-3-oxa-16,16-trimethylene-13-trans-prostenoic acid |
| 307 | 131 | 9α,15-dihydroxy-3-thia-16,16-trimethylene-13-trans-prostenoic acid |
| 308 | 132 | 9α,15-dihydroxy-2-phenyl-16,16-trimethylene-13-trans-prostenoic acid |
| 309 | 133 | 9α,15-dihydroxy-3-thia-16,16-trimethylene-7a-homo-13-trans-prostenoic acid |
| 310 | 134 | 9α,15-dihydroxy-16,16-trimethylene-5-cis,13-trans-prostadienoic acid |
| 311 | 135 | 9α,15-dihydroxy-16,16-trimethylene-7-nor-5-cis-13-trans-prostadienoic acid |
| 312 | 136 | 9α,15-dihydroxy-16,16-trimethylene-7a-homo-5-cis,13-trans-prostadienoic acid |
| 313 | 137 | 9α,15-dihydroxy-4-methyl-16,16-trimethylene-5-cis,13-trans-prostadienoic acid |
| 314 | 138 | 4-ethyl-9α,15-dihdroxy-16,16-trimethylene-5-cis,13-trans-prostadienoic acid |
| 315 | 139 | 9α,15-dihydroxy-4-propyl-16,16-trimethylene-5-cis,13-trans-prostadienoic acid |
| 316 | 140 | 9α,15-dihydroxy-4(R)-methyl-16,16-trimethylene-5-cis,13-trans-prostadienoic acid |
| 317 | 140a | 9α,15-dihydroxy-16,16,trimethylene-19-nor-13-trans-prostenoic acid |
| 318 | 141 | 9α,15-dihydroxy-16,16-trimethylene-7,19-dinor-13-trans-prostenoic acid |
| 319 | 142 | 9α,15-dihydroxy-2-methyl-16,16-trimethylene-19-nor-13-trans-prostenoic acid |
| 320 | 143 | 9α,15-dihydroxy-2,3-trans-methano-20-methyl-16,16-trimethylene-13-trans-prostenoic acid |
| 321 | 143a | 9α,15-dihydroxy-20-methyl-16,16-trimethylene-13-trans-prostenoic acid |
| 322 | 144 | 9α,15-dihydroxy-3,3,20-trimethyl-16,16-trimethylene-13-trans-prostenoic acid |
| 323 | 145 | 9α,15-dihydroxy-20-methyl-3-oxa-16,16-trimethylene-13-trans-prostenoic acid |
| 324 | 146 | 20-ethyl-9α,15-dihydroxy-2-phenyl-16,16-trimethylene-13-trans-prostenoic acid |
| 325 | 146a | 20-ethyl-9α,15-dihydroxy-16,16-trimethylene-13-trans-prostenoic acid |
| 326 | 147 | 20-ethyl-9α,15-dihydroxy-16,16-trimethylene-5-cis,13-trans-prostadienoic acid |
| 327 | 148 | 20-ethyl-9α,15-dihydroxy-4-methyl-16,16-trimethylene-5-cis,13-trans-prostenoic acid |
| 328 | 149 | 9α,15-dihydroxy-16,16-tetramethylene-13-trans-prostenoic acid |
| 329 | 150 | 9α,15-dihydroxy-16,16-tetramethylene-7a,7b-bishomo-13-trans-prostenoic acid |
| 330 | 151 | 9α,15-dihydroxy-2-methyl-16,16-tetramethylene-13-trans-prostenoic acid |
| 331 | 152 | 9α,15-dihydroxy-2,3-trans-methano-16,16-tetramethylene-13-trans-prostenoic acid |
| 332 | 153 | 9α,15-dihydroxy-3,3-dimethyl-16,16-tetramethylene-13-trans-prostenoic acid |
| 333 | 154 | 9α,15-dihydroxy-2-phenyl-16,16-tetramethylene-13-trans-prostenoic acid |
| 334 | 155 | 9α,15-dihydroxy-3-oxa-16,16-tetramethylene-13-trans-prostenoic acid |
| 335 | 156 | 9α,15-dihydroxy-16,16-tetramethylene-9-thia-13-trans-prostenoic acid |
| 336 | 157 | 9α,15-dihydroxy-16,16-tetramethylene-5-cis,13-trans-prostadienoic |

-continued

| Example | Starting 9-oxo-derivative of Example | Product 9α-hydroxy derivative |
|---|---|---|
| 337 | 158 | 9α,15-dihydroxy-4-ethyl-16,16-tetramethylene-5-cis-13-trans-prostadienoic acid |
| 338 | 159 | 9α,15-dihydroxy-16,16-trimethylene-13-trans-prosten-18-ynoic acid |
| 339 | 160 | 9α,15-dihydroxy-16,16-trimethylene-7-nor-13-trans-prosten-18-ynoic acid |
| 340 | 161 | 9α,15-dihydroxy-2-methyl-16,16-trimethyelene-13-trans-prosten-18-ynoic acid |
| 341 | 162 | 9α,15-dihydroxy-3,3-dimethyl-16,16-trimethylene-13-trans-prosten-18-ynoic acid |
| 342 | 163 | 9α,15-dihydroxy-3-oxa-16,16-trimethylene-13-trans-prosten-18-ynoic acid |
| 343 | 164 | 9α,15-dihydroxy-3-thia-16,16-trimethylene-13-trans-prosten-18-ynoic acid |
| 344 | 165 | 9α,15-dihydroxy-2-phenyl-16,16-trimethylene-13-trans-prosten-18-ynoic acid |
| 345 | 166 | 9α,15-dihydroxy-16,16-trimethylene-5-cis,13-trans-prostadien-18-ynoic acid |
| 346 | 167 | 9α14-dihydroxy-4-methyl-16,16-trimethylene-5-cis,13-trans-prostadien-18-ynoic acid |
| 347 | 168 | 9α,15-dihydroxy-16,16-trimethylene-13-trans,18-cis-prostadienoic acid |
| 348 | 169 | 9α,15-dihydroxy-16,16-trimethylene-7a-homo-13-trans,18-cis-prostadienoic acid |
| 349 | 170 | 2-ethyl-9α,15-dihydroxy-16,16-trimethylene-13-trans,18-cis-prostadienoic acid |
| 350 | 171 | 9α,15-dihydroxy-2,3-trans-methano-16,16-trimethylene-13-trans-18-cis-prostadienoic acid |
| 351 | 172 | 9α,15-dihydroxy-3-oxa-16,16-trimethylene-13-trans,18-cis-prostadienoic acid |
| 352 | 173 | 9α,15-dihydroxy-2-phenyl-16,16-trimethylene-13-trans,18-cis-prostadienoic acid |
| 353 | 174 | 9α,15-dihydroxy-3-thia-16,16-trimethylene-7a-homo-13-trans,18-cis-prostadienoic acid |
| 354 | 175 | 9α,15-dihydroxy-16,16-trimethylene-5-cis,13-trans,18-cis-prostatrienoic acid |
| 355 | 176 | 9α,15-dihydroxy-4-methyl-16,16-trimethylene-5-cis,13-trans,18-cis-prostatrienoic acid |
| 356 | 177 | 9α,15-dihydroxy-17-phenyl-16,16-trimethylene-18,19,20-trinor-13-trans-prostenoic acid |
| 357 | 178 | 2-ethyl-9α,15-dihydroxy-17-phenyl-16,16-trimethylene-18,19,20-trinor-13-trans-prostenoic acid |
| 358 | 179 | 9α,15-dihydroxy-2,17-diphenyl-16,16-trimethylene-18,19,20-trinor-13-trans-prostenoic acid |
| 359 | 180 | 9α,15-dihydroxy-17-phenyl-16,16-trimethylene-18,19,20-trinor-5-cis,13-trans-prostadienoic acid |
| 360 | 181 | 9α,15-dihydroxy-4-methyl-17-phenyl-16,16-trimethylene-18,19,20-trinor-5-cis,13-trans-prostadienoic acid |
| 361 | 182 | 9α,15-dihydroxy-17-phenyl-3-thia-16,16-trimethylene-18,19,20-trinor-13-trans-prostenoic acid |
| 362 | 183 | 9α,15-dihydroxy-2,3-trans-methano-17-phenyl-16,16-trimethylene-18,19,20-trinor-13-trans-prostenoic acid |
| 363 | 184 | 18-cyclopentyl-9α,15-dihydroxy-16,16-trimethylene-19,20-dinor-13-trans-prostenoic acid |
| 364 | 185 | 18-cyclopentyl-9α,15-dihydroxy-3,3-dimethyl-16,16-trimethylene-19,20-dinor-13-trans-prostenoic acid |
| 365 | 186 | 18-cyclopentyl-15-hydroxy-2-phenyl-16,16-trimethylene-19,20-dinor-13-trans-prostenoic acid |
| 366 | 187 | 18-cyclopentyl-9α,15-dihydroxy-16,16-trimethylene-19,20-dinor-5-cis,13-trans-prostadienoic acid |
| 367 | 188 | 18-cyclopentyl-9α,15-dihydroxy-4-propyl-16,16-trimethylene-19,20-dinor-5-cis,13-trans-prostadienoic acid |
| 368 | 189 | 18-cyclopentyl-9α,15-dihydroxy-3-oxa-16,16-trimethylene-19,20-dinor-13-trans-prostenoic acid |
| 369 | 190 | 18-cyclopentyl-9α,15-dihydroxy-3-thia-16,16-trimethylene-19,20-dinor-13-trans-prostenoic acid |
| 370 | 191 | 18-cyclopentyl-9α,15-dihydroxy-2,3-trans-methano-16,16-trimethylene-18,20-dinor-13-trans-prostenoic acid |
| 371 | 192 | 9α,15-dihydroxy-16,16-trimethylene-13-cis-prostenoic acid |
| 372 | 193 | 9α,15-dihydroxy-16,16-trimethylene-7a,7b-bishomo-13-cis-prostenoic acid |
| 373 | 194 | 9α,15-dihydroxy-2-methyl-16,16-trimethylene-13-cis-prostenoic acid |
| 374 | 195 | 9α,15-dihydroxy-3,3-dimethyl-16,16-trimethylene-13-cis-prostenoic acid |
| 375 | 196 | 9α,15-dihydroxy-2-phenyl-16,16-trimethylene-13-cis-prostenoic acid |
| 376 | 197 | 9α,15-dihydroxy-16,16-trimethylene-5-cis,13-cis-prostadienoic acid |

-continued

| Example | Starting 9-oxo-derivative of Example | Product 9α-hydroxy derivative |
|---|---|---|
| 377 | 198 | 9α,15-dihydroxy-4-methyl-16,16-trimethylene-5-cis,13-cis-prostadienoic acid |
| 378 | 199 | 9α,15-dihydroxy-3-oxa-16,16-trimethylene-5-cis,13-cis-prostadienoic acid |
| 379 | 200 | 9α,15-dihydroxy-2,3-trans-methano-16,16-trimethylene-5-cis,13-cis-prostadienoic acid |
| 380 | 201 | 9α,11α,15-trihydroxy-16,16-trimethylene-5-cis,13-trans-prostadienoic acid |
| 381 | 202 | 9α,11α,15-trihydroxy-16,16-trimethylene-13-trans-prostenoic acid |
| 382 | 203 | 9α,11α,15-trihydroxy-16,16-trimethylene-7-nor-13-trans-prostenoic acid |
| 383 | 204 | 9α,11α,15-trihydroxy-16,16-trimethylene-7-homo-13-trans-prostenoic acid |
| 384 | 205 | 9α,11α,15-trihydroxy-16,16-trimethylene-7a,7b-bishomo-13-trans-prostenoic acid |
| 385 | 206 | 9α,11α,15-trihydroxy-2-methyl-16,16-trimethylene-13-trans-prostenoic acid |
| 386 | 207 | 2-ethyl-9α,11α,15-trihydroxy--16,16-trimethylene-13-trans-prostenoic acid |
| 387 | 208 | 9α,11α,15-trihydroxy-3,3-dimethyl-16,16-tetramethylene-13-trans-prostenoic acid |
| 388 | 209 | 9α,11α,15-trihydroxy-16,16-trimethylene-7-nor-5-cis,13-trans-prostadienoic acid |
| 389 | 210 | 9α,11α,15-trihydroxy-16,16-trimethylene-7a-homo-5-cis,13-trans-prostadienoic acid |
| 390 | 211 | 9α,11α,15-trihydroxy-4-methyl-16,16-trimethylene-5-cis,13-trans-prostadienoic acid |
| 391 | 212 | 9α,11α,15-trihydroxy-4(R)-methyl-16,16-trimethylene-5-cis,13-trans-prostadienoic acid |
| 392 | 213 | 4-ethyl-9α,11α,15-trihydroxy-16,16-trimethylene-5-cis,13-trans-prostadienoic acid |
| 393 | 214 | 9α,11α,15-trihydroxy-4-propyl-16,16-trimethylene-5-cis,13-trans-prostadienoic acid |
| 394 | 215 | 9α,11α,15-trihydroxy-16,16-trimethylene-19-nor-13-trans-prostenoic acid |
| 395 | 216 | 9α,11α,15-trihydroxy-16,16-trimethylene-7a,7b-bishomo-19-nor-13-trans-prostenoic acid |
| 396 | 216a | 9α,11α,15-trihydroxy-16,16-trimethylene-5-cis,13-trans-19-nor-prostadienoic acid |
| 397 | 217 | 9α,11α,15-trihydroxy-20-methyl-9-oxo-16,16-trimethylene-13-trans-prostenoic acid |
| 398 | 218 | 9α,11α,15-trihydroxy-2,20-dimethyl-16,16-trimethylene-13-trans-prostenoic acid |
| 399 | 219 | 9α,11α,15-trihydroxy-20-methyl-16,16-trimethylene-5-cis,13-trans-prostadienoic acid |
| 400 | 220 | 9α,11α,15-trihydroxy-20-methyl-16,16-trimethylene-7a-homo-5-cis,13-trans-prostadienoic acid |
| 401 | 221 | 20-ethyl-9α,11α,15-trihydroxy-16,16-trimethylene-13-trans-prostenoic acid |
| 402 | 222 | 20-ethyl-9α,11α,15-trihydroxy-16,16-trimethylene-5-cis,13-trans-prostadienoic acid |
| 403 | 222a | 20-ethyl-9α,11α,15-trihydroxy-4-methyl-16,16-trimethylene-5-cis,13-trans-prostadienoic acid |
| 404 | 223 | 9α,11α,15-trihydroxy-16,16-tetramethylene-13-trans-prostenoic acid |
| 405 | 224 | 9α,11α,15-trihydrocy-16,16-tetramethylene-5-cis,13-trans-prostadienoic acid |
| 406 | 225 | 9α,11α,15-trihydroxy-16,16-tetramethylene-7-nor-13-trans-prostenoic acid |
| 407 | 226 | 2-ethyl-9α,11α,15-trihydroxy-16,16-tetramethylene-13-trans-prostenoic acid |
| 408 | 227 | 9α,11α,15-trihydroxy-3,3-dimethyl-16,16-tetramethylene-13-trans-prostenoic acid |
| 409 | 228 | 9α,11α,15-trihydroxy-4-methyl-16,16-tetramethylene-5-cis,13-trans-prostadienoic acid |
| 410 | 229 | 9α,11α,15-trihydroxy-3-oxa-16,16-tetramethylene-13-trans-prostenoic acid |
| 411 | 230 | 9α,11α,15-trihydroxy-2,3-trans-methano-16,16-tetramethylene-13-trans-prostenoic acid |
| 412 | 231 | 9α,11α,15-trihydroxy-16,16-trimethylene-13-trans-prosten-18-ynoic acid |
| 413 | 232 | 9α,11α,15-trihydroxy-16,16-trimethylene-5-cis,13-trans-prostadien-18-ynoic acid |
| 414 | 233 | 9α,11α,15-trihydroxy-16,16-trimethylene-7a,7b-bishomo-13-trans-prosten-18-ynoic acid |
| 415 | 234 | 9α,11α,15-trihydroxy-2-methyl-16,16-trimethylene-13-trans-prosten-18-ynoic acid |
| 416 | 235 | 9α,11α,15-trihydroxy-16,16-trimethylene-7a-homo-5-cis,13-trans-prostadien-18-ynoic acid |

-continued

| Example | Starting 9-oxo-derivative of Example | Product 9α-hydroxy derivative |
|---|---|---|
| 417 | 236 | 9α,11α,15-trihydroxy-4-methyl-16,16-trimethylene-5-cis,13-trans-prostadien-18-ynoic acid |
| 418 | 237 | 9α,11α,15-trihydroxy-3-oxa-16,16-trimethylene-13-trans-prosten-18-ynoic acid |
| 419 | 238 | 9α,11α,15-trihydroxy-2,3-trans-methano-16,16-trimethylene-13-trans-prosten-18-ynoic acid |
| 420 | 239 | 9α,11α,15-trihydroxy-16,16-trimethylene-13-trans,18-cis-prostadienoic acid |
| 421 | 240 | 9α,11α,15-trihydroxy-16,16-trimethylene-5-cis,13-trans,18-cis-prostatrienoic acid |
| 422 | 241 | 9α,11α,15-trihydroxy-17-phenyl-16,16-trimethylene-18,19,20-trinor-13-trans-prostenoic acid |
| 423 | 242 | 9α,11α,15-trihydroxy-17-phenyl-16,16-trimethylene-18,19,20-trinor-5-cis,13-trans-prostadienoic acid |
| 424 | 243 | 9α,11α,15-trihydroxy-17-phenyl-16,16-trimethylene-7a-homo-18,19,20-trinor-13-trans-prostenoic acid |
| 425 | 244 | 9α,11α,15-trihydroxy-2-ethyl-17-phenyl-16,16-trimethylene-18,19,20-trinor-13-trans-prostenoic acid |
| 426 | 245 | 9α,11α,15-trihydroxy-17-phenyl-4-propyl-16,16-trimethylene-18,19,20-trinor-4-cis-13-trans-prostadienoic acid |
| 427 | 246 | 9α,11α,15-trihydroxy-3-oxa-17-phenyl-16,16-trimethylene-18,19-20-trinor-13-trans-prostenoic acid |
| 428 | 247 | 9α,11α,15-trihydroxy-2,3-trans-methano-17-phenyl-16,16-trimethylene-18,19,20-trinor-13-trans-prostenoic acid |
| 429 | 248 | 9α,11α,15-trihydroxy-3,3-dimethyl-17-phenyl-16,16-trimethylene-18,19,20-trinor-13-trans-prostenoic acid |
| 430 | 249 | 18-cyclopentyl-9α,11α,15-trihydroxy-16,16-trimethylene-19,20-dinor-13-trans-prostenoic acid |
| 431 | 250 | 18-cyclopentyl-9α,11α,15-trihydroxy-9-oxo-16,16-trimethylene-19,29-dinor-5-cis,13-trans-prostadienoic acid |
| 432 | 251 | 18-cyclopentyl-9α,11α,15-trihydroxy-16,16-trimethylene-7,19,20-trinor-13-trans-prostenoic acid |
| 433 | 252 | 18-cyclopentyl-2-ethyl-9α,11α,15-trihydroxy-16,16-trimethylene-19,20-dinor-13-trans-prostenoic acid |
| 434 | 253 | 18-cyclopentyl-9α,11α,15-trihydroxy-3,3-dimethyl-16,16-trimethylene-19,20-dinor-13-trans-prostenoic acid |
| 435 | 254 | 18-cyclopentyl-9α,11α,15-trihydroxy-16,16-trimethylene-7a-homo-19,20-dinor-5-cis,13-trans-prostadienoic acid |
| 436 | 255 | 18-cyclopentyl-9α,11α,15-trihydroxy-4-methyl-16,16-trimethylene-19,20-dinor-5-cis,13-trans-prostadienoic acid |
| 437 | 256 | 18-cyclopentyl-9α,11α,15-trihydroxy-3-oxa-16,16-trimethylene-19,20-dinor-13-trans-prostenoic acid |
| 438 | 257 | 18-cyclopentyl-9α,11α,15-trihydroxy-2,3-trans-methano-16,16-trimethylene-19,20-dinor-13-trans-prostenoic acid |
| 439 | 258 | 9α,11α,15-trihydroxy-16,16-trimethylene-13-cis-prostenoic acid |
| 440 | 259 | 9α,11α,15-trihydroxy-16,16-trimethylene-5-cis,13-cis-prostadienoic acid |
| 441 | 260 | 9α,11α,15-trihydroxy-16,16-trimethylene-7a,7b-bishomo-13-cis-prostenoic acid |
| 442 | 261 | 9α,11α,15-trihydroxy-2-methyl-16,16-trimethylene-13-cis-prostenoic acid |
| 443 | 262 | 9α,11α,15-trihydroxy-3,3-dimethyl-16,16-trimethylene-13-cis-prostenoic acid |
| 444 | 263 | 9α,11α,15-trihydroxy-4-methyl-16,16-trimethylene-5-cis,13-cis-prostadienoic acid |
| 445 | 264 | 9α,11α,15-trihydroxy-3-oxa-16,16-trimethylene-13-cis-prostenoic acid |
| 446 | 265 | 9α,11α,15-trihydroxy-2,3-trans-methano-16,16-trimethylene-13-cis-prostenoic acid |
| 447 | 268 | l-methyl 9α,11α,15-trihydroxy-16,16-trimethylene-5-cis,13-trans-prostadienoate |
| 448 | 269 | l-methyl 9α,11α,15-trihydroxy-16,16-trimethylene-19-nor-5-cis,13-trans-prostadienoate |
| 449 | 270 | l-methyl 9α,11α,15-trihydroxy-20-methyl-16,16-trimethylene-5-cis,13-trans-prostadienoate |
| 450 | 271 | l-methyl 20-ethyl-9α,11α,15-trihydroxy-16,16-trimethylene-5-cis,13-trans-prostadienoate |
| 451 | 272 | l-methyl 9α,11α,15-trihydroxy-16,16-tetramethylene-5-cis,13-trans-prostadienoate |
| 452 | 273 | l-methyl 9α,11α,15-trihydroxy-16,16-trimethylene-5-cis,13-trans-prostadien-18-ynoate |
| 453 | 274 | l-methyl 9α,11α,15-trihydroxy-16,16-trimethylene-5-cis,13-trans,18-cis-prostatrienoate |
| 454 | 275 | l-methyl 9α,11α,15-trihydroxy-17-phenyl-16,16-trimethylene-5-cis,13-trans-prostadienoate |
| 455 | 276 | l-methyl 18-cyclopentyl-9α,11α,15-trihydroxy-16,16-trimethylene-19,20-dinor-5-cis,13-trans-prostadienoate |
| 456 | 277 | l-methyl 9α,11α,15-trihydroxy-16,16-trimethylene-5-cis,13-cis-prostadienoate |

-continued

| Example | Starting 9-oxo-derivative of Example | Product 9α-hydroxy derivative |
|---|---|---|
| 457 | 278 | l-methyl 9α,11α,15-trihydroxy-16,16-trimethylene-13-trans-prostenoate |
| 458 | 279 | l-methyl 9α,11α,15-trihydroxy-16,16-trimethylene-19-nor-13-trans-prostenoate |
| 459 | 280 | l-methyl 9α,11α,15-trihydroxy-20-methyl-16,16-trimethylene-13-trans-prostenoate |
| 460 | 281 | l-methyl 20-ethyl-9α,11α,15-trihydroxy-16,16-trimethylene-13-trans-prostenoate |
| 461 | 282 | l-methyl 9α,11α,15-trihydroxy-16,16-tetramethylene-13-trans-prostenoate |
| 462 | 283 | l-methyl 9α,11α,15-trihydroxy-16,16-trimethylene-13-trans-prosten-18-ynoate |
| 463 | 284 | l-methyl 9α,11α,15-trihydroxy-16,16-trimethylene-13-trans,18-cis-prostenoate |
| 464 | 285 | l-methyl 9α,11α,15-trihydroxy-17-phenyl-16,16-trimethylene-13-trans-prostenoate |
| 465 | 286 | l-methyl 18-cyclopentyl-9α,11α,15-trihydroxy-16,16-trimethylene-19,20-dinor-13-trans-prostenoate |
| 466 | 287 | l-methyl 9α,11α,15-trihydroxy-16,16-trimethylene-13-cis-prostenoate |
| 467 | 288 | d-methyl 9α,11α,15-trihydroxy-16,16-trimethylene-13-trans-prostenoate |
| 468 | 289 | d-methyl 9α,11α,15-trihydroxy-16,16-trimethylene-19-nor-13-trans-prostenoate |
| 469 | 290 | d-methyl 9α,11α,15-trihydroxy-20-methyl-16,16-trimethylene-13-trans-prostenoate |
| 470 | 291 | d-methyl 20-ethyl-9α,11α,15-trihydroxy-16,16-trimethylene-13-trans-prostenoate |
| 471 | 292 | d-methyl 9α,11α,15-trihydroxy-16,16-tetramethylene-13-trans-prostenoate |
| 472 | 293 | d-methyl 9α,11α,15-trihydroxy-16,16-trimethylene-13-trans-prosten-18-ynoate |
| 473 | 294 | d-methyl 9α,11α,15-trihydroxy-16,16-trimethylene-13-trans,18-cis-prostadienoate |
| 474 | 295 | d-methyl 9α,11α,15-trihydroxy-17-phenyl-16,16-trimethylene-13-trans-prostenoate |
| 475 | 296 | d-methyl 18-cyclopentyl-9α,11α,15-trihydroxy-16,16-trimethylene-19,20-dinor-13-trans-prostenoate |
| 476 | 297 | d-methyl 9α,11α,15-trihydroxy-16,16-trimethylene-13-cis-prostenoate |

EXAMPLE 477

9β,11α-15-Trihydroxy-16,16-trimethylene-5-cis,13-trans-prostadienoic acid

To a stirred, ice cold solution of 1.1 g. of 11α,15-dihydroxy-9-oxo-16,16-trimethylene-5-cis, 13-trans-prostadienoic acid (Example 201) in 100 ml. of ethanol is added 1 g. of sodium borohydride in small portions during 1 minute. The mixture is stirred at 0° C. for 5 minutes and at ambient temperature for 1.5 hours. The bulk of the ethanol is evaporated at room temperature, and the residue is treated with ether followed by dilute hydrochloric acid while cooling in an ice bath. The organic phase is separated and washed with water and saturated sodium chloride solution. The solution is dried with anhydrous magnesium sulfate and taken to dryness. The material was chromatographed on silica gel to furnish the subject product as well as the α-epimer.

EXAMPLES 478–566

Treatment of the 9-oxo derivatives listed in Table XII below with sodium borohydride in accordance with the procedure described in Example 477 is productive of the 9β-hydroxy derivatives of the table. The corresponding 9α-epimers are also obtained.

TABLE XII

| Example | Starting 9-oxo-derivatives of Example | Product 9β-hydroxy-derivative |
|---|---|---|
| 478 | 125 | 9β,15-dihydroxy-16,16-trimethylene-7-nor-13-trans-prostenoic acid |
| 479 | 8 | 9β,15-dihydroxy-16,16-trimethylene-13-trans-prostenoic acid |
| 480 | 126 | 9β,15-dihydroxy-2-methyl-16,16-trimethylene-13-trans-prostenoic acid |
| 481 | 127 | 2-ethyl-9β,15-dihydroxy-16,16-trimethylene-13-trans-prostenoic acid |
| 482 | 128 | 9β,15-dihydroxy-2,3-trans-methano-16,16-trimethylene-13-trans-prostenoic acid |
| 483 | 129 | 9β,15-dihydroxy-3,3-dimethyl-16,16-trimethylene-13-trans-prostenoic acid |
| 484 | 130 | 9β,15-dihydroxy-3-oxa-16,16-trimethylene-13-trans-prostenoic acid |
| 485 | 131 | 9β,15-dihydroxy-3-thia-16,16-trimethylene-13-trans-prostenoic acid |
| 486 | 132 | 9β,15-dihydroxy-2-phenyl-16,16-trimethylene-13-trans-prostenoic acid |
| 487 | 134 | 9β,15-dihydroxy-16,16-trimethylene-5-cis,13-trans-prostadenoic |

TABLE XII-continued

| Example | Starting 9-oxo-derivatives of Example | Product 9β-hydroxy-derivative |
|---|---|---|
| | | acid |
| 488 | 137 | 9β,15-dihydroxy-4-methyl-16,16-trimethylene-5-cis,13-trans-prostadienoic acid |
| 489 | 139 | 9β,15-dihydroxy-4-propyl-16,16-trimethylene-5-cis,13-trans-prostadienoic acid |
| 490 | 143 | 9β,15-dihydroxy-2,3-trans-methano-20-methyl-16,16-trimethylene-13-trans-prostenoic acid |
| 491 | 143a | 9β,15-dihydroxy-20-methyl-16,16-trimethylene-13-trans-prostenoic acid |
| 492 | 146a | 20-ethyl-9β,15-dihydroxy-16,16-trimethylene-13-trans-prostenoic acid |
| 493 | 147 | 20-ethyl-9β,15-dihydroxy-16,16-trimethylene-5-cis,13-trans-prostadienoic acid |
| 494 | 149 | 9β,15-dihydroxy-16,16-tetramethylene-13-trans-prostenoic acid |
| 495 | 151 | 9β,15-dihydroxy-2-methyl-16,16-tetramethylene-13-trans-prostenoic acid |
| 496 | 157 | 9β,15-dihydroxy-16,16-tetramethylene-5-cis,13-trans-prostadienoic acid |
| 497 | 159 | 9β,15-dihydroxy-16,16-trimethylene-13-trans-prosten-18-ynoic acid |
| 498 | 168 | 9β,15-dihydroxy-16,16-trimethylene-13-trans,18-cis-prostadienoic acid |
| 499 | 173 | 9β,15-dihydroxy-2-phenyl-16,16-trimethylene-13-trans,18-cis-prostadienoic acid |
| 500 | 175 | 9β,15-dihydroxy-16,16-trimethylene-5-cis,13-trans,18-cis-prostatrienoic acid |
| 501 | 181 | 9β,15-dihydroxy-4-methyl-17-phenyl-16,16-trimethylene-18,19,20-trinor-5-cis,13-trans-prostadienoic acid |
| 502 | 183 | 9β,15-dihydroxy-2,3-trans-methano-17-phenyl-16,16-trimethylene-18,19,20-trinor-13-trans-prostenoic acid |
| 503 | 192 | 9β,15-dihydroxy-16,16-trimethylene-13-cis-prostenoic acid |
| 504 | 194 | 9β,15-dihydroxy-2-methyl-16,16-trimethylene-13-cis-prostenoic acid |
| 505 | 196 | 9β,15-dihydroxy-2-phenyl-16,16-trimethylene-13-cis-prostenoic acid |
| 506 | 197 | 9β,15-dihydroxy-16,16-trimethylene-5-cis,13-cis-prostadienoic acid |
| 507 | 199 | 9β,15-dihydroxy-3-oxa-16,16-trimethylene-5-cis,13-cis-prostadienoic acid |
| 508 | 200 | 9β,15-dihydroxy-2,3-trans-methano-16,16-trimethylene-5-cis,13-cis-prostadienoic acid |
| 509 | 201 | 9β,11α,15-trihydroxy-16,16-trimethylene-5-cis,13-trans-prostadienoic acid |
| 510 | 202 | 9β,11α,15-trihydroxy-16,16-trimethylene-13-trans-prostenoic acid |
| 511 | 206 | 9β,11α,15-trihydroxy-2-methyl-16,16-trimethylene-13-trans-prostenoic acid |
| 512 | 207 | 2-ethyl-9β,11α,15-trihydroxy-16,16-trimethylene-13-trans-prostenoic acid |
| 513 | 208 | 9β,11α,15-trihydroxy-3,3-dimethyl-16,16-tetramethylene-13-trans-prostenoic acid |
| 514 | 211 | 9α,11α,15-trihydroxy-4-methyl-16,16-trimethylene-5-cis,13-trans-prostadienoic acid |
| 515 | 217 | 9β,11α,15-trihydroxy-20-methyl-16,16-trimethylene-13-trans-prostenoic acid |
| 516 | 219 | 9β,11α,15-trihydroxy-20-methyl-16,16-trimethylene-5-cis,13-trans-prostadienoic acid |
| 517 | 222 | 20-ethyl-9β,11α,15-trihydroxy-16,16-trimethylene-5-cis,13-trans-prostadienoic acid |
| 518 | 223 | 9β,11α,15-trihydroxy-16,16-tetramethylene-13-trans-prostenoic acid |
| 519 | 226 | 2-ethyl-9β,11α,15-trihydroxy-16,16-tetramethylene-13-trans-prostenoic acid |
| 520 | 227 | 9β,11α,15-trihydroxy-3,3-dimethyl-16,16-tetramethylene-13-trans-prostenoic acid |
| 521 | 228 | 9β,11α,15-trihydroxy-4-methyl-16,16-tetramethylene-2-cis,13-trans-prostadienoic acid |
| 522 | 229 | 9β,11α,15-trihydroxy-3-oxa-16,16-tetramethylene-13-trans-prostenoic acid |
| 523 | 231 | 9β,11α,15-trihydroxy-16,16-trimethylene-13-trans-prosten-18-ynoic acid |
| 524 | 232 | 9β,11α,15-trihydroxy-16,16-trimethylene-5-cis,13-trans-prostadien-18-ynoic acid |
| 525 | 234 | 9β,11α,15-trihydroxy-2-methyl-16,16-trimethylene-13-trans-prosten-18-ynoic acid |
| 526 | 236 | 9β,11α,15-trihydroxy-4-methyl-16,16-trimethylene-5-cis,13-trans-prostadien-18-ynoic acid |
| 527 | 237 | 9β,11α,15-trihydroxy-3-oxa-16,16-trimethylene-13-trans-prosten-18-ynoic acid |
| 528 | 238 | 9β,11α,15-trihydroxy-2,3-methano-16,16-trimethylene-13-trans-prosten-18-ynoic acid |
| 529 | 239 | 9β,11α,15-trihydroxy-16,16-trimethylene-13-trans,18-cis-prostadienoic acid |
| 530 | 240 | 9β,11α,15-trihydroxy-16,16-trimethylene-5-cis,13-trans,18-cis-prostatrienoic acid |

TABLE XII-continued

| Example | Starting 9-oxo-derivatives of Example | Product 9β-hydroxy-derivative |
|---|---|---|
| 531 | 245 | 9β,11α,15-trihydroxy-17-phenyl-4-propyl-16,16-trimethylene-18,19,-20-trinor-5-cis,13-trans-prostadienoic acid |
| 532 | 249 | 18-cyclopentyl-9β,11α,15-trihydroxy-16,16-trimethylene-19,20-dinor-13-trans-prostenoic acid |
| 533 | 252 | 18-cyclopentyl-2-ethyl-9β,11α,15-trihydroxy-16,16-trimethylene-19,20-dinor-13-trans-prostenoic acid |
| 534 | 255 | 18-cyclopentyl-9β,11α,15-trihydroxy-4-methyl-16,16-trimethylene-19,20-dinor-5-cis,13-trans-prostadienoic acid |
| 535 | 258 | 9β,11α,15-trihydroxy-16,16-trimethylene-13-cis-prostenoic acid |
| 536 | 259 | 9β,11α,15-trihydroxy-16,16-trimethylene-5-cis,13-cis-prostadienoic acid |
| 537 | 261 | 9β,11α,15-trihydroxy-2-methyl-16,16-trimethylene-13-cis-prostenoic acid |
| 538 | 262 | 9α,11α,15-trihydroxy-3,3-dimethyl-16,16-trimethylene-13-cis-prostenoic acid |
| 539 | 263 | 9β,11α,15-trihydroxy-4-methyl-16,16-trimethylene-5-cis,13-cis-prostadienoic acid |
| 540 | 264 | 9β,11α,15-trihydroxy-3-oxa-16,16-trimethylene-13-cis-prostenoic acid |
| 541 | 265 | 9β,11α,15-trihydroxy-2,3-trans-methano-16,16-trimethylene-13-cis-prostenoic acid |
| 542 | 268 | 1-methyl 9α,11α,15-trihydroxy-16,16-trimethylene-5-cis,13-trans-prostadienoate |
| 543 | 269 | 1-methyl 9α,11α,15-trihydroxy-16,16-trimethylene-19-nor-5-cis,13-trans-prostadienoate |
| 544 | 270 | 1-methyl 9α,11α,15-trihydroxy-20-methyl-16,16-trimethylene-5-cis,-13-trans-prostadienoate |
| 545 | 271 | 1-methyl 20-ethyl-9α,11α,15-trihydroxy-16,16-trimethylene-5-cis,-13-trans-prostadienoate |
| 546 | 272 | 1-methyl 9α,11α,15-trihydroxy-16,16-tetramethylene-5-cis,13-trans-prostadienoate |
| 547 | 273 | 1-methyl 9α,11α,15-trihydroxy-16,16-trimethylene-5-cis,13-trans-prostadien-18-ynoate |
| 548 | 274 | 1-methyl 9β,11α,15-trihydroxy-16,16-trimethylene-5-cis,13-trans,-18-cis-prostatrienoate |
| 549 | 275 | 1-methyl 9β,11α,15-trihydroxy-17-phenyl-16,16-trimethylene-5-cis,-13-trans-prostadienoate |
| 550 | 277 | 1-methyl 9β,11α,15-trihydroxy-16,16-trimethylene-5-cis,13-cis-prostadienoate |
| 551 | 278 | 1-methyl 9β,11α,15-trihydroxy-16,16-trimethylene-13-trans-prostenoate |
| 552 | 280 | 1-methyl 9β,11α,15-trihydroxy-20-methyl-16,16-trimethylene-13-trans-prostenoate |
| 553 | 281 | 1-methyl 20-ethyl-9β,11α,15-trihydroxy-16,16-trimethylene-13-trans-prostenoate |
| 554 | 282 | 1-methyl 9β,11α,15-trihydroxy-16,16-tetramethylene-13-trans-prostenoate |
| 555 | 283 | 1-methyl 9β,11α,15-trihydroxy-16,16-trimethylene-13-trans-prosten-18-ynoate |
| 556 | 284 | 1-methyl 9β,11α,15-trihydroxy-16,16-trimethylene-13-trans,18-cis-prostadienoate |
| 557 | 285 | 1-methyl 9β,11α,15-trihydroxy-17-phenyl-16,16-trimethylene-13-trans-prostenoate |
| 558 | 287 | 1-methyl 9β,11α,15-trihydroxy-16,16-trimethylene-13-cis-prostenoate |
| 559 | 288 | d-methyl 9β,11α,15-trihydroxy-16,16-trimethylene-13-trans-prostenoate |
| 560 | 290 | d-methyl 9β,11α,15-dihydroxy-20-methyl-16,16-trimethylene-13-trans-prostenoate |
| 561 | 291 | d-methyl 20-ethyl-9β,11α,15-trihydroxy-16,16-trimethylene-13-trans-prostenoate |
| 562 | 292 | d-methyl 9β,11α,15-trihydroxy-16,16-tetramethylene-13-trans-prostenoate |
| 563 | 293 | d-methyl 9β,11α,15-trihydroxy-16,16-trimethylene-13-trans-prosten-18-ynoate |
| 564 | 294 | d-methyl 9β,11α,15-trihydroxy-16,16-trimethylene-13-trans,18-cis-prostadienoate |
| 565 | 295 | d-methyl 9β,11α,15-trihydroxy-17-phenyl-16,16-trimethylene-13-trans-prostenoate |
| 566 | 297 | d-methyl 9β,11α,15-trihydroxy-16,16-trimethylene-13-cis-prostenoate |

EXAMPLE 567

15-Hydroxy-9-oxo-16,16-trimethylene-5-cis-10,13-trans-prostatrienoic acid

A solution of 1.5 g. of 11α,15-dihydroxy-9-oxo-16,16-trimethylene-5-cis,13-trans-prostadienoic acid (Example 201) in 80 ml. of 0.5 N hydrochloric acid in 1:1 tetrahydrofuran-water is allowed to stand at room temperature under argon for 72 hours. The solution is treated with brine and extracted with ether. The extract is washed with brine and dried with anhydrous magnesium sulfate. The residue remaining after evaporation of the solvent is purified by partition chromatography on Celite to give the product as an oil.

EXAMPLES 568–610

Treatment of the 11α,9-oxo-prostenoic acids listed in Table XIII below with dilute acid in accordance with the method described in Example 567 furnishes the products of the table.

TABLE XIII

| Example | Starting 9-oxo-11α-hydroxy-prostenoic acid of Example | Product 9-oxo-10,13-trans-prostadienoic acids |
|---|---|---|
| 568 | 202 | 15-hydroxy-9-oxo-16,16-trimethylene-10,13-trans-prostadienoic acid |
| 569 | 206 | 15-hydroxy-2-methyl-9-oxo-16,16-trimethylene-10,13-trans-prostadienoic acid |
| 570 | 207 | 2-ethyl-15-hydroxy-9-oxo-16,16-trimethylene-10,13-trans-prostadienoic acid |
| 571 | 208 | 15-hydroxy-3,3-dimethyl-9-oxo-16,16-tetramethylene-10,13-trans-prostadienoic acid |
| 572 | 209 | 15-hydroxy-9-oxo-16,16-trimethylene-7-nor-5-cis,10,13-trans-prostatrienoic acid |
| 573 | 211 | 15-hydroxy-4-methyl-9-oxo-16,16-trimethylene-5-cis,10,13-trans-prostatrienoic acid |
| 574 | 212 | 15-hydroxy-4(R)-methyl-16,16-trimethylene-9-oxo-5-cis,10,13-trans-prostatrienoic acid |
| 575 | 216a | 15-hydroxy-9-oxo-16,16-trimethylene-5-cis,10,13-trans-19-nor-prostatrienoic acid |
| 576 | 217 | 15-hydroxy-20-methyl-9-oxo-16,16-trimethylene-10,13-trans-prostadienoic acid |
| 577 | 218 | 15-hydroxy-2,20-dimethyl-9-oxo-16,16-trimethylene-10,13-trans-prostadienoic acid |
| 578 | 219 | 15-hydroxy-20-methyl-9-oxo-16,16-trimethylene-5-cis,10,13-trans-prostatrienoic acid |
| 579 | 222 | 20-ethyl-15-hydroxy-9-oxo-16,16-trimethylene-5-cis,10,13-trans-prostatrienoic acid |
| 580 | 222a | 20-ethyl-15-hydroxy-4-methyl-9-oxo-16,16-trimethylene-5-cis,10,13-trans-prostatrienoic acid |
| 581 | 223 | 15-hydroxy-9-oxo-16,16-tetramethylene-10,13-trans-prostadienoic acid |
| 582 | 224 | 15-hydroxy-9-oxo-16,16-tetramethylene-5-cis,10,13-trans-prostatrienoic acid |
| 583 | 226 | 2-ethyl-15-hydroxy-9-oxo-16,16-tetramethylene-10,13-trans-prostadienoic acid |
| 584 | 227 | 15-hydroxy-3,3-dimethyl-9-oxo-16,16-tetramethylene-10,13-trans-prostadienoic acid |
| 585 | 228 | 15-hydroxy-4-methyl-9-oxo-16,16-tetramethylene-5-cis,13-trans-prostadienoic acid |
| 586 | 229 | 15-hydroxy-3-oxa-9-oxo-16,16-tetramethylene-10,13-trans-prostadienoic acid |
| 587 | 230 | 15-hydroxy-2,3-trans-methano-9-oxo-16,16-tetramethylene-10,13-trans-prostadienoic acid |
| 588 | 231 | 15-hydroxy-9-oxo-16,16-trimethylene-10,13-trans-prostadien-18-ynoic acid |
| 589 | 232 | 15-hydroxy-9-oxo-16,16-trimethylene-5-cis,10,13-trans-prostatrien-18-ynoic acid |

TABLE XIII-continued

| Example | Starting 9-oxo-11α-hydroxy-prostenoic acid of Example | Product 9-oxo-10,13-trans-prostadienoic acids |
|---|---|---|
| 590 | 233 | 15-hydroxy-9-oxo-16,16-trimethylene-7a,7b-bishomo-10,13-trans-prostadien-18-ynoic acid |
| 591 | 234 | 15-hydroxy-2-methyl-9-oxo-16,16-trimethylene-10,13-trans-prosta-dien-18-ynoic acid |
| 592 | 236 | 15-hydroxy-4-methyl-9-oxo-16,16-trimethylene-5-cis,10,13-trans-prostatrien-18-ynoic acid |
| 593 | 237 | 15-hydroxy-3-oxa-9-oxo-16,16-trimethylene-10,13-trans-prostadien-18-ynoic acid |
| 594 | 238 | 15-hydroxy-2,3-methano-9-oxo-16,16-trimethylene-10,13-trans-prostadien-18-ynoic acid |
| 595 | 239 | 15-hydroxy-9-oxo-16,16-trimethylene-10,13-trans,18-cis-prosta-trienoic acid |
| 596 | 240 | 15-hydroxy-9-oxo-16,16-trimethylene-5-cis,10,13-trans,18-cis-prostatetraenoic acid |
| 597 | 245 | 15-hydroxy-9-oxo-17-phenyl-4-propyl-16,16-trimethylene-18,19,20-trinor-5-cis,10,13-trans-prostatrienoic acid |
| 598 | 248 | 15-hydroxy-3,3-dimethyl-9-oxo-17-phenyl-16,16-trimethylene-18,19,20-trinor-10,13-trans-prostadienoic acid |
| 599 | 252 | 18-cyclopentyl-2-ethyl-15-hydroxy-9-oxo-16,16-trimethylene-19,20-dinor-10,13-trans-prostadienoic acid |
| 600 | 253 | 18-cyclopentyl-15-hydroxy-3,3-dimethyl-9-oxo-16,16-trimethylene-19,20-dinor-10,13-trans-prostadienoic acid |
| 601 | 255 | 18-cyclopentyl-15-hydroxy-4-methyl-9-oxo-16,16-trimethylene-19,20-dinor-5-cis,10,13-trans-prostatrienoic acid |
| 602 | 256 | 18-cyclopentyl-15-hydroxy-3-oxa-9-oxo-16,16-trimethylene-19,20-dinor-10,13-trans-prostadienoic acid |
| 603 | 257 | 18-cyclopentyl-15-hydroxy-2,3-trans-methano-9-oxo-16,16-trimethylene-19,20-dinor-10,13-trans-prostadienoic acid |
| 604 | 258 | 15-hydroxy-9-oxo-16,16-trimethylene-10,13-cis-prostadienoic acid |
| 605 | 259 | 15-hydroxy-9-oxo-16,16-trimethylene-5-cis,10,13-cis-prostatrienoic acid |
| 606 | 261 | 15-hydroxy-2-methyl-9-oxo-16,16-trimethylene-10,13-cis-prostadienoic acid |
| 607 | 262 | 15-hydroxy-3,3-dimethyl-9-oxo-16,16-trimethylene-10,13-cis-prostadienoic acid |
| 608 | 263 | 15-hydroxy-4-methyl-9-oxo-16,16-trimethylene-5-cis,10,13-cis-prostatrienoic acid |
| 609 | 264 | 15-hydroxy-3-oxa-9-oxo-16,16-trimethylene-10,13-cis-prostadienoic acid |
| 610 | 265 | 15-hydroxy-2,3-trans-methano-9-oxo-16,16-trimethylene-10,13-cis-prostadienoic acid |

EXAMPLE 611

15-Hydroxy-9-oxo-16,16-trimethylene-5-cis,8(12),13-trans-prostatrienoic acid

A mixture of 110 mg of 11α,15-dihydroxy-9-oxo-16,16-trimethylene-5-cis,13-trans-prostadienoic acid (Example 201) in 40 ml. of 95% ethanol and 40 ml. of 1N sodium hydroxide is stirred under argon at ambient temperature for 1 hour. The solution is concentrated to remove ethanol, acidified with 1 N hydrochloric acid and extracted with ethyl acetate. The extracts are washed with saturated sodium chloride solution, dried with anhydrous magnesium sulfate and taken to dryness. The residual oil is chromatographed on silica gel to give 100 mg. of product as an oil.

EXAMPLES 612–637

Treatment of the 11α-9-oxo-prostenoic acids listed in Table XIV below with ethanol-1N sodium hydroxide in accordance with the method described in Example 611 furnishes the products of the table.

TABLE XIV

| Example | Starting 9-oxo-11α-hydroxy-prostenoic acid of Example | Product 9-oxo-15-hydroxy-16,16-alkylene-8(12),13-trans-prostadienoic acids |
|---|---|---|
| 612 | 202 | 15-hydroxy-9-oxo-16,16-trimethylene-8(12),13-trans-prostadienoic acid |
| 613 | 206 | 15-hydroxy-2-methyl-9-oxo-16,16-trimethylene-8(12),13-trans-prostadienoic acid |
| 614 | 208 | 15-hydroxy-3,3-dimethyl-9-oxo-16,16-trimethylene-8(12),13-trans-prostadienoic acid |
| 615 | 211 | 15-hydroxy-4-methyl-9-oxo-16,16-trimethylene-5-cis,8(12),13-trans-prostatrienoic acid |
| 616 | 217 | 15,hydroxy-20-methyl-9-oxo-16,16-trimethylene-8(12),13-trans-prostadienoic acid |
| 617 | 219 | 15-hydroxy-20-methyl-9-oxo-16,16-trimethylene-5-cis,8(12),13-trans-prostatrienoic acid |
| 618 | 222 | 20-ethyl-15-hydroxy-9-oxo-16,16-trimethylene-5-cis-8(12),13-trans-prostatrienoic acid |
| 619 | 222a | 20-ethyl-15-hydroxy-4-methyl-9-oxo-16,16-trimethylene-5-cis-8(12),-13-trans-prostatrienoic acid |
| 620 | 223 | 15-hydroxy-9-oxo-16,16-tetramethylene-8(12),13-trans-prostadienoic acid |
| 621 | 224 | 15-hydroxy-9-oxo-16,16-tetramethylene-5-cis,8(12),13-trans-prostatrienoic acid |
| 622 | 226 | 2-ethyl-15-hydroxy-9-oxo-16,16-tetramethylene-8(12),13-trans-prostadienoic acid |
| 623 | 229 | 15-hydroxy-3-oxa-9-oxo-16,16-tetramethylene-8(12),13-trans-prostadienoic acid |
| 624 | 230 | 15-hydroxy-2,3-trans-methano-9-oxo-16,16-tetramethylene-8(12),13-trans-prostadienoic acid |
| 625 | 231 | 15-hydroxy-9-oxo-16,16-trimethylene-8(12),13-trans-prostadien-18-ynoic acid |
| 626 | 232 | 15-hydroxy-9-oxo-16,16-trimethylene-5-cis,8(12),13-trans-prostatrien-18-ynoic acid |
| 627 | 234 | 15-hydroxy-2-methyl-9-oxo-16,16-trimethylene-8(12),13-trans-prostadien-18-ynoic acid |
| 628 | 237 | 15-hydroxy-3-oxa-9-oxo-16,16-trimethylene-8(12),13-trans-prostadien-18-ynoic acid |
| 629 | 238 | 15-hydroxy-2,3-methano-9-oxo-16,16-trimethylene-8(12),13-trans-prostadien-18-ynoic acid |
| 630 | 248 | 15-hydroxy-3,3-dimethyl-9-oxo-17-phenyl-16,16-trimethylene-18,19,-20-trinor-8(12),13-trans-prostadienoic acid |
| 631 | 253 | 18-cyclopentyl-15-hydroxy-3,3-dimethyl-9-oxo-16,16-trimethylene-19,20-dinor-8(12),13-trans-prostadienoic acid |
| 632 | 256 | 18-cyclopentyl-15-hydroxy-3-oxa-9-oxo-16,16-trimethylene-19,20-dinor-8(12),13-trans-prostadienoic acid |
| 633 | 258 | 15-hydroxy-9-oxo-16,16-trimethylene-8(12),13-cis-prostadienoic acid |
| 634 | 261 | 15-hydroxy-2-methyl-9-oxo-16,16-trimethylene-8(12),13-cis-prostadienoic acid |
| 635 | 263 | 15-hydroxy-4-methyl-9-oxo-16,16-trimethylene-5-cis,8(12),13-cis-prostadienoic acid |
| 636 | 264 | 15-hydroxy-3-oxa-9-oxo-16,16-trimethylene-8(12),13-cis-prostadienoic acid |
| 637 | 265 | 15-hydroxy-2,3-trans-methano-9-oxo-16,16-trimethylene-8(12),13-cis-prostadienoic acid |

EXAMPLE 638

11α,15-Dihydroxy-9-oxo-16,16-trimethylene-prostanoic acid

A solution of 800 mg. of 11α,15-dihydroxy-9-oxo-16,16-trimethylene-5-cis,13-trans-prostadienoic acid (Example 201) in 50 ml. of ethyl acetate is hydrogenated in a Parr apparatus using 500 mg. of 5% rhodium on carbon. The catalyst is removed by filtration and the mother liquor is taken to dryness to furnish 795 mg. of product.

EXAMPLES 639–683

Hydrogenation of the prostenoic acids listed in Table XV below in ethyl acetate using 5% rhodium on carbon catalyst in accordance with the method described in Example 638 furnishes the prostanoic acids of the table.

TABLE XV

| Example | Starting prostenoic acids of Example | Product prostanoic acids |
|---|---|---|
| 639 | 8 | 9-oxo-15-hydroxy-16,16-trimethylene-prostanoic acid |
| 640 | 126 | 15-hydroxy-2-methyl-9-oxo-16,16-trimethylene-prostanoic acid |
| 641 | 128 | 15-hydroxy-2,3-trans-methano-9-oxo-16,16-trimethylene-prostanoic acid |
| 642 | 129 | 15-hydroxy-3,3-dimethyl-9-oxo-16,16-trimethylene-prostanoic acid |
| 643 | 130 | 15-hydroxy-3-oxa-9-oxo-16,16-trimethylene-prostanoic acid |
| 644 | 132 | 15-hydroxy-9-oxo-2-phenyl-16,16-trimethylene-prostanoic acid |
| 645 | 137 | 15-hydroxy-4-methyl-9-oxo-16,16-trimethylene-prostanoic acid |
| 646 | 140 | 15-hydroxy-4(R)-methyl-9-oxo-16,16-trimethylene-prostanoic acid |

TABLE XV-continued

| Example | Starting prostenoic acids of Example | Product prostanoic acids |
|---|---|---|
| 647 | 143 | 15-hydroxy-2,3-trans-methano-20-methyl-9-oxo-16,16-trimethylene-prostanoic acid |
| 648 | 143a | 15-hydroxy-20-methyl-9-oxo-16,16-trimethylene-prostanoic acid |
| 649 | 144 | 15-hydroxy-3,3,20-trimethyl-9-oxo-16,16-trimethylene-prostanoic acid |
| 650 | 145 | 15-hydroxy-20-methyl-3-oxa-9-oxo-16,16-trimethylene prostanoic acid |
| 651 | 146 | 20-ethyl-15-hydroxy-9-oxo-2-phenyl-16,16-trimethylene-prostanoic acid |
| 652 | 146a | 20-ethyl-15-hydroxy-9-oxo-16,16-trimethylene-prostanoic acid |
| 653 | 149 | 15-hydroxy-9-oxo-16,16-tetramethylene-prostanoic acid |
| 654 | 151 | 15-hydroxy-2-methyl-9-oxo-16,16-tetramethylene-prostanoic acid |
| 655 | 152 | 15-hydroxy-2,3-trans-methano-9-oxo-16,16-tetramethylene-prostanoic acid |
| 656 | 153 | 15-hydroxy-3,3-dimethyl-9-oxo-16,16-tetramethylene-prostanoic acid |
| 657 | 154 | 15-hydroxy-9-oxo-2-phenyl-16,16-tetramethylene-prostanoic acid |
| 658 | 155 | 15-hydroxy-3-oxa-9-oxo-16,16-tetramethylene-prostanoic acid |
| 659 | 184 | 18-cyclopentyl-15-hydroxy-9-oxo-16,16-trimethylene-19,20-dinor-prostanoic acid |
| 660 | 185 | 18-cyclopentyl-15-hydroxy-3,3-dimethyl-9-oxo-16,16-trimethylene-19,20-dinor-prostanoic acid |
| 661 | 186 | 18-cyclopentyl-15-hydroxy-9-oxo-2-phenyl-16,16-trimethylene-19,20-dinor-prostanoic acid |
| 662 | 189 | 18-cyclopentyl-15-hydroxy-3-oxa-9-oxo-16,16-trimethylene-19,20-dinor-prostanoic acid |
| 663 | 196 | 15-hydroxy-9-oxo-2-phenyl-16,16-trimethylene-prostanoic acid |
| 664 | 202 | 11α,15-dihydroxy-9-oxo-16,16-trimethylene-prostanoic acid |
| 665 | 206 | 11α,15-dihydroxy-2-methyl-9-oxo-16,16-trimethylene-prostanoic acid |
| 666 | 208 | 11α,15-dihydroxy-3,3-dimethyl-9-oxo-16,16-trimethylene-prostanoic acid |
| 667 | 211 | 11α,15-dihydroxy-4-methyl-9-oxo-16,16-trimethylene-prostanoic acid |
| 668 | 215 | 11α,15-dihydroxy-9-oxo-16,16-trimethylene-19-nor-prostanoic acid |
| 669 | 217 | 11α,15-dihydroxy-20-methyl-9-oxo-16,16-trimethylene-prostanoic acid |
| 670 | 218 | 11α,15-dihydroxy-2,20-dimethyl-9-oxo-16,16-trimethylene-prostanoic acid |
| 671 | 221 | 20-ethyl-11α,15-dihydroxy-9-oxo-16,16-trimethylene-prostanoic acid |
| 672 | 223 | 11α,15-dihydroxy-9-oxo-16,16-tetramethylene-prostanoic acid |
| 673 | 226 | 2-ethyl-11α,15-dihydroxy-9-oxo-16,16-tetramethylene-prostanoic acid |
| 674 | 227 | 11α,15-dihydroxy-3,3-dimethyl-9-oxo-16,16-tetramethylene-prostanoic acid |
| 675 | 229 | 11α,15-dihydroxy-3-oxa-9-oxo-16,16-tetramethylene-prostanoic acid |
| 676 | 230 | 11α,15-dihydroxy-2,3-trans-methano-9-oxo-16,16-tetramethylene-prostanoic acid |
| 677 | 241 | 11α,15-dihydroxy-9-oxo-17-phenyl-16,16-trimethylene-18,19,20-trinor-prostanoic acid |
| 678 | 246 | 11α,15-dihydroxy-3-oxa-9-oxo-17-phenyl-16,16-trimethylene-18,19,20-trinor-prostanoic acid |
| 679 | 247 | 11α,15-dihydroxy-2,3-trans-methano-9-oxo-17-phenyl-16,16-trimethylene-18,19,20-trinor-prostanoic acid |
| 680 | 249 | 18-cyclopentyl-11α,15-dihydroxy-9-oxo-17-phenyl-16,16-trimethylene-19,20-dinor-prostanoic acid |
| 681 | 252 | 18-cyclopentyl-2-ethyl-11α,15-dihydroxy-9-oxo-17-phenyl-16,16-trimethylene-19,20-dinor-prostanoic acid |
| 682 | 256 | 18-cyclopentyl-11α,15-dihydroxy-3-oxa-9-oxo-17-phenyl-16,16-trimethylene-19,20-dinor-prostanoic acid |
| 683 | 257 | 18-cyclopentyl-11α,15-dihydroxy-2,3-trans-methano-9-oxo-17-phenyl-16,16-trimethylene-19,20-dinor-prostanoic acid |

EXAMPLE 684

Ethyl 9-ethylenedioxy-15-hydroxy-16,16-trimethylene-13-trans-prostenoate

A solution of 2 g. of ethyl 15-hydroxy-9-oxo-16,16-trimethylene-13-trans-prostenoate (Example 7) in 80 ml. of benzene containing 2 ml. of ethylene glycol and 40 mg. of p-toluenesulfonic acid is stirred at the reflux temperature under a Dean-Stark water separator for 18 hours. The cooled solution is washed with 5% sodium carbonate solution, saturated sodium chloride solution, dried with anhydrous sodium sulfate and taken to dryness to furnish 2.3 g. of an oil. Chromatography on florisil and eluting with benzene and 5% ether in benzene furnishes 1.93 g. of pure product as an oil.

EXAMPLE 685

9-ethylenedioxy-15-hydroxy-16,16-trimethylene-13-trans-prostenoic acid

A suspension of 1.45 g. of ethyl-9 ethylenedioxy-15-hydroxy-16,16-trimethylene-13-trans-prostenoate (Example 684) in 30 ml. of methanol-water (1:1) containing 650 mg. of potassium hydroxide is stirred at 50° for 2 hours in an atmosphere of argon. The resulting solution is stirred at ambient temperature for 18 hours. After cooling and filtration thru Celite the solution is acidified with 30% aqueous sodium phosphate monobasic and extracted several times with ether. The combined extracts are washed with saturated sodium chloride solution, dried with anhydrous sodium sulfate and taken to dryness to provide 1.15 g. of product as an oil.

EXAMPLE 686

Ethyl 9-ethylenedioxy-15-hydroxy-3-thia-16,16-trimethylene-13-trans-prostenoate

In the manner described in Example 684, treatment of ethyl 15-hydroxy-9-oxo-3-thia-16,16-trimethylene-13-trans-prostenoate (Example 55) with ethylene glycol in benzene containing p-toluenesulfonic acid is productive of the subject product.

EXAMPLE 687

9-Ethylenedioxy-15-hydroxy-3-thia-16,16-trimethylene-13-trans-prostenoic acid

In the manner described in Example 685, treatment of ethyl 9-ethylenedioxy-15-hydroxy-3-thia-16,16-trimethylene-13-trans-prostenoate (Example 686) with potassium hydroxide in methanol-water furnishes the subject product.

EXAMPLES 688–710

Hydrogenation of the 9-oxo-13-trans-prostenoate esters listed in Table XVI below by the method described in Example 638 furnishes the corresponding 9-oxo-prostanoate esters. These in turn when treated with the appropriate diols, also listed in the table below in the manner described in Example 684 furnishes the corresponding ketals. Finally, saponification of the prostanoate ketal esters in the manner described in Example 685 is productive of the prostanoic acid ketals of the table.

TABLE XVI

| Example | Starting prostenoic acid ester of Example | Diols | Product prostanoic acid ketals |
|---|---|---|---|
| 688 | 7 | ethylene glycol | 9,9-ethylenedioxy-15-hydroxy-16,16-trimethylene-prostanoic acid |
| 689 | 7 | 2,3-butanediol | 9,9-(1,2-dimethylethylenedioxy)-15-hydroxy-16,16-trimethylene-prostanoic acid |
| 690 | 7 | 3-chloro-1,2-propanediol | 9,9-(1-chloromethylethylenedioxy)-15-hydroxy-16,16-trimethylene-prostanoic acid |
| 691 | 7 | 1,3-propanediol | 9,9-propylenedioxy-15-hydroxy-16,16-trimethylene-prostanoic acid |
| 692 | 7 | 2,2-dimethyl-1,3-propanediol | 9,9-(2,2-dimethylpropylenedioxy)-15-hydroxy-16,16-trimethylene-prostanoic acid |
| 693 | 47 | ethylene glycol | 9,9-ethylenedioxy-15-hydroxy-16,16-trimethylene-7-nor-prostanoic acid |
| 694 | 50 | 3-chloro-1,2-propanediol | 9,9-(1-chloromethylethylenedioxy)-15-hydroxy-2-methyl-16,16-trimethylene-prostanoic acid |
| 695 | 52 | 2,3-butanediol | 9,9-(1,2-dimethylethylenedioxy)-15-hydroxy-2,3-trans-methano-16,16-trimethylene-prostanoic acid |
| 696 | 53 | 2,2-dimethyl-1,3-propanediol | 9,9-(2,2-dimethylpropylenedioxy)-15-hydroxy-3,3-dimethyl-16,16-trimethylene-prostanoic acid |
| 697 | 54 | 1,3-propanediol | 9,9-propylenedioxy-15-hydroxy-3-oxa-16,16-trimethylene-prostanoic acid |
| 698 | 56 | ethyleneglycol | 9,9-ethylenedioxy-15-hydroxy-2-phenyl-16,16-trimethylene-prostanoic acid |
| 699 | 64a | ethyleneglycol | 9,9-ethylenedioxy-15-hydroxy-16,16-trimethylene-19-nor-prostanoic acid |
| 700 | 66 | ethyleneglycol | 9,9-ethylenedioxy-15-hydroxy-2-methyl-16,16-trimethylene-19-nor-prostanoic acid |
| 701 | 67 | 2,2-dimethyl-1,3-propanediol | 9,9-(2,2-dimethylpropylenedioxy)-15-hydroxy-2,3-trans-methano-20-methyl-16,16-trimethylene-prostanoic acid |
| 702 | 70 | 2,2-dimethyl-1,3-propanediol | 9,9-(2,2-dimethylpropylenedioxy)-20-ethyl-15-hydroxy-2-phenyl-16,16-trimethylene-prostanoic acid |
| 703 | 73 | 2,2-dimethyl-1,3-propanediol | 9,9-(2,2-dimethylpropylenedioxy)-15-hydroxy-16,16-tetramethylene-prostanoic acid |
| 704 | 74 | 1,3-propanediol | 9,9-propylenedioxy-15-hydroxy-16,16-tetramethylene-7a,7b-bishomo-prostanoic acid |
| 705 | 76 | 1,3-propanediol | 9,9-propylenedioxy-15-hydroxy-2,3-trans-methano-16,16-tetramethylene-prostanoic acid |
| 706 | 102 | 3-chloro-1,2-propanediol | 9,9-(1-chloromethylethylenedioxy)-2-ethyl-15-hydroxy-17-phenyl-16,16-trimethylene-18,19,20-trinor-prostanoic acid |
| 707 | 103 | 3-chloro-1,2-propanediol | 9,9-(1-chloromethylethylenedioxy)-15-hydroxy-2,17-diphenyl-16,16-trimethylene-18,19,20-trinor-prostanoic acid |
| 708 | 108 | 2,3-butanediol | 9,9-(1,2-dimethylethylenedioxy)-18-cyclopentyl-15-hydroxy-16,16-trimethylene-19,20-dinor-prostanoic acid |
| 709 | 113 | 2,3-butanediol | 9,9-(1,2-dimethylethylenedioxy)-18-cyclopentyl-15-hydroxy-3-oxa-16,16-trimethylene-19,20-dinor-prostanoic acid |
| 710 | 115 | 2,3-butanediol | 9,9-(1,2-dimethylethylenedioxy)-18-cyclopentyl-15-hydroxy-2,3-trans-methano-16,16-trimethylene-19,20-dinor-prostanoic acid |

EXAMPLE 711

9-(p-Carboxyphenylhydrazano)-11α,15-dihydroxy-16,16-trimethylene-5cis,13-trans-prostadienoic acid A mixture of 250 mg. of 11α,15-dihydroxy-16,16-trimethylene-5-cis,13-trans-prostadienoic acid (Example 201) and 250 mg. of p-carboxyphenylhydrazine in 15 ml. of absolute ethanol containing 1 drop of glacial acetic acid is stirred at 40°, under argon atmosphere, for 30 minutes. The resulting solution is kept at ambient temperature for 72 hours, then flooded with water and extracted several times with ether. The combined extracts are washed with ice cold dilute hydrochloric acid, saturated sodium chloride solution, dried with anhydrous magnesium sulfate and taken to dryness to furnish the subject product.

EXAMPLES 712–740

Treatment of the 9-oxo-prostenoic acids listed in Table XVII below with the phenylhydrazines, also listed in the Table, in accordance with the procedure described in Example 711 is productive of the prostenoic acid phenylhydrazones of the Table.

TABLE XVII

| Example | Starting 9-oxo-prostenoic acids of Example | Phenylhydrazines | Product prostenoic acid phenylhydrazones |
|---|---|---|---|
| 712 | 8 | p-carboxy-phenylhydrazine | 9-(p-carboxyphenylhydrazano)-15-hydroxy-16,16-trimethylene-13-trans-prostenoic acid |
| 713 | 126 | 2,5-dichloro-phenylhydrazine | 9-(2,5-dichlorophenylhydrazano)-15-hydroxy-2-methyl-16,16-trimethylene-13-trans-prostenoic acid |
| 714 | 128 | p-tolylhydrazine | 9-(p-tolylhydrazano)-15-hydroxy-2,3-trans-methano-16,16-trimethylene-13-trans-prostenoic acid |
| 715 | 130 | p-chlorophenylhydrazine | 9-(p-chlorophenylhydrazano)-15-hydroxy-9-oxo-16,16-trimethylene-13-trans-prostenoic acid |
| 716 | 131 | p-carboxyphenylhydrazine | 9-(p-carboxyphenylhydrazano)-15-hydroxy-3-thia-16,16-trimethylene-13-trans-prostenoic acid |
| 717 | 132 | p-chlorophenylhydrazine | 9-(p-chlorophenylhydrazano)-15-hydroxy-2-phenyl-16,16-trimethylene-13-trans-prostenoic acid |
| 718 | 134 | p-tolylhydrazine | 9-(p-tolyhydrazano)-15-hydroxy-16,16-trimethylene-5-cis,13-trans-prostadienoic acid |
| 719 | 138 | 2,5-dichlorophenylhydrazine | 9-(2,5-dichlorophenylhydrazano)-4-ethyl-15-hydroxy-16,16-trimethylene-5-cis,13-trans-prostadienoic acid |
| 720 | 143a | p-carboxyphenylhydrazine | 9-(p-carboxyphenylhydrazano)-15-hydroxy-20-methyl-16,16-trimethylene-13-trans-prostenoic acid |
| 721 | 145 | p-carboxyphenylhydrazine | 9-(p-carboxyphenylhydrazano)-15-hydroxy-20-methyl-3-oxa-16,16-trimethylene-13-trans-prostenoic acid |
| 722 | 149 | p-carboxyphenylhydrazine | 9-(p-carboxyphenylhydrazano)-15-hydroxy-16,16-trimethylene-13-trans-prostenoic acid |
| 723 | 151 | p-tolylhydrazine | 9-(p-tolylhydrazano)-15-hydroxy-2-methyl-16,16-tetramethylene-13-trans-prostenoic acid |
| 724 | 177 | p-tolylhydrazine | 9-(p-tolylhydrazano)-15-hydroxy-17-phenyl-16,16-trimethylene-13-trans-prostenoic acid |
| 725 | 186 | 2,5-dichlorophenylhydrazine | 9-(2,5-dichlorophenylhydrazano)-15-hydroxy-17-phenyl-3-thia-16,16-trimethylene-18,19-20-trinor-13-trans-prostenoic acid |
| 726 | 192 | 2,5-dichlorophenylhydrazine | 9-(2,5-dichlorophenylhydrazano)-15-hydroxy-9-oxo-16,16-trimethylene-13-cis-prostenoic acid |
| 727 | 202 | p-carboxyphenylhydrazine | 9-(p-carboxyphenylhydrazano)-11α,15-dihydroxy-16,16-trimethylene-13-trans-prostenoic acid |
| 728 | 206 | p-carboxyphenylhydrazine | 9-(p-carboxyphenylhydrazano)-11α,15-dihydroxy-2-methyl-16,16-trimethylene-13-trans-prostenoic acid |
| 729 | 208 | p-carboxyphenylhydrazine | 9-(p-carboxyphenylhydrazano)-11α,15-dihydroxy-3,3-dimethyl-16,16-tetramethylene-13-trans-prostenoic acid |
| 730 | 211 | p-carboxyphenylhydrazine | 9-(p-carboxyphenylhydrazano)-11α,15-dihydroxy-4-methyl-16,16-trimethylene-5-cis,13-trans-prostadienoic acid |
| 731 | 217 | p-carboxyphenylhydrazine | 9-(p-carboxyphenylhydrazano)-11α,15-dihydroxy-20-methyl-16,16-trimethylene-5-cis,13-trans-prostadienoic acid |
| 732 | 219 | p-chlorophenylhydrazine | 9-(p-chlorophenylhydrazano)-11α,15-dihydroxy-20-methyl-16,16-trimethylene-5-cis,13-trans-prostadienoic acid |
| 733 | 223 | p-chlorophenylhydrazine | 9-(p-chlorophenylhydrazano)-11α,15-dihydroxy-16,16-tetramethylene-13-trans-prostenoic acid |
| 734 | 227 | p-chlorophenylhydrazine | 9-(p-chlorophenylhydrazano)-11α,15-dihydroxy-2,3-dimethyl-16,16-tetramethylene-13-trans- |

TABLE XVII-continued

| Example | Starting 9-oxo-prostenoic acids of Example | Phenylhydrazines | Product prostenoic acid phenylhydrazones |
|---|---|---|---|
| 735 | 229 | p-chlorophenylhydrazine | prostenoic acid 9-(p-chlorophenylhydrazano)-11α,15-dihydroxy-3-oxa-16,16-tetramethylene-13-trans-prostanoic acid |
| 736 | 230 | p-chlorophenylhydrazine | 9-(p-chlorophenylhydrazano)-11α,15-dihydroxy-2,3-trans-methano-16,16-tetramethylene-13-trans-prostenoic acid |
| 737 | 231 | p-tolylhydrazine | 9-(p-tolyhydrazano)-11α,15-dihydroxy-16,16-trimethylene-13-trans-prosten-18-ynoic acid |
| 738 | 241 | p-tolylhydrazine | 9-(p-tolylhydrazano)-11α,15-dihydroxy-17-phenyl-16,16-trimethylene-18,19,20-trinor-13-trans-prostenoic acid |
| 739 | 249 | 2,5-dichlorophenylhydrazine | 9-(2,5-dichlorophenylhydrazano)-11α,15-dihydroxy-16,16-trimethylene-19,20-dinor-5-cis,-13-trans-prostadienoic acid |
| 740 | 258 | 2,5-dichlorophenylhydrazine | 9-(2,5-dichlorophenylhydrazano)-11α,15-dihydroxy-16,16-trimethylene-13-cis-prostenoic acid |

EXAMPLE 741

2-(1-Butyl-4-carboxaldehyde)-3-methoximino-1-cyclopentene

To a solution of 96 ml. of dry pyridine in 1800 ml. of dry methylene chloride in added 60 g. of chromic acid and the resulting mixture is stirred at room temperature for 1 hour. A solution of 19.7 g. of 2-(5-hydroxy-1-pentyl)-3-methoximino-1-cyclopentene (U.S. Pat. No. 3,836,581) in 100 ml. of dry methylene chloride is then added and the mixture is stirred for 1 hour at room temperature. The solution is decanted from the tarry residue, which is washed with 200 ml. of methylene chloride. The combined organic solutions are washed successively with dilute hydrochloric acid, water, dilute sodium bicarbonate solution, and saturated brine, dried with anhydrous MgSO4, and evaporated in vacuo to yield the title compound as an oil.

EXAMPLE 742

2-(1-Butyl-4-carboxaldehyde)-3-methoximino-1-cyclopentene

A mixture of 3.6 g. of pyridine dichromate (W. M. Coates and J. R. Corrigan, Chem. and Industry, 1969, 1594) and 0.730 g. of 2-(5-hydroxy-1-pentyl)-3-methoximino-1-cyclopentene (U.S. Pat. No. 3,836,581) in 125 ml. of dry methylene chloride is stirred at room temperature for 20 hours, filtered through Celite ®, and is evaporated to an oil. The latter was dissolved in ether, filtered, and the filtrate is washed with cold 5% sodium hydroxide solution, cold 5% hydrochloric acid, and saturated brine, dried (MgSO4), and evaporated to yield an oil. The latter is dissolved in methylene chloride, filtered through Florisil ®, and the filtrate is evaporated in vacuo to yield the subject compound as an oil.

EXAMPLE 743

2-(6-Carbethoxy-6-E-hexenyl)-3-methoximino-1-cyclopentene and
2-(6-Carbethoxy-6-Z-hexenyl)-3-methoximino-1-cyclopentene A mixture of 16.4 g. of 2-(1-butyl-4-carboxaldehyde)-3-methoximino-1-cyclopentene (Example 741) and 47 g. of carbethoxymethylene triphenylphosphorane in 150 ml. of benzene is stirred at room temperature for 2 hours and evaporated in vacuo. The residue is triturated with hexane, filtered, and the filtrate is evaporated in vacuo. The residue is column-chromatographed upon 150 g. of Florisil ® packed in hexane. The column is eluted first with hexane, then with solutions of hexane containing increasing amounts of methylene chloride, and finally with methylene chloride. The early fractions from the column contain small quantities, <10% yield, of the less polar 2-(6-carbethoxy-6-Z-hexenyl)-3-methoximino-1-cyclopentene. The later fractions from the column contain the bulk of product, i.e., the more polar, 2-(6-carbethoxy-6-E-hexenyl)-3-methoximino-1-cyclopentane.

EXAMPLE 744

2-(6-Carbethoxy-5,6-methanohexyl)-3-methoximino-1-cyclopentene

Sodium hydride, 1.68 g. of a 57% dispersion in mineral oil, is washed 4 minutes with hexane and dried in vacuo. To the free sodium hydride under nitrogen is added 8.8 g. of finely powdered trimethylsulfoxonium iodide and 100 ml. of anhydrous dimethylsulfoxide and the resulting mixture is stirred at room temperature for 0.75 hour. To the so formed ylide is added 10.0 g. of 2-(6-carbethoxy-6-Z-hexenyl)-3-methoximino-1-cyclopentane (Example 3) and the resulting mixture is stirred at room temperature for 2 hours and then poured into 750 ml. of water. The mixture is extracted 5 times with 200 ml. of hexane and the combined abstracts are washed with water and saturated brine, dried (MgSO4), and evaporated in vacuo to yield the title compound as an oil.

EXAMPLE 745

2-(6-Carbethoxy-5,6-methanohexyl)-cyclopent-2-en-1-one and
2-(6-Carboxy-5,6-methanohexyl)-cyclopent-2-n-1-one A mixture of 5.2 g. of dl-2-(6-carbethoxy-5,6-methanohexyl)-3-methoximino-1-cyclopentene. (Example 4) and 38 ml. of 2 N hydrochloric acid in 95 ml. of acetone is refluxed for 2 hours, cooled, and partially evaporated in vacuo. The residue is partitioned between water and hexane. The organic phase is washed with water, dilute sodium bicarbonate solution, water, and brine, dried (MgSO4), and evaporated in vacuo to yield crude 2-(6-carbethoxy-5,6-methanohexyl)-cyclopent-2-en-1-one which is purified by column-chromatography upon Florisil ® and with a hexane-methylene chloride gradient as eluting solvent. The sodium bicarbonate washings are acidified with hydrochloric acid and extracted with methylene chloride. The organic phase is washed with water and saturated brine, dried (MgSO$_4$), and evaporated in vacuo to yield 2-(6-carboxy-5,6-methanohexyl)-cyclopent-2-en-1-one.

EXAMPLE 746

Preparation of 2-(7-carbethoxy-6-thiaheptyl)-1-methoximino-2-cyclopentene

To a stirred mixture of 24.2 g. (0.577 mols) of sodium hydride (57.2% in mineral oil) in 350 ml. of dimethoxyethane, under nitrogen, is added slowly 69 g. (0.575 mols) of ethyl 2-mercaptoacetate. The reaction mixture is stirred at room temperature for one hour and then a solution of 100 g. (0.363 mols) of 2-(5-methanesulfonyloxypentyl)-1-methoximino-2-cyclopentene (U.S. Pat. No. 3,836,581) in 300 ml. of dimethoxyethane is added dropwise and stirred at room temperature for 18 hours.

EXAMPLE 747

Preparation of 2-(7-carboxy-6-thiaheptyl)-2-cyclopentenone

A solution of 100 g. (0.333 mols) of 2(7-carbethoxy-6-thiaheptyl)-1-methoximino-2-cyclopentane in 1800 ml. of acetone and 700 ml. of 2 N hydrochloric acid is refluxed for 5 hours. The mixture is cooled, the solvent is evaporated and the residue partitioned between water and diethyl ether. The organic phase is washed with water and saline, dried (MgSO$_4$) and evaporated to give 94 g. of subject product as a yellow oil. The solution is heated at reflux for one hour, cooled and poured into cold dilute hydrochloric acid and then extracted with ether. The combined ether extracts are washed with saline, dried over magnesium sulfate and evaporated to give 105 g. of subject product as a yellow oil.

EXAMPLE 748

Preparation of 2-(7-carbethoxy-6-thiaheptyl)-2-cyclopentenone

A mixture of 74 g. (0.306 mols) of 2-(7-carboxy-6-thiaheptyl)-2-cyclopentenone, 1200 ml. of ethanol and 1 g. p-toluenesulfonic acid is stirred and refluxed for 18 hours. The resulting solution is concentrated and the residue is dissolved in ether. The organic phase is washed with water, sodium bicarbonate solution and saline, dried (MgSO$_4$) and evaporated. The residue is distilled to give a light yellow oil, o.p. 147°–150° C. (0.07 Torr).

EXAMPLE 749

Preparation of 2,2-trimethylene-4-cis-hexen-1-ol

Reduction of ethyl 2,2-trimethylene-4-cis-hexenoate (Example 46) with diisobutylaluminum hydride in the manner described in Example 2 above is productive of the subject product.

EXAMPLE 750

Preparation of 2,2-trimethylene-4-cis-hexen-1-ol

Oxidation of 2,2-trimethylene-4-cis-hexen-1-ol (Example 749) with chromium trioxide-pyridine complex by the procedure described in Example 3 above furnishes the subject product.

EXAMPLE 751

Preparation of 4,4-trimethylene-6-cis-octen-1-yn-3-ol

Treatment of 2,2-trimethylene-4-cis-hexen-1-ol (Example 750) with lithium acetylide-ethylene-diamine complex in the manner described in Example 4 above furnishes the subject product.

EXAMPLE 752

Preparation of 4,4-trimethylene-3-trimethylsilyloxy-6-cis-octen-1-yne

Treatment of 4,4-trimethylene-6-cis-octen-1-yn-3-ol (Example 751) with chlorotrimethylsilane in the manner described in Example 5 above furnishes the subject product.

EXAMPLE 753

Preparation of 1-iodo-4,4-trimethylene-3-trimethylsilyloxy-1-trans-6-cis-octadiene In the manner described in Example 6 above, treatment of 4,4-trimethylene-3-trimethylsilyloxy-6-cis-octen-1-yne (Example 752) with disiamylborane, made in situ from sodium borohydride and 2-methyl-2-butene, followed by oxidation of the so formed organoborane with trimethylamine oxide followed by treatment of this product with iodine and sodium hydroxide furnishes the subject product.

EXAMPLE 754

Preparation of 15-hydroxy-9-oxo-16,16-trimethylene-13-trans-prostenoic acid oxime To a solution of 1 g. of 9-oxo-15-hydroxy-16,16-trimethylene-13-trans-prostenoic acid (Example 8) in 20 ml. of methanol-water (1:1) is added 1 g. of hydroxylamine hydrochloride and 1.25 g. of anhydrous sodium acetate. Additional methanol is added and the resulting solution is stirred at ambient temperature for 24 hours. The solution is concentrated and the residue is diluted with water and the mixture is extracted several times with ether. The ether extracts are washed with saturated sodium chloride solution, dried and taken to dryness to furnish 972 mg. of this subject product.

EXAMPLE 755

Preparation of 11α,15-dihydroxy-9-oxo-16,16-trimethylene-5-cis,13-trans-prostadienoic acid oxime Treatment of 1 g. of 11α,15-dihydroxy-9-oxo-16,16-trimethylene-5-cis,13-trans-prostadienoic acid (Example 201) in 20 ml. of methanol-water (1:1) containing 1.25 g. of anhydrous sodium acetate with 1 g. of hydroxylamine hydrochloride in the manner described in Example 754 furnishes the subject product.

EXAMPLE 756

Preparation of 15-hydroxy-9-oxo-16,16-trimethylene-13-trans-prostenoic acid methoxime Treatment of 1 g. of 9-oxo-15-hydroxy-16,16-trimethylene-13-trans-prostenoic acid (Example 8) in 20 ml. of methanol-water (1:1) containing 1.5 g. of anhydrous sodium acetate with 1.5 g. of methoxyamine hydrochloride in the manner described in Example 754 furnishes the subject product.

EXAMPLE 757

Preparation of 11α,15-dihydroxy-9-oxo-16,16-trimethylene-5-cis,13-trans-prostadienoic acid methoxime Treatment of 500 mg. of 11α,15-dihydroxy-9-oxo-16,16-trimethylene-5-cis,13-trans-prostadienoic acid (Example 201) in 10 ml. of methanol-water (1:1) containing 600 mg. of anhydrous sodium acetate with 700 mg. of methoxyamine hydrochloride in the manner described in Example 754 is productive of the subject product.

EXAMPLE 758

Preparation of 15-hydroxy-9-oxo-16,16-trimethylene-13-trans-prostenoic acid semicarbazone To a solution of 600 mg. of 9-oxo-15-hydroxy-16,16-trimethylene-13-trans-prostenoic acid (Example 8) in 6 ml. of absolute alcohol and 3 ml. of water is added 600 mg. of semicarbazide hydrochloride and 1.2 g. of anhydrous sodium acetate. The solution is stirred at 40° C. for 1 hour then kept at ambient temperature for several hours during which time crystals are deposited. Filtration furnishes 480 mg. of the subject product.

EXAMPLE 759

Preparation of 11α,15-dihydroxy-9-oxo-16,16-trimethylene-5-cis,13-trans-prostadienoic acid semicarbazone Treatment of 1 g. of 11α,15-dihydroxy-9-oxo-16,16-trimethylene-5-cis,13-trans-prostadienoic acid (Example 201) in ethanol-water (2:1) containing 1.8 g. of anhydrous sodium acetate with 1 g. of semicarbazide hydrochloride in the manner described in Example 758 is productive of the subject product.

EXAMPLE 760

Preparation of 15-hydroxy-9-oxo-16,16-trimethylene-13-trans-prostenoic acid thiosemicarbazone To a solution of 313 mg. of 9-oxo-15-hydroxy-16,16-trimethylene-13-trans-prostenoic acid (Example 8) in 20 ml. of methanol-water (1:1) is added 275 mg. of thiosemicarbazide, followed by 1 drop of glacial acetic acid. The mixture is stirred at 40° C. for 1 hour, then clarified by filtration. The resulting solution is kept at ambient temperature for 24 hours, then at 0° C. for 24 hours. The solid material is collected by filtration to furnish the subject product.

EXAMPLE 761

Preparation of 11α,15-dihydroxy-9-oxo-16,16-trimethylene-5-cis,13-trans-prostadienoic acid thiosemicarbazone Treatment of 500 mg. of 11α,15-dihydroxy-9-oxo-16,16-trimethylene-5-cis,13-trans-prostadienoic acid (Example 201) in 30 ml. of methanol-water (1:1) with 500 mg. of thiosemicarbazide and 1 drop of glacial acetic acid in the manner described in Example 760 furnishes the subject product.

EXAMPLE 762

Preparation of 5-chloro-2,3-methano-pentanoic acid ethyl ester

A stirred mixture of 10.0 g. of 4-chloro-1-butene and 1.0 g. of copper powder (activated by washing with glacial acetic acid and drying under reduced pressure) is purged with argon and placed in a heating bath at approximately 100° C. Ethyl diazoacetate (12.45 g.) is added dropwise to the stirred reaction mixture at such a rate as to maintain gentle reflux and not too vigorous nitrogen evolution. After the addition is complete, the reaction mixture is stirred for an additional 15–30 minutes. After cooling to room temperature, the copper powder is removed by filtration through Celite and the filtrate is evaporated under reduced pressure. The residual oil (13.75 g.) is distilled under reduced pressure to afford 8.3 g. of product (b.p. 42°–43° C. at 0.14 mm).

EXAMPLE 763

Preparation of 5-chloro-2,3-methano-pentanoic acid

A mixture of 1.42 g. of 5-chloro-2,3-methano-pentanoic acid ethyl ester (Example 762) and 1.59 g. of potassium hydroxide in 50 ml. of methanol and 5 ml. of water is purged with argon and stirred at room temperature for 18 hours. After evaporation of methanol under reduced pressure, the residue is diluted with a small amount of water and extracted with ether to remove any neutral material. The basic aqueous phase is acidified with 4 N hydrochloric acid and extracted into ether. The extract is washed with saturated saline, dried over magnesium sulfate, filtered through Celite and evaporated under reduced pressure. The residue is slurried with hexane and filtered to remove any maleic and fumaric acid (minor contaminants in the starting material in the form of their diethyl esters). The filtrate is evaporated to afford 0.68 g. of product as a colorless oil.

EXAMPLE 764

Preparation of 5-iodo-2,3-methano-pentanoic acid

A mixture of 4.92 g. of 5-chloro-2,3-methano-pentanoic acid (Example 763) and 15 g. of sodium iodide in 65 ml. of acetone is stirred and heated under reflux for 40 hours. The reaction mixture is cooled to room temperature and the sodium chloride precipitate is filtered and washed with acetone. The filtrate is evaporated under reduced pressure and the residue partitioned between water and ether. The aqueous phase is extracted three additional times with ether and the combined extracts are washed with water and saturated saline, dried over magnesium sulfate, filtered through Celite and evaporated under reduced pressure to afford 7.48 g. of product. NMR indicates approximately 90% purity.

EXAMPLE 765

Preparation of 4-carboxy-3,4-methanobutyltriphenylphosphonium iodide

A mixture of 7.48 g. of 5-iodo-2,3-methano-pentanoic acid (Example 764) and 8.6 g. of triphenylphosphine in 30 ml. of acetonitrile is refluxed with stirring under argon for 3 days. The reaction mixture is cooled to room temperature and diluted with approximately 150 ml. of benzene and a large amount of ether. After tacky precipitate is obtained by scratching with a glass rod, the mother liquor is decanted and fresh ether added to the tacky solid. The amorphous solid obtained by aging is filtered and washed with ether to afford 15.3 g. of product.

EXAMPLE 766

Preparation of
2-(6'-carboxy-5',6'-trans-methano-2'-cis-hexenyl)-3,4-oxidocyclopentanol A solution of the sodium salt of dimethylsulfoxide is prepared from 888 mmoles of sodium hydride (washed free from mineral oil) and 440 ml. of dimethylsulfoxide. The solution is treated during 15 minutes with a solution of 192 g. (434 mmoles) of 4-carboxy-3,4-methano-butyl-triphenylphosphine iodide (Example 765) in 710 ml. of dimethylsulfoxide while cooling at 20°-25° C. After 15 minutes the dark red solution was cooled to 17° C. and treated with a solution of 25 g. of the hemiacetal of cis-2-hydroxy-4,5-epoxy-cyclopent-1-acetaldehyde [Floyd, M. B., Synthetic Communications, 4(6), 317 (1974)] in 100 ml. of dimethylsulfoxide during 2 minutes. After 2 hours at ambient temperature, the solution is poured onto 2.5 kg. of ice, acidified with dilute hydrochloric acid, and extracted with ethylacetate. The extract was washed with brine, dried with anhydrous magnesium sulfate and taken to dryness. The resulting oil is slurried with 200 ml. of ether, filtered and the ether is evaporated to furnish 56 g. of the subject product.

EXAMPLE 767

Preparation of
2-(6'-carboxy-5',6'-trans-methano-2'-cis-hexenyl)-3,4-oxidocyclopentanone To a stirred solution of 50 g. of 2-(6'-carboxy-5',6'-trans-methano-2'-cis-hexenyl)-3,4-oxidocyclopentanol (Example 766) in 875 ml. of acetone is added 50 ml. of 8 N Jones reagent during 25 minutes at −12° to −10° C. After 15 minutes at −12° C. the solution is treated with 10 ml. of isopropanol and filtered. The filtrate is treated with 200 ml. of water and concentrated. The resulting suspension is saturated with salt and extracted with ethyl acetate. The extract is washed with saturated sodium chloride solution, dried and taken to dryness to give 38 g. of product.

EXAMPLE 768

Preparation of
2-(6'-carboxy-5,6-trans-methano-2'-cis-hexenyl)-4-hydroxycyclopent-2-en-1-one A solution of 74 g. of anhydrous sodium carbonate and 300 mg. of hydroquinone in 3000 ml. of water is outgassed with nitrogen. 2-(6'-carboxy-5',6'-trans-methano-2'-cis-hexenyl)-3,4-oxidocyclopentanone (38 g.) (Example 767) is added with stirring under nitrogen to give a cloudy, amber solution. After 24 hours the solution is cooled in an ice bath, acidified with dilute hydrochloric acid, saturated with salt and extracted with ethyl acetate. The extract is washed with brine, dried and taken to dryness to give 35 g. of an oil. This oil is dissolved in 200 ml. of ether-acetone (5:1) and chromatographed on 800 g. of Davison #923 silica gel using ether progressively enriched in acetone (0-20%) as elution solvent. Fractions which contain essentially one spot by thin layer chromatography (100:1 ethyl acetate-acetic acid) was combined to give 13 g. of the subject product.

EXAMPLE 769

Preparation of
2-(6'-carbotetrahydropyranyloxy-5,6-trans-methano-2'-cis-hexenyl)-4-tetrahydropyranyloxycyclopent-2-en-1-one To a solution of 24 g. of 2-(6'-carboxy-5,6-trans-methano-2'-cis-hexenyl)-4-hydroxycyclopent-2-en-1-one (Example 768) and 45 g. of freshly distilled dihydropyran in 330 ml. of dry methylene chloride stirred in a cold water bath is added dropwise a solution of 202 mg. of p-toluenesulfonic acid in 150 ml. of methylene chloride. After an additional 1½ hours, 575 ml. of ether is added and the solution is poured into 138 ml. of saturated brine, 138 ml. of saturated sodium bicarbonate solution and 350 ml. of water. The organic phase is separated and washed with saturated brine, dried with a mixture of anhydrous magnesium sulfate and anhydrous potassium carbonate, and taken to dryness to furnish 35 g. of subject product.

EXAMPLE 770

Preparation of
11α,15-dihydroxy-2,3-trans-methano-9-oxo-16,16-trimethylene-5-cis,13-trans-prostadienoic acid The subject product is obtained by the procedure described in Example 201 above. In accordance with the process described therein, 1-iodo-4,4-trimethylene-3-trimethylsilyloxy-1-trans-octene (Example 6) is treated with t-butyllithium providing the corresponding trimethylsilyl substituted trans-1-alkenyl lithium derivative which on treatment with cuprous pentyne furnishes the corresponding lithio-pentynyl (trimethyl-substituted trans-1-alkenyl)cuprate, which in turn is treated with 2-(6'-carbotetrahydropyranyloxy-5,6-trans-methano-2'-cis-hexenyl)-4-tetrahydropyranyloxycyclopent-2-en-1-one (Example 769). The resulting trimethylsilyl substituted 11α-tetrahydropyranyloxy-2,3-trans-methano-9-oxo-16,16-trimethylene-5-cis, 13-trans-prostadienoic acid tetrahydropyranyl ester is hydrolyzed by treatment with acetic acid-tetrahydrofuran-water to give the subject product.

EXAMPLE 771

Preparation of
2-(5,6-methano-6-carboxyhexyl)cyclopent-2-en-1-one

A mixture of 30 g. of 2-85,6-methano-6-carbethoxyhexyl)cyclopent-2-en-1-one (Example 745) in 1250 ml. of methanol-water (1:1) containing 25 g. of potassium hydroxide was stirred at 50° C. for 1 hour, then at ambient temperature for 24 hours. The resulting solution is acidified with dilute hydrochloric and extracted several times with ether. The combined extracts are washed with saturated sodium chlroide solution, dried with anhydrous magnesium sulfate and taken to dryness to furnish the subject product.

EXAMPLE 772

Preparation of
4-bromo-2-(5,6-methano-6-carboxyhexyl)-cyclopent-2-en-1-one

A stirred mixture of 35 g. of 2-(5,6-methano-6-carboxyhexyl)cyclopent-2-en-1-one (Example 771), 35 g. of N-bromosuccinamide and 600 ml. of carbon tetrachloride is refluxed for 35 minutes. The mixture is cooled to 5° C. and filtered. The filtrate is washed with cold water, dried with anhydrous magnesium sulfate and taken to dryness to give an oil.

EXAMPLE 773

Preparation of 4-hydroxy-2-(5,6-methano-6-caroxyhexyl)cyclopen-2-en-1-one

To a stirred solution of 57.2 g. of crude 4-bromo-2-(5,6-methano-6-carboxyhexyl)cyclopent-2-en-1-one (Example 772) in 500 ml. of acetone and 325 ml. of water at 3° C. is added 44.1 g. (0.226 moles) of silver fluoborate during a 15-minute period. The mixture is stirred at 0°–3° C. for 2 hours and filtered. The filtrate is diluted with water, saturated with solid sodium chloride, and extracted with ether. The extract is washed with saturated sodium chloride solution, dried over magnesium sulfate, and concentrated. Partition chromatography of the residue on Celite gives the subject product, $\lambda_{max.}^{MeOH} = 223$ mu (7800); $\nu$max (KBr)=3340 (hydroxyl groups), 1705 (carbonyl groups), and 1625 cm$^{-1}$ (olefin group).

EXAMPLE 774

Preparation of 4-tetrahydropyranyloxo-2-(5,6-methano-6-carbotetrahydropyranyloxy)cyclopent-2-en-1-one To a solution of 25 g. of 4-hydroxy-2-(5,6-methano-6-carboxyhexyl)cyclopent-2-en-1-one (Example 773) and 45 g. of dihydropyran in 330 ml. of dry methylene chloride is added dropwise a solution of 300 mg. of p-toluenesulfonic acid in 200 ml. of methylene chloride maintaining the temperature at 20°–25° C. Stirred for an additional hour, then added 600 ml. of ether. The solution is poured into a mixture of 200 ml. of saturated sodium bicarbonate, 200 ml. of brine, and 400 ml. of water. The organic phase is separated, dried with anhydrous magnesium sulfate and taken to dryness to furnish 35 g. of subject product.

The ring system of certain of the novel compounds of this invention allow them to be characterized as follows:

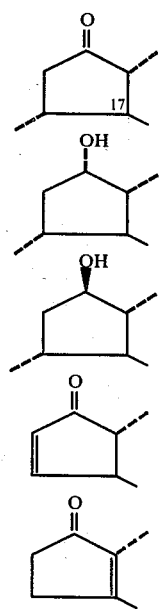

The novel compounds of this invention possess the pharmacological activity described below as associated with the appropriate above-described prostaglandin type.

The known PGE, PGF$_\alpha$, PGF$_\beta$, PGA, and PGB compounds are all potent in causing multiple biological responses even at low doses. For example, PGE$_1$ and PGE$_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandins analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, PGF$\alpha$ and PGF$\beta$ compounds are additionally selective in that they are at most relatively very weak stimulants of smooth muscle. The 11-deoxy PGE compounds have a further advantage in that they are as much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, bucally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body wit fewer, shorter, or smaller doses, and make possible self-administration by the patient.

PGE$_1$, PGE$_2$, PGE$_3$, and dihydro-PGE$_1$, and the corresponding PGF$_\alpha$, PGF$_\beta$, PGA, and PGB compounds, and their esters and and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the PGE, and PGF$\beta$ and PGA compounds as measured, for example, in anesthetized (penobarbital sodium) pentolinium-treated rats with indwelling aortic and right heart cannulas; pressor activity, similarly measured, for the PGF$\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the cetral nervous system; decrease of blood platelet adhesiveness in he case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The PGE and PGA compounds are useful in mammals, including man and certain useful antimals, e.g., dogs and pigs, to reduce and control excessive gastric secretion, thereby reducing or avoiding gastric erosion of gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE$_1$ compounds useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intraveneously, subcutaneously, intramuscularly, and in the form of sterile implants for prolonged action. For rapid response, especially in emergency situations, the intravenous route of administration is preferred. Doses in the range of about 0.005 to about 20 mg. per kg. of body weight per day are used, the exact dose depending on the age, weight, and condition of the patient or animal, and on the frequency and route of administration.

11$\alpha$-Hydroxy-PGE compounds are extremely potent in causing stimulation of smooth muscle, and are also highly active in potentiating other known smooth muscle stimulators, for example, oxytocic agents, eg., oxytocin, and the various ergot alkaloids including derivatives and analogs thereof. Therefore PGE$_2$, for example, in useful in place of or in combination with less then usual amounts of these known smooth muscle stimulators, for example, to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delvery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range of 0.01 to 2 mg. per kg. of body weight per day, the exact dose depending on the age, weight, and condition of the patient or animal.

The PGE, PGF$\beta$ and PGA compounds are useful as hypotensive agents to reduce blood pressure in mammals including man. For this purpose, the compounds are administered by intravenous infusion at the rate about 0.01 to about 50 $\mu$g. per kg. of body weight per minute, or in a single or multiple doses of about 25 to 2500 $\mu$g. of body weight total per day.

The PGE, PGF$\alpha$, and PGF$\beta$ compounds are useful in place of oxytoxin to induce labor in pregnant female animals, including man, cows, sheep, pigs, at or near term or in pregnant animals with intrauterine death of the fetus from about 20 weeks to term. For this purpose, the compound is infused intravenously at a dose 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started.

The PGE, PGF$\alpha$, and PGF$\beta$ compounds are useful for controlling the reproductive cycle in ovulating female mammals, including humans and other animals. For that purpose, PGF$_{2\alpha}$, for example, is administered systematically at a dose level in the range of 0.01 mg. to about 20 mg. per kg. of body weight, advantageously during a span of time starting approximately at the time of ovulation and ending approximately at the time of menses or just prior to menses. Additionally, expulsion of an embryo or fetus is accomplished by similar administration of the compound during the first third or the second third of the normal mammalian gestation period. Accordingly they are useful as abortifacients. They are also useful for induction of menses during apprimately the first two weeks of a missed mestrual period and accordingly are useful as contraceptive anti-fertility agents.

The PGA compounds and derivatives and salts thereof increase the flow of blood in the mammalian kidney, thereby increasing volume and electrolyte content of the urine. For that reason, PGA compounds are useful in managin cases of renal disfunction, especially in cases of several impaired renal blood flow, for example, the hepatorena sydrome and early kidney transplant rejection. In case of excessive or inappropriate ADH (antidiuretic hormone vasopressin) secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, where there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 µg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The novel compounds of this invention induce the biological responses described hereinabove as associated with its particular prostaglandins type. These novel compounds are accordingly useful for the above-described corresponding purposes in the same manner as described above.

The novel PGE, PGFβ and PGA compounds of this invention are also useful as bronchodilators for the treatment of asthma and chronic bronchitis; as such they may be conveniently administered by inhalation of aerosol sprays prepared in a dose range of about 10 µg. to about 10 mg. per ml. of a pharmacologically suitable liquid vehicle.

The novel compounds of this invention wherein Y is

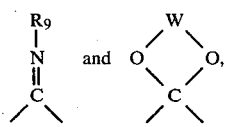

as defined hereinabove, unexpectedly also possess prostaglandin-like activity of the type described above as associated with the PGF structure. This novel and completely unexpected finding offers significant and important advantages for these derivatives of this invention relative to the corresponding ketones. The prostaglaninds of the 11α-hydroxy E series (9-ketones) have a significant degree of instability mainly because they suffer facile elimination of the 11-hydroxy group. Accordingly, compounds of the 11-hydroxy-PGE type have a very limited shelf-life and certain applications are restricted, particularly when it is necessary to keep the prostaglandins in solution for prolonged periods, as for example with certain aerosol preparations for bronchodilator use. Thus it is recommended that prostaglandin $E_2$ when prepared in a solution in absolute ethanol be stored under refrigerated conditions (40° C.) and preferably in a deep freezer (−20° C.). Saline solutions when stored at 40° C. should be used within a week and preferably within 2-3 days. At room temperature the solution must be used in one day. It has been shown "that a significant decrease in prostaglandin $E_2$ biological activity occurs after ten days storage at 4° C. at a concentration of 100 mg./ml." [(See T. J. Rosiman, B. Jims and R. G. Shaub, Amer. J. Hosp. Pharm., 30, 236 (1973).] Since the above described ketals, hydrazones, etc. also possess biological activity, but at the same time do not suffer from the inherent instability of the 11-hydroxy-9-ketones, they can be advantageously substituted for the latter, particularly in applications such as aerosol preparation for bonchodilator use, infusion solutions and the like.

These derivatives described hereinabove are also more selective in their biological action and induce a more prolonged effect then the corresponding ketones. Both of these preparations are novel, completely unanticipated and provide distinct and important advantages.

In addition certain of the novel compounds of this invention are useful for the preparation of other novel compounds of this invention.

The compounds of this invention are useful as bronchodilators for the treatment of asthma and chronic bronchitis. Bonchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, *Arzneimittel-Forschung*, 18, 955 (1968).]

In Table A which follows bronchodilator activity for representative compounds of this invention against one or more of three spasmogenic agents is expressed as an $ED_{50}$ determined from the results obtained with three logarithmic cumulative intravenous doses.

Table A

| | Bronchodilator Activity (Konzett Assays) $ED_{50}$, mg./kg. Spasmogenic Agent | | |
|---|---|---|---|
| Compound | 5-Hydroxy-tryptamine | Histamine | Acetylcholine |
| 9-oxo-15-hydroxy-16-spirocylobutyl-13-trans-prostenoic acid | 0.02 | 0.0024 | 0.048 |
| 9-oxo-15-epi-hydroxy-16-spirocyclobutyl- | | | |

Table A-continued

| | Bronchodilator Activity (Konzett Assays) ED$_{50}$, mg./kg. Spasmogenic Agent | | |
|---|---|---|---|
| Compound | 5-Hydroxy-tryptamine | Histamine | Acetylcholine |
| 13-trans-prostenoic acid | 0.135 | 0.014 | 0.003 |
| 9-oxo-11α,15-dihydroxy-16-spirocyclo-butyl-5-cis,13-trans-prostadienoic acid | 0.0025 | 0.0015 | 0.0011 |
| 9-oxo-11α,15-epi-dihydroxy-16-spiro-cyclobutyl-5-cis,13-trans-prostadienoic acid | 0.305 | 0.048 | 0.032 |

These compounds have an additional importance in that they produce a sustained bronchodilation, when compared to that produced by PGE$_1$ or PGE$_2$ or the standard isoprotproterenol.

The compounds of this invention are also useful as inhibitors of gastric acid secretion and peptic ulcer formation and may be used for the treatment of gastric hyperacidity, gastric erosion, and peptic ulcer. Inhibition of basal gastric acid secretion can be determined by the following procedure.

Female Sprague-Dawley rats weighing 140-160 grams are fasted in individual cages for 18-24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4-0 Mersilene. The rat is then dosed by injection of the compound into the duodenum (1.0 ml. per 100 gram body weight). After dosing, the abdominal wall and skin are closed using metal wound clips. The rat is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. The hourly samples are then transferred to a 15 ml. centrifuge and centrifuged for 5-10 minutes. Total and sediment volume are then recorded with the supernatant volume being used as volume of secretion. A 1 ml. or less aliquot is then removed and placed in a 50 ml. beaker containing 10 ml. of distilled water. This sample is then titrated using 0.01 N NaOH to pH 7.0 using a Beckman zeromatic pH meter. Volume, titratable acidity (meq/L) and total acid output (ueg/hour) are recorded. Percent inhibition is determined by comparison with the appropriate control. Groups of three rats were used for preliminary testing, and groups of six rats were used for dose-response evaluations. All compounds are administered in a vehicle consisting of 0.5% methocel, 0.4% tween 80, and saline at a constant volume of 1 ml./100 gram rat. Samples are dispersed by sonification. Percent inhibition is calculated on basis of concurrent vehicle control.

In Table B which follows is given the effect on total acid output after 60 minutes (response A) and 120 minutes (response B) for various doses of representative compounds of this invention.

Table B

INHIBITION OF GASTRIC ACID SECRETION IN THE ACUTE GASTRIC FISTULA RAT

| | | %-Inhibition of Total Acid Output | |
|---|---|---|---|
| | Dose, mg./kg. | After 60 min. | After 120 min. |
| 9-oxo-11α,15-dihydroxy-16-spirocyclobutyl-5-cis,13-trans-prostadienoic acid | 10$^a$ | 100 | 100 |
| | 10$^b$ | 100 | 100 |
| | 2.5$^b$ | 87 | 74 |
| | 1.25$^b$ | 40 | 36 |
| | 0.63$^b$ | 30 | 35 |
| 9-oxo-11α,15-epi-dihydroxy-16-spirpcyclo-butyl-5-cis,13-trans-prostadienoic acid | 10$^a$ | 98 | 86 |
| | 10$^b$ | 32 | 39 |
| 9-oxo-15-hydroxy-16-spirocyclobutyl-13-trans-prostenoic acid | 10$^a$ | 98 | 75 |
| | 2.5$^b$ | 86 | 83 |
| 9-oxo-15-epi-hydroxy-16-spirocyclobutyl-13-trans-prostenoic acid | 10$^a$ | 98 | 92 |
| | 10$^b$ | 85 | 61 |
| ethyl 9-oxo-15-hydroxy-16-spirocyclobutyl-13-trans-prostenoate | 10$^a$ | 100 | 100 |
| | 10$^b$ | 48 | 38 |
| ethyl 9-oxo-15-epi-hydroxy-16-spirocyclo-butyl-13-trans-prostenoate | 10$^a$ | 98 | 87 |
| | 10$^b$ | 77 | 67 |

$^a$intraduodenal route of administration
$^b$oral route of administration

When administered orally to a gastric fistula dog 9-oxo-11α,15-dihydroxy-16 spirocyclobutyl-5-cis,13-trans-prostadienoic acid will inhibit the stimulation of gastric acid output by gastrin tetrapeptide or histamine. With the former agent a dose of 0.16 mg./kg. is sufficient to inhibit more than 50% of the control output.

We claim:

1. A compound selected from the group consisting of an optically active compound of the formula:

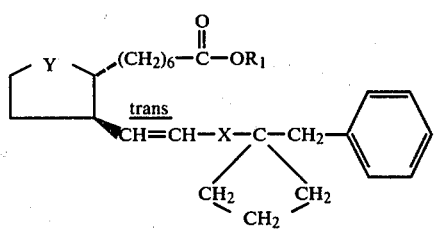

and a racemic compound of that formula and the mirror image thereof wherein X is a divalent radical selected from the group consisting of those of the formulae:

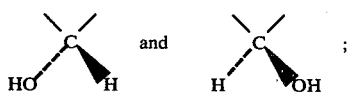

Y is a divalent radical selected from the group consisting of those of the formulae:

$R_1$ is hydrogen or alkyl having up to 4 carbon atoms; and the pharmacologically acceptable salts thereof when $R_1$ is hydrogen.

2. A compound according to claim 1 wherein X is

and Y is

3. A compound according to claim 1 wherein X is

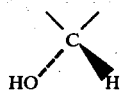

and Y is a divalent radical selected from the group consisting of those of the formulae:

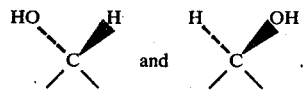

4. A compound according to claim 3 wherein Y is

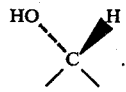

5. The optically active compound according to claim 2; nat. 9-oxo-15α-hydroxy-16,16-trimethylene-17-phenyl-18,19,20-trinor-13-trans-prostenoic acid.

6. The racemic compound according to claim 3; dl-9-oxo-15α-hydroxy-16,16-trimethylene-17-phenyl-18,19,20-trinor-13-trans-prostenoic acid.

7. The optically active compound according to claim 3; nat. 9α,15α-dihydroxy-16,16-trimethylene-17-phenyl-18,19,20-trinor-13-trans-prostenoic acid.

8. The racemic compound according to claim 3; dl-9α,15α-dihydroxy-16,16-trimethylene-17-phenyl-18,19,20-trinor-13-trans-prostenoic acid.

9. The racemic compound according to claim 3; dl-9β,15α-dihydroxy-16,16-trimethylene-17-phenyl-18,19,20-trinor-13-trans-prostenoic acid.

* * * * *